US011139336B1

(12) United States Patent
Yan

(10) Patent No.: US 11,139,336 B1
(45) Date of Patent: Oct. 5, 2021

(54) METHOD FOR FABRICATING A THROUGHPUT-SCALABLE ANALYTICAL SYSTEM FOR MOLECULE DETECTION AND SENSING

(71) Applicant: GeneSense Technology Inc., Shanghai (CN)

(72) Inventor: Mei Yan, Shanghai (CN)

(73) Assignee: GeneSense Technology Inc., Shanghai (CN)

(*) Notice: Subject to any disclaimer, the term of this patent is extended or adjusted under 35 U.S.C. 154(b) by 0 days.

(21) Appl. No.: 17/127,807

(22) Filed: Dec. 18, 2020

Related U.S. Application Data

(63) Continuation of application No. PCT/CN2020/080485, filed on Mar. 20, 2020.

(51) Int. Cl.
| | | |
|---|---|---|
| *H01L 27/00* | (2006.01) | |
| *H01L 27/146* | (2006.01) | |
| *H01L 31/18* | (2006.01) | |

(52) U.S. Cl.
CPC .... *H01L 27/1469* (2013.01); *H01L 27/14634* (2013.01); *H01L 27/14636* (2013.01);
(Continued)

(58) Field of Classification Search
CPC ........... H01L 27/1469; H01L 27/14634; H01L 27/14636; H01L 27/14687; H01L 27/14698; H01L 31/1892
See application file for complete search history.

(56) References Cited

U.S. PATENT DOCUMENTS 8,736,006 B1 * 5/2014 Tsai .................... H01L 27/1464
257/432
8,906,320 B1   12/2014 Eltoukhy et al.
(Continued)

FOREIGN PATENT DOCUMENTS

| WO | 2015/056028 A1 | 4/2015 |
| WO | 2018/085642 A1 | 5/2018 |
| WO | 2020/232581 A1 | 11/2020 |

OTHER PUBLICATIONS

Fossum et al. "The Quanta Image Sensor: Every Photon Counts," Sensors, 2016, vol. 16, No. 8, 25 pages.
(Continued)

*Primary Examiner* — Mounir S Amer
*Assistant Examiner* — Alexander Belousov
(74) *Attorney, Agent, or Firm* — Mauriel Kapouytian Woods LLP; Liang Huang

(57) ABSTRACT

A method for fabricating a throughput-scalable sensing system is disclosed. The method includes receiving a first semiconductor wafer and a second semiconductor wafer. The first semiconductor wafer includes a semiconductor substrate and a plurality of sensors disposed in the semiconductor substrate. Each sensor of the plurality of sensors is disposed in a separate semiconductor die of the first semiconductor wafer. The method further includes bonding the first semiconductor wafer to the second semiconductor wafer and preparing the bonded first semiconductor wafer and the second semiconductor wafer for conductive path redistribution. The method further includes forming one or more redistribution paths and dicing an array of semiconductor dies as a group from the plurality of semiconductor dies. The array of semiconductor dies includes a group of sensors associated with the throughput-scalable sensing system.

24 Claims, 26 Drawing Sheets

(52) U.S. Cl.
CPC .. *H01L 27/14687* (2013.01); *H01L 27/14698* (2013.01); *H01L 31/1892* (2013.01)

(56) References Cited

U.S. PATENT DOCUMENTS

| | | |
|---|---|---|
| 8,907,439 B1 | 12/2014 | Kay et al. |
| 8,936,763 B2 | 1/2015 | Rothberg et al. |
| 9,658,161 B2 | 5/2017 | Saxena et al. |
| 9,961,291 B2 | 5/2018 | Chen |
| 10,921,240 B1 | 2/2021 | Yan |
| 2006/0014151 A1 | 1/2006 | Ogura et al. |
| 2012/0074956 A1 | 3/2012 | Fife et al. |
| 2015/0057194 A1 | 2/2015 | McCaffrey et al. |
| 2015/0119259 A1 | 4/2015 | Ju et al. |
| 2016/0327507 A1 | 11/2016 | Davis et al. |
| 2016/0356715 A1 | 12/2016 | Zhong et al. |
| 2018/0155782 A1 | 6/2018 | Zhong |

OTHER PUBLICATIONS

Oxford Nanopore Technologies, https://nanoporetech.com/products/minion, 2020, 1 page.
Oxford Nanopore Technologies, https://nanoporetech.com/products/gridion, 2020, 1 page.
International Search Report and the Written Opinion issued in International Application No. PCT/CN2020/080485, dated Dec. 21, 2020, 9 pages.
U.S. Appl. No. 17/127,917, filed Dec. 18, 2020.

* cited by examiner

METHOD FOR FABRICATING A THROUGHPUT-SCALABLE ANALYTICAL SYSTEM FOR MOLECULE DETECTION AND SENSING

CROSS REFERENCE TO RELATED APPLICATIONS

This application is a continuation of International Application No. PCT/CN2020/080485 filed on Mar. 20, 2020. This application is also related to U.S. application Ser. No. 16/865,126 filed on May 1, 2020. The entire contents of these applications are hereby incorporated herein by reference for all purposes.

FIELD OF THE DISCLOSURE

The present disclosure generally relates to biomedical sample analytical systems and, more specifically, to high throughput systems for providing scalable, high speed, and high throughput molecule detection and analysis.

BACKGROUND

Biological sample analytical systems are used for various applications such as nucleic acid sequencing applications. Some of these applications may require high throughput and throughput scalability, thus necessitating an increased pixel array size for sensors (e.g., image sensors) used in such applications. In existing analytical systems, the traditional way to obtain a large pixel array size for an image sensor is to customize the design of the image sensor according to the throughput requirement. For example, for an application that requires a CMOS (complementary metal-oxide-semiconductor) image sensor to have a particular pixel array size, a designer would need to customize or completely re-design an existing image sensor having a smaller pixel array size. For a large pixel array size image sensor, the re-design of the image sensor may require not only incorporating more photodiodes in the image sensor, but also re-designing signal processing circuitry such as drivers and readout circuits that are necessary for processing electrical signals generated by the photodiodes.

SUMMARY OF THE DISCLOSURE

Re-designing an image sensor for a specific application may involve challenging design tasks, extended time-to-market due to design-testing cycles needed for fabricating working semiconductor sensor chips, and consequently higher re-design costs. Moreover, the costs of re-design can quickly rise to an impractical or prohibitive level if there are many specific system throughput requirements necessitating different pixel array sizes for different applications. Further, the traditional approach of re-designing image sensors may be associated with poor system scalability. For example, if an image sensor manufacturer has different analytical products targeting dozens of different markets or applications, image sensors with different pixel array sizes may need to be designed separately. But the design of a smaller pixel array size image sensor may not be easily adapted or scaled to obtain a design of a larger pixel array size image sensor. Thus, the traditional way to scale a design of a smaller pixel array size image sensor to that of a larger pixel array size image sensor is often inflexible, inefficient, and costly. Therefore, it is desired to have a throughput-scalable sensing system that has a faster design turn-around time, high scalability, more design-efficiency, and more cost-efficiency.

The following presents a simplified summary of one or more examples in order to provide a basic understanding of the disclosure. This summary is not an extensive overview of all contemplated examples, and is not intended to either identify key or critical elements of all examples or delineate the scope of any or all examples. Its purpose is to present some concepts of one or more examples in a simplified form as a prelude to the more detailed description that is presented below.

In accordance with some embodiments, a throughput-scalable image sensing system for analyzing biological or chemical samples is provided. The system includes a plurality of image sensors configured to detect at least a portion of light emitted as a result of analyzing the biological or chemical samples. The plurality of image sensors is arranged on a plurality of wafer-level packaged semiconductor dies of a single semiconductor wafer. Each image sensor of the plurality of image sensors is disposed on a separate wafer-level packaged semiconductor die of the plurality of wafer-level packaged semiconductor dies. Neighboring wafer-level packaged semiconductor dies are separated by a dicing street; and the plurality of wafer-level packaged semiconductor dies and a plurality of dicing streets are arranged such that the plurality of wafer-level packaged semiconductor dies can be diced from the single semiconductor wafer as a group.

In accordance with some embodiments, a throughput-scalable chemical sensing system for analyzing biological or chemical samples is provided. The system includes a plurality of chemically sensitive sensors configured to detect ion concentration. The plurality of chemically sensitive sensors is arranged on a plurality of wafer-level packaged semiconductor dies of a single semiconductor wafer. Each chemically sensitive sensor of the plurality of chemically sensitive sensors is disposed on a separate wafer-level packaged semiconductor die of the plurality of wafer-level packaged semiconductor dies. Neighboring wafer-level packaged semiconductor dies are separated by a dicing street; and the plurality of wafer-level packaged semiconductor dies and a plurality of dicing streets are arranged such that the plurality of wafer-level packaged semiconductor dies can be diced from the single semiconductor wafer as a group. At least one chemically sensitive sensor of the plurality of chemically sensitive sensors includes a plurality of ion-sensitive field effect transistors (ISFETs). At least one of the plurality of ISFETs includes a semiconductor substrate, a floating gate structure disposed above the semiconductor substrate, and a dielectric layer disposed above the floating gate structure. One or more wells are disposed above or at least partially inside the dielectric layer. At least a portion of the biological or chemical samples is disposable inside the one or more wells.

In accordance with some embodiments, a throughput-scalable sensing system for analyzing biological or chemical samples is provided. The system includes a plurality of transmembrane pore based sensors configured to detect a change of current flow as a result of analyzing the biological or chemical samples. The plurality of transmembrane pore based sensors is arranged on a plurality of wafer-level packaged semiconductor dies of a single semiconductor wafer. Each transmembrane pore based sensor of the plurality of transmembrane pore based sensors is disposed on a separate wafer-level packaged semiconductor die of the plurality of wafer-level packaged semiconductor dies. Neighboring wafer-level packaged semiconductor dies are separated by a dicing street; and the plurality of wafer-level packaged semiconductor dies and a plurality of dicing streets are arranged such that the plurality of wafer-level packaged semiconductor dies can be diced from the single semiconductor wafer as a group. At least one transmembrane pore based sensor of the group of transmembrane pores based sensors includes a semiconductor substrate and one or more detection electrodes disposed above the semiconductor substrate. The one or more detection electrodes are capable of detecting the change of current flow. The at least one transmembrane pore based sensor further includes a lipid bilayer disposed above the one or more detection electrodes. The lipid bilayer includes one or more transmembrane pores positioned corresponding to the positions of the one or more detection electrodes.

In accordance with some embodiments, a throughput-scalable photon sensing system for analyzing a biological or chemical sample is provided. The system includes a plurality of photon detection sensors configured to perform a single molecule analysis based on the biological or chemical sample. The plurality of photon detection sensors is arranged on a plurality of wafer-level packaged semiconductor dies of a single semiconductor wafer. Each photon detection sensor of the plurality of photon detection sensors is disposed on a separate wafer-level packaged semiconductor die of the plurality of wafer-level packaged semiconductor dies. Neighboring wafer-level packaged semiconductor dies are separated by a dicing street; and the plurality of wafer-level packaged semiconductor dies and a plurality of dicing streets are arranged such that the plurality of wafer-level packaged semiconductor dies can be diced from the single semiconductor wafer as a group. The system further includes a first optical waveguide configured to deliver an excitation light along a longitudinal direction of the first optical waveguide. The system further includes one or more second optical waveguides disposed above the first optical waveguide and one or more wells disposed in the one or more second optical waveguides. The one or more wells being configured to receive the biological or chemical sample. The system further includes one or more light guiding channels configured to direct photons emitted as a result of the single molecule analysis to one or more corresponding photon detection sensors of the plurality of photon detection sensors.

In accordance with some embodiments, throughput-scalable photon sensing system for analyzing biological or chemical samples is provided. The system includes a plurality of photon detection sensors configured to perform a single molecule or cluster sequencing analysis based on the biological or chemical samples. The plurality of photoelectron counting sensors is arranged on a plurality of wafer-level packaged semiconductor dies of a single semiconductor wafer. Each photon detection sensor of the plurality of photon detection sensors is disposed on a separate wafer-level packaged semiconductor die of the plurality of wafer-level packaged semiconductor dies. Neighboring wafer-level packaged semiconductor dies are separated by a dicing street; and the plurality of wafer-level packaged semiconductor dies and a plurality of dicing streets are arranged such that the plurality of wafer-level packaged semiconductor dies can be diced from the single semiconductor wafer as a group. At least one photon detection sensor of the plurality of photon detection sensors includes a plurality of sub-diffraction limit (SDL) photosensitive elements. Each SDL photosensitive element is sensitive to a single photoelectron. A single image pixel is generated based on one or more two-dimensional or three-dimensional arrays of outputs generated by SDL photosensitive elements.

In accordance with some embodiments, a method for fabricating a throughput-scalable sensing system is provided. The method includes receiving a first semiconductor wafer and second semiconductor wafer. The first semiconductor wafer includes a semiconductor substrate and a plurality of sensors disposed in the semiconductor substrate. Each sensor of the plurality of sensors is disposed in a separate wafer-level packaged semiconductor die of the first semiconductor wafer. The method further includes bonding the first semiconductor wafer to the second semiconductor wafer; and preparing the bonded first semiconductor wafer and the second semiconductor wafer for conductive path redistribution. The method further includes forming one or more redistribution paths from a plurality of electrically-conductive pads disposed at a first surface of the prepared first semiconductor wafer to a plurality of electrically-conductive spheres disposed at a first surface of the prepared second semiconductor wafer. The one or more redistribution paths are partially enclosed by one or more through-hole vias. The method further includes dicing an array of wafer-level packaged semiconductor dies as a group from the plurality of wafer-level packaged semiconductor dies. The array of wafer-level packaged semiconductor dies includes a group of sensors associated with the throughput-scalable sensing system.

BRIEF DESCRIPTION OF THE DRAWINGS

For a better understanding of the various described aspects, reference should be made to the description below, in conjunction with the following figures in which like-referenced numerals refer to corresponding parts throughout the figures.

DETAILED DESCRIPTION

Figure 1:
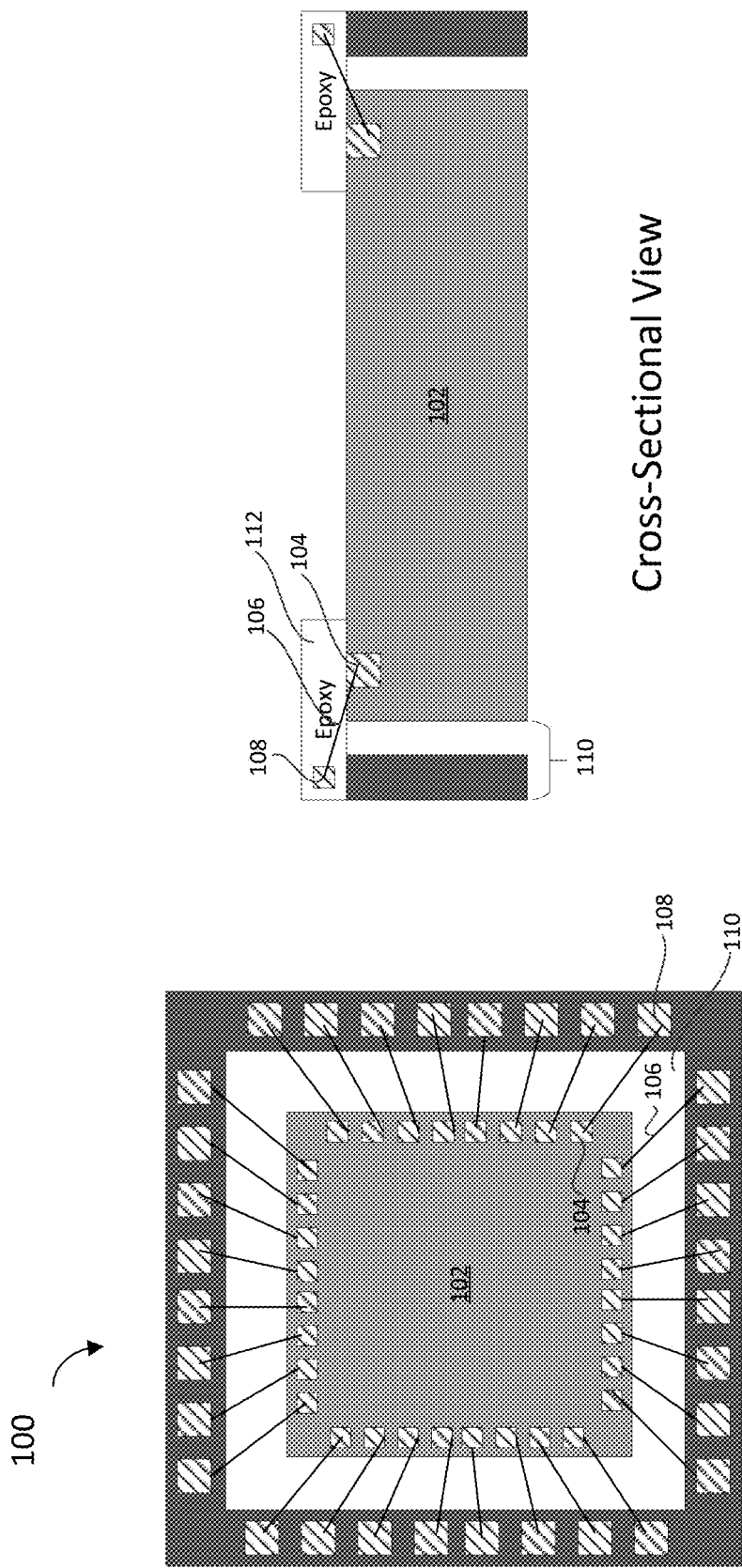
FIG. 1 is a block diagram illustrating a top view and a cross-sectional view a prior art image sensing system.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well-known structures and components are shown in block diagram form in order to avoid obscuring such concepts.

Exemplary sample throughput-scalable sensing systems will now be presented with reference to various elements of apparatus and methods. These apparatus and methods will be described in the following detailed description and illustrated in the accompanying drawing by various blocks, components, circuits, steps, processes, algorithms, etc. (collectively referred to as "elements"). These elements may be implemented using mechanical components, optical components, electronic hardware, computer software, or any combination thereof. Whether such elements are implemented as hardware or software depends upon the particular application and design constraints imposed on the overall system. Further, the same or similar elements illustrated in the drawings are labeled with the same reference numbers. Different elements may be labeled with different reference numbers.

Although the following description uses terms "first," "second," etc. to describe various elements, these elements should not be limited by the terms. These terms are only used to distinguish one element from another. For example, a first semiconductor wafer could be termed a second semiconductor wafer and, similarly, a second semiconductor wafer could be termed a first semiconductor wafer, without departing from the scope of the various described examples. The first semiconductor wafer and the second semiconductor wafer can both be semiconductor wafers and, in some cases, can be separate and different semiconductor wafers.

The throughput of a traditional image sensing system is typically not scalable or easily scalable. Scaling the throughput of such a traditional system often requires complex and costly re-design, especially if there are multiple throughput requirements to be satisfied for different sensing systems or applications. Further, traditional wire bonding technologies for packaging such a sensing system may also impose obstacles or difficulties for scaling the throughput of the sensing system. For example, as described in more detail below, traditional wire bonding technologies may not be suitable for large scale image sensing system that has a large pixel array size and may further complicate the design of a system for disposing sample channels and/or optical systems across multiple image sensors.

In this disclosure, various embodiments of throughput-scalable sensing systems are provided. These systems implement wafer-level packaging of multiple sensors disposed on multiple semiconductor dies. The multiple semiconductor dies and a plurality of dicing streets are arranged such that the multiple wafer-level packaged semiconductor dies can be diced from a single semiconductor wafer as a group. Based on the throughput scaling requirement for the sensing system and based on a throughput capacity of each sensor, the number of sensors in the sensing system can be readily determined. As a result, the throughput capacity of the sensing system can easily be scaled based on the specific application-related throughput requirement for the sensing system. Such a throughput-scalable sensing system does not require complex and costly re-design of the sensor itself (e.g., redesign to add more photosensitive elements in a single semiconductor die). Such a throughput-scalable sensing system also does not require a complex re-design or re-configuration of devices or sub-systems associated with the sensors.

Furthermore, as described in more detail below, because multiple packaged semiconductor dies in a throughput-scale sensing system are diced from a semiconductor wafer as a group, surfaces of the dies can be approximately or substantially flat across multiple dies in a sensing system. This is because the surface of a semiconductor wafer is typically flat or substantially flat and because the multiple dies are diced from the wafer as a group. The approximately or substantially flat surfaces across multiple wafer-level packaged semiconductor dies enable easy disposing of an optical system and/or a sample channel across multiple dies. This significantly reduces designing effort and solves the problem or difficulty of disposing an optical system and/or a sample channel in a traditional wire-bonding based sensing system. As described in more detail below, the group dicing technology described in this disclosure can further be combined with through-silicon via (TSV) and redistribution layer (RDL) technologies to provide signal redistribution for reducing, avoiding, or replacing the need for wire bonding. The TSV packaged semiconductor dies can maintain substantially flat surfaces across multiple semiconductor dies for enabling easy sharing of a single optical waveguide and a single sample channel across multiple sensors of a throughput-scalable sensing system.

Moreover, using the various embodiments of throughput-scalable sensing systems described in this disclosure, many biological or chemical samples can be processed or analyzed in parallel or concurrently. This improves the analysis throughput and speed over conventional analytical systems, which typically processes samples sequentially due to the throughput capacity limitation. Further, the group dicing technology enables a sensing system to be easily scaled or stacked up to provide parallel signal and data processing in a large-scale sensing application. The through-silicon via (TSV) and redistribution layer (RDL) technologies further eliminate the need for traditional wire bonding techniques for signal routing; and further enable the implementation of a high throughput or a throughput-scalable sensing system. In some embodiments, the throughput-scalable sensing system can enable concurrent data processing in the order of, for example, millions, billions, or trillions of data units (e.g., data bits representing sensed photons). The various embodiments of the throughput-scalable sensing systems can be used in or with different applications for analyzing biological or chemical samples including, for example, nucleotide acid sequencing applications and polymerase chain reaction (PCR) applications.

FIG. 1 is a block diagram illustrating a top view and a cross-sectional view a traditional image sensor system 100. System 100 includes an image sensor 102 mounted on a frame 110 of an image sensor package. The image sensor package can include, for example, a heat sink, pins, and epoxy plastic for providing protection to image sensor 102. Image sensor 102 is packaged using a traditional wire bonding based method. For example, conventionally, a plurality of bonding pads 104 is disposed at the edges of image sensor 102. Correspondingly, a plurality of bonding pads 108 is disposed at frame 110 of the image sensor package. A plurality of bonding wires 106 electrically couples pads 104 to corresponding pads 108, thereby communicating electrical signals between image sensor 102 and an external device (not shown).

Traditional image sensing system 100 has many limitations. As described above, the throughput of such as system 100 is typically not easily scalable. Scaling the throughput of such a system often requires re-designing of image sensor 102 to incorporate more photosensitive elements for satisfying the throughput requirement. Incorporating more photosensitive elements inevitably requires increasing the physical chip area of image sensor 102, re-designing the signal processing circuitry, re-designing the numbers and positions of bonding pads 104 and 108, and many design-testing cycles. The scaling of such a traditional image sensing system 100 thus requires significant redesign effort, extended time cycle to market, and increased cost. The scaling of such a traditional system becomes even more complex and costly if there are multiple throughput requirements to be satisfied for different sensing systems used for different applications.

Another limitation of traditional image sensing system 100 is specific to using system 100 for biological or chemical sample analysis applications. This limitation relates to the flatness of the surface of image sensing system 100. In such applications, sample channels or sample containers are frequently disposed above image sensing system 100 such that the light emitted by the samples can travel directly downward to the image sensors without extra optical signal routing. As shown in the cross-sectional view of image sensing system 100 in FIG. 1, bonding wires 106 are conventionally protected by epoxy material 112. Thus, due to the using of bonding wires 106 and the epoxy 112, the surface of image sensing system 100 may not be flat or substantially flat. Disposing a sample channel or container above such an uneven surface may require additional engineering efforts and may not be easily achieved. The task is further complicated if a sample channel or container is to be shared across multiple image sensors 102. For example, additional epoxy material may need to be disposed to the surface of image sensors 102 to make the surface of system 100 flat. Or the sample channel/container may need to be redesigned/reconfigured to fit into the uneven surfaces of one or more image sensors 102. Both approaches impose challenging design tasks. For instance, additional epoxy material may interfere with the light emitted from the sample disposed above image sensor 102, by absorbing, diffracting, and/or reflecting the emitted light. Thus, the additional epoxy material may render light detection impossible or impractical, or at least degrade the performance of image sensing system 100. Redesigning the sample channel/container to fit into the uneven surfaces of sensors 102 may sometimes be impractical or at least increase the cost of system 100.

Unlike traditional image sensor system 100, various embodiments of throughput-scalable sensing systems are described in this disclosure. These throughput-scalable sensing systems are based on group dicing and based on wafer-level packaging of multiple sensors disposed on multiple semiconductor dies. The multiple semiconductor dies and a plurality of dicing streets are arranged such that the multiple semiconductor dies can be diced from a single semiconductor wafer as a group. FIG. 2A illustrates an exemplary wafer map 200 of such a semiconductor wafer. A semiconductor wafer is a thin slice of semiconductor (e.g., Silicon) used for fabricating integrated circuits and/or other semiconductor devices such as sensors. Various types of sensors are described in this disclosure, including image sensors, chemically sensitive sensors, transmembrane pore based sensors, photon counting sensors, and quanta CMOS image sensors (QISs). These sensors are described in more detail below.

An image sensor is a sensor that detects photons, generate electrical signals (also referred to as photoelectrons) based on the detected photons, and transmit the electrical signals for further signal processing. In an image sensing system, photons can be generated as a result of fluorescence or chemiluminescence emissions from biological or chemical samples being analyzed. The photons are then collected and detected by photosensitive elements (e.g., pixels) included in an image sensor. Photosensitive elements can include, for example, photodiodes (e.g., silicon based photodiodes) for detecting photons and generating electrical signals based on detected photons. In some embodiments, photosensitive elements may also include amplifiers (e.g., avalanche amplification). The electrical signals generated by an image sensor can represent various photon information including the number of photons collected, the position of photons, and/or the intensity of photons. As described in more detail below, an image sensor described in this disclosure is not limited to a sensor that transmits electrical signals or information for generating an image. An image sensor used for analyzing biological or chemical samples (e.g., nucleotide acid sequencing applications, polymerase chain reaction applications) can include sensors that detect photons and transmit electrical signals for any type of signal processing with or without generating an image.

With reference to FIG. 2A, wafer map 200 represents wafer-level packaged semiconductor dies and their arrangements on a single semiconductor wafer. In some embodiments, as described in more detail below, wafer-level packaging of the semiconductor dies can include one or more of forming through-silicon vias (TSV), depositing redistribution layers, depositing passivation layers, forming electrically-conductive spheres, and disposing solder mask layers. In this disclosure, wafer-level packaged semiconductor dies are sometimes also referred to as packaged semiconductor dies or TSV-packaged semiconductor dies. In FIG. 2A, each individual block (e.g., block 202) shown on wafer map 200 can represent a packaged semiconductor die of a semiconductor wafer. A semiconductor die is a unit or a single block of semiconductor material on which integrated circuits or other devices (e.g., sensors) are fabricated. For example, an image sensor having a plurality of photosensitive elements (e.g., pixels) can be fabricated on each semiconductor die represented by an individual block (e.g., block 202) shown on wafer map 200. Exemplary embodiments of such an image sensor is described in more detail below.

In some embodiments, each image sensor can be fabricated on an individual semiconductor die. An image sensor may have a pre-configured or a pre-determined throughput capacity represented by a pixel array size. For example, an image senor may have a pixel array size of 8 megapixels, 16 megapixels, 32 megapixels, etc. Typically, for a given semiconductor process (e.g., a 45 nm CMOS image sensor process), a larger pixel array size requires more photosensitive elements such as more photodiodes. As a result, an image sensor with higher throughput capacity may require a larger physical area of a semiconductor die. In some embodiments, rather than increasing the area of a single semiconductor die, a high throughput sensing system or throughput-scalable sensing system can also be obtained based on group dicing of multiple packaged semiconductor dies.

Figure 2B:
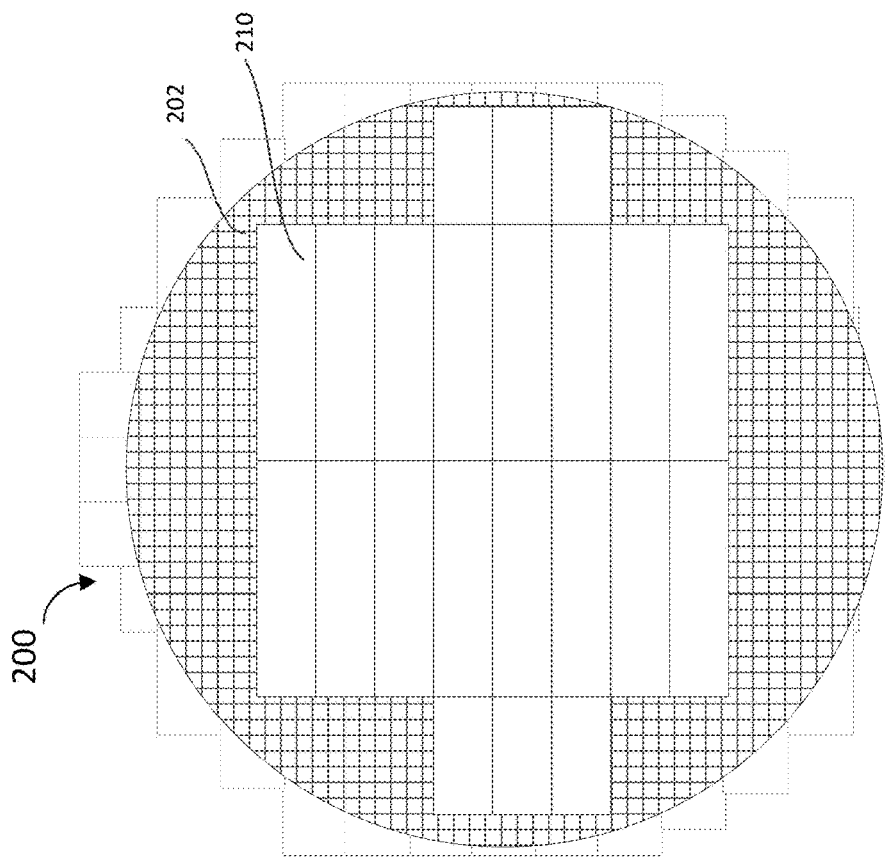
FIG. 2B illustrates an exemplary group dicing plan for dicing multiple wafer-level packaged semiconductor dies from a semiconductor wafer as groups.
Figure 2A:
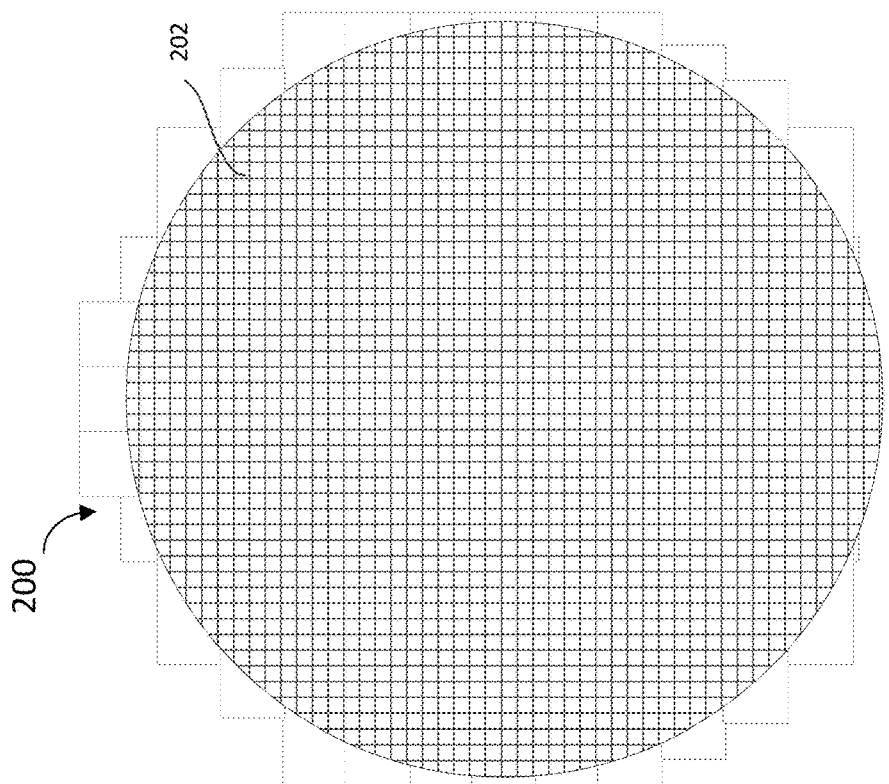
FIG. 2A illustrates an exemplary semiconductor wafer map.

FIG. 2B illustrates an exemplary group dicing plan for dicing packaged semiconductor dies from a semiconductor wafer as groups. As shown in FIG. 2B, multiple packaged semiconductor dies can be diced as a group, instead of individually, from the semiconductor wafer represented by wafer map 200. Dicing, sometimes also referred to as wafer dicing, is a process by which packaged semiconductor dies are separated from a semiconductor wafer or a wafer-level packaged semiconductor wafer. A dicing process may include scribing, breaking, mechanical sawing, and/or laser cutting. Dicing is typically performed at or near dicing streets between the packaged semiconductor dies. The dicing streets can be, for example, 80 micrometers (um) wide.

Figure 2C:
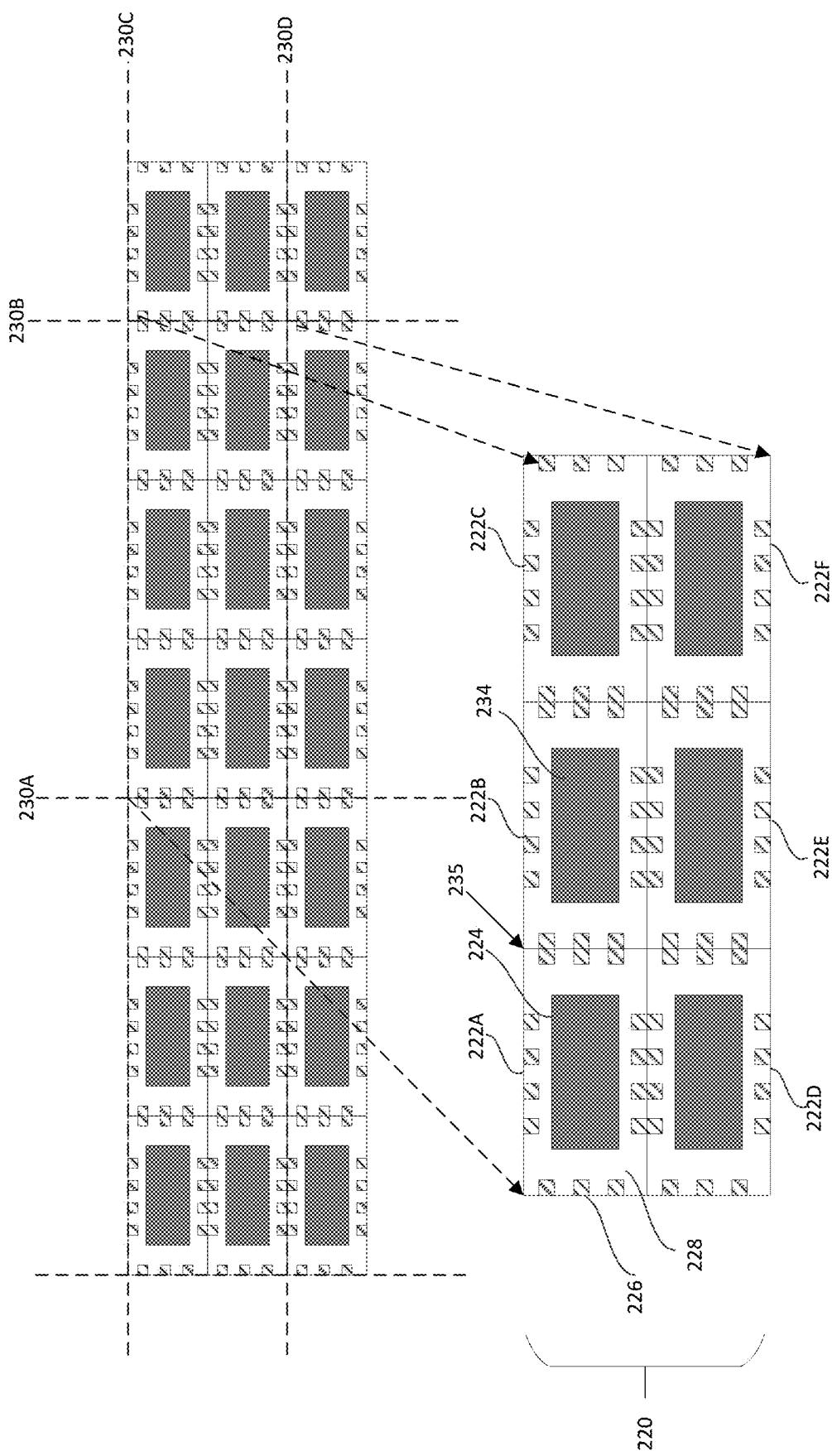
FIG. 2C illustrates a throughput-scalable image sensing system obtained based on group dicing wafer-level packaged semiconductor dies from a semiconductor wafer.

In FIG. 2B, an exemplary dicing group is represented by a block 210 illustrated on wafer map 200. The exemplary dicing group represented by block 210 may include a plurality of individual packaged semiconductor dies (e.g., 8, 16, 32, 64, etc.). An image sensor with a particular throughput capacity may be fabricated on each packaged semiconductor die in the group. Therefore, block 210 on wafer map 200 can also represent a group of image sensors disposed on the corresponding packaged semiconductor dies. FIG. 2C illustrates a throughput-scalable image sensing system obtained based on dicing multiple packaged semiconductor dies as a group from a semiconductor wafer or a wafer-level packaged semiconductor wafer. In FIG. 2C, an image sensor is pre-fabricated or disposed on each packaged semiconductor die. For example, one image sensor can be fabricated or disposed on packaged semiconductor die 222A. The image sensor disposed on packaged semiconductor die 222A may include, for example, a plurality of photosensitive elements 224, a plurality of electrically-conductive layers (not shown in FIG. 2C), a plurality of electrically-conductive pads 226, and a semiconductor (e.g., silicon) substrate 228. The components and structure of exemplary image sensors are described in more detail below.

As shown in FIG. 2C, based on a group dicing plan, the packaged semiconductor dies of the semiconductor wafer can be diced in groups. The example illustrated in FIG. 2C shows that a group of six packaged semiconductor dies 222A-F are separated from the semiconductor wafer by, for example, laser cutting along the dicing streets 230A-D without separating the packaged semiconductor dies 222A-F from one another. Dicing streets 230A-D represent the perimeter of the group of dies 222A-F. And therefore, in group dicing, the laser cutting is performed along the perimeter of the group of dies 222A-F, but not between the dies. Each of packaged semiconductor dies 222A-F can be pre-fabricated or disposed with an image sensor having a particular throughout capacity (e.g., pixel array size). The six image sensors pre-fabricated or disposed on packaged semiconductor dies 222A-F can thus form an image sensing system 220 that has six-times throughput capacity than each individual image sensor. In general, if each image sensor in an image sensing system (e.g., system 220) has a pixel array size of M megapixels and there are N number of image sensors in the image sensing system, the total pixel array size of the image sensing system is then M×N. In the example illustrated in FIG. 2C, if each image sensor disposed on semiconductor dies 220A-F has a pixel array size of 64 megapixels, and a group of six packaged semiconductor dies 220A-F form the image sensing system 220, image sensing system 220 can be scaled to have a pixel array size of 384 megapixels.

While FIG. 2C illustrates that image sensing system 220 include six image sensors disposed on six packaged semiconductor dies 220A-F, it is appreciated that the number of image sensors in a particular image sensing system can be determined or preconfigured to any desired number satisfying a throughput scaling requirement. For example, if a particular image sensing system used for a nucleotide acid sequencing application requires a total pixel array size of 1000 megapixels (or 1 Gigapixels), and if each image sensor has a pixel array size of 64 megapixels, the number of image sensors required for such an image sensing system would be about 16 (e.g., 1000/64). Correspondingly, 16 packaged semiconductor dies can be diced from the semiconductor wafer as a group (i.e., without separating the 16 dies from one another). Accordingly, based on the throughput scaling requirement for the image sensing system and based on a throughput capacity of each image sensor, the number of image sensors in the image sensing system can be readily determined. As a result, the throughput capacity of the image sensing system can easily be scalable based on requirements of the specific applications (e.g., a DNA sequencing application, a PCR application) of the image sensing system. Such a throughput-scalable system does not require complex and costly re-design of the image sensor itself (e.g., redesign to add more photosensitive elements in a single semiconductor die).

Figure 3:
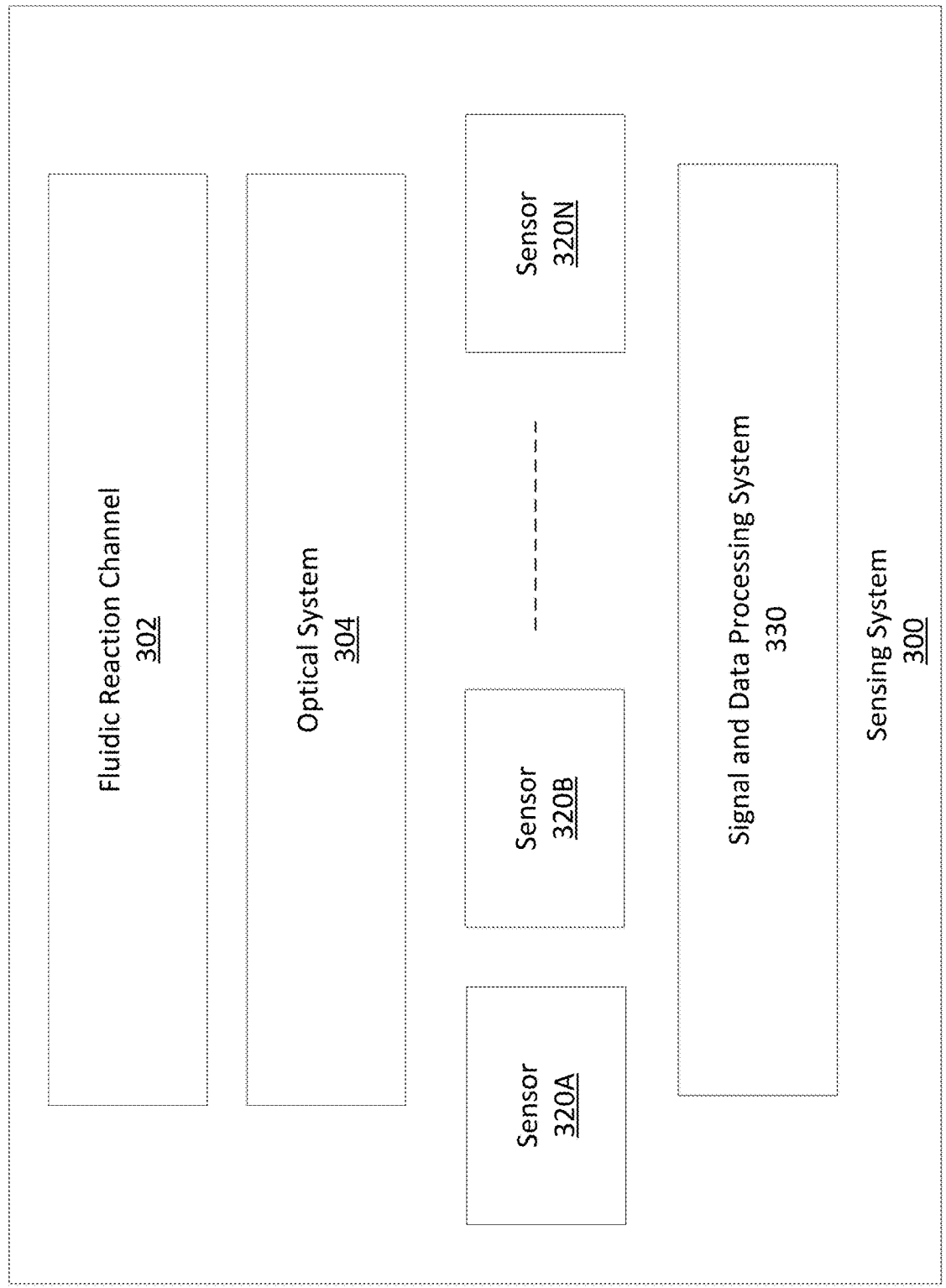
FIG. 3 is a block diagram illustrating an exemplary throughput-scalable sensing system.

Further, a throughput-scalable image sensing system described in this disclosure also does not require a complex re-design or re-configuration of devices or sub-systems operating with the image sensors. FIG. 3 is a block diagram illustrating a throughput-scalable sensing system 300. Sensing system 300 includes a plurality of sensors 320A-N. As described below in more detail, sensors 320A-N can be image sensors, photon detection sensors, chemically sensitive sensors, transmembrane sensors, quanta CMOS image sensors (QISs) and/or other types of sensors used for performing biological or chemical analysis. In a similar manner as described above, sensors 320A-N can be pre-fabricated or disposed on packaged semiconductor dies that are diced from a semiconductor wafer or wafer-level packaged semiconductor wafer as a group. In some embodiments, sensing system 300 can further include a fluidic reaction channel 302, an optical system 304, and a signal and data processing system 330. In some embodiments, fluidic reaction channel 302, sometimes also referred to as sample channel 302, is configured to exchange liquid reagent for analyzing biological or chemical samples. For example, in a DNA sequencing analysis, sequencing samples can be disposed in sequencing reagents flowing through fluidic reaction channel 302. In some embodiments, optical system 304 can be configured to perform various functions including providing an excitation light (e.g., a laser light), guiding or directing the excitation light to the samples under analysis, and/or guiding or directing light emitted from the samples to sensors 320A-N (e.g., fluorescence or chemiluminescence light). Optical system 304 can be optional depending on the specific type of sensors and/or applications. In some embodiments, fluidic reaction channel 302 and optical system 304 can be disposed across multiple image sensors 320A-N in a throughput-scalable sensing system.

Figure 4A:
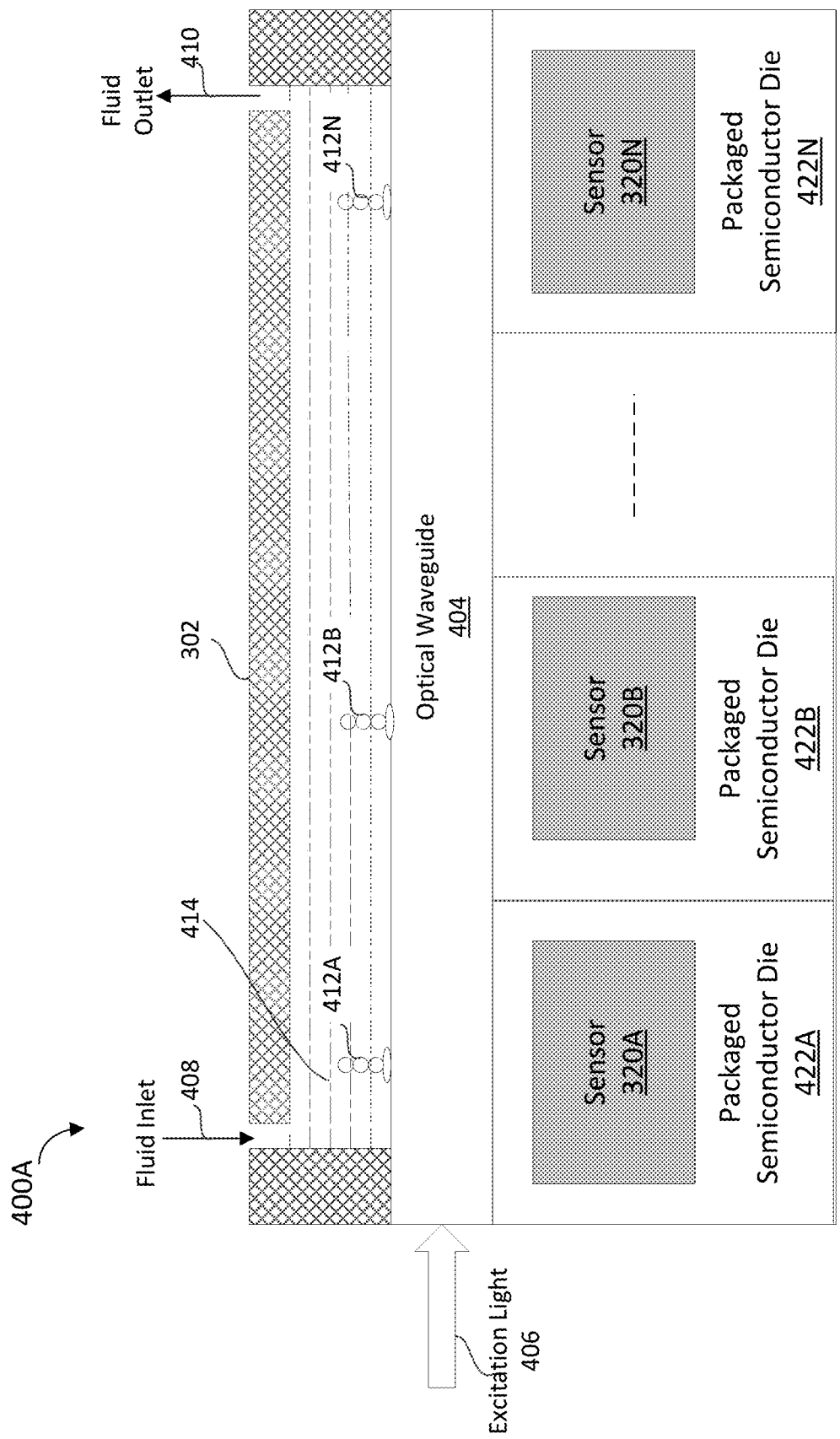
FIG. 4A is a cross-sectional view illustrating an exemplary fluidic reaction channel and a waveguide-based optical system disposed across multiple sensors in a throughput-scalable image sensing system.

FIG. 4A is a cross-sectional view illustrating an exemplary fluidic reaction channel 302 and an optical waveguide 404 disposed across a plurality of sensors 320A-N in a throughput-scalable image sensing system 400A. In FIG. 4A, a plurality of sensors 320A-N is pre-fabricated or disposed on a plurality of packaged semiconductor dies 422. Packaged semiconductor dies 422 are diced from a single semiconductor wafer or a wafer-level packaged semiconductor wafer as a group in a similar manner as described above. As shown in FIG. 4A, because packaged dies 422A-N are diced from the semiconductor wafer or a packaged wafer as a group, the upper surfaces of packaged dies 422A-N can be approximately or substantially flat across packaged dies 422A-N. This is because the surface of a semiconductor wafer or a wafer-level packaged wafer is typically flat or substantially flat. The approximately or substantially flat surfaces across multiple packaged semiconductor dies 422 enable easy disposing of optical waveguide 404 and/or fluidic reaction channel 302 across multiple dies. Optical system 404 can be part of optical system 304 shown in FIG. 3. In some embodiments, as illustrated in FIG. 4A, optical waveguide 404 can be disposed across multiple packaged semiconductor dies 422A-N. Optical waveguide 404 can include an approximately or substantially flat surface in contact with the upper surfaces of plurality of packaged semiconductor dies 422A-N on which image sensors 320A-N are arranged or disposed. In turn, fluidic reaction channel 302 can be disposed above optical waveguide 404. Fluidic reaction channel 302 can include an approximately or substantially flat surface in contact with optical waveguide 404. As shown in FIG. 4A, in some embodiments, fluidic reaction channel 302 can include a fluid inlet 408 and fluid outlet 410. Liquid reagent 414 can be directed to flow into channel 302 from fluid inlet 408 and flow out of channel 302 from fluid outlet 410.

In some embodiments, optical waveguide 404 is configured to deliver an excitation light 406 along its longitudinal direction. For example, optical waveguide 404 may include one or more light-guiding layers (e.g., two cladding layers and an optical core layer) that direct excitation light 406 to illuminate biological or chemical samples 412 disposed inside fluidic reaction channel 302. In some embodiments, fluidic reaction channel 302 can operate as a part of optical waveguide 404 (e.g., operating as the optical core layer of optical waveguide 404). Thus, in some embodiments, fluidic reaction channel 302 and one or more light-guiding layers may be collectively referred to as optical waveguide 404. Excitation light 406 can be generated by a light source, which can include a laser or a light-emitting diode (LED) based light source that generates and emits excitation light 406. Excitation light 406 can be, for example, a green light (e.g., a light having wavelength in the range of about 520-560 nm) or any other desired light having a desired wavelength or wavelength range. The light source that generates excitation light 406 can be, for example, a diode laser or LED. Details of the optical waveguide 404, fluidic reaction channel 302, and excitation light 406 are further described in International Application No. PCT/CN2019/087455, entitled "ANALYTICAL SYSTEM FOR MOLECULE DETECTION AND SENSING," filed on May 17 2019, the content of which is incorporated by reference in its entirety for all purposes.

As illustrated in FIG. 4A, because packaged semiconductor dies 422A-N (on which image sensors 320A-N are arranged) are diced as a group from a same wafer-level packaged semiconductor wafer, the surfaces of packaged semiconductor dies 422A-N are approximately or substantially flat. The flatness of the surfaces across the packaged semiconductor dies diced from a same semiconductor wafer as a group enables easy sharing or disposing of a single optical waveguide (e.g., waveguide 404) and a single fluidic reaction channel (e.g., channel 302) across multiple sensors 320A-N of a throughput-scalable sensing system. Such a sharing may not be practical or possible in traditional sensing systems. As described above, a traditional image sensor (e.g., image sensor 102 shown in FIG. 1) is packaged using a wire bonding based method. As a result, bonding wires and epoxy for protecting the bonding wires may render the surface of the image sensor uneven. The uneven surface makes it difficult, impractical, or impossible to share optical waveguide and fluidic reaction channel across multiple image sensors. The uneven surface of an image sensor may also negatively impact the performance of the fluidic reaction channel, because some portions of the channel may need to be curved/shaped due to the uneven surface of the image sensor. A curved fluidic reaction channel restricts or limits the fluid flow inside the channel. As described in more detail below, the group dicing technology described in this disclosure can further be combined with through-silicon via (TSV) and redistribution layer (RDL) technologies to provide signal redistribution for reducing, avoiding, or replacing the need for wire bonding. As described in more detail below, the TSV packaged semiconductor dies can maintain approximately or substantially flat surfaces across multiple semiconductor dies for enabling sharing or disposing of a single optical waveguide (e.g., waveguide 404) and a single fluidic reaction channel (e.g., channel 302) across multiple sensors 320A-N of a throughput-scalable sensing system.

With reference to FIG. 4A, in some embodiments, samples 412A-N (e.g., clusters of biological or chemical samples) can be disposed at positions corresponding to sensors 320A-N, respectively. For example, sample 412A is disposed above sensor 320A and is physically aligned with sensor 320A; sample 412B is disposed above sensor 320B and is physically aligned with sensor 320B; and so forth. The light emitted from samples 412A-N disposed in fluidic reaction channel 302 can be detected by corresponding sensors 320A-N. Because samples 412A-N and corresponding sensors 320A-N are aligned with each other, respectively, the light collection efficiency of sensors 320A-N can be improved or maximized. Based on the group dicing technology described above, multiple sensors 320A-N can form a throughput-scalable sensing system, effectively increasing the throughput capacity of the sensing system. While FIG. 4A illustrates that sensors 320A-N are arranged as a one-dimensional array, it is appreciated that they can be arranged as a two-dimensional array of any size (e.g., 3×3, 6×6, 10×10, etc.).

Figure 4B:
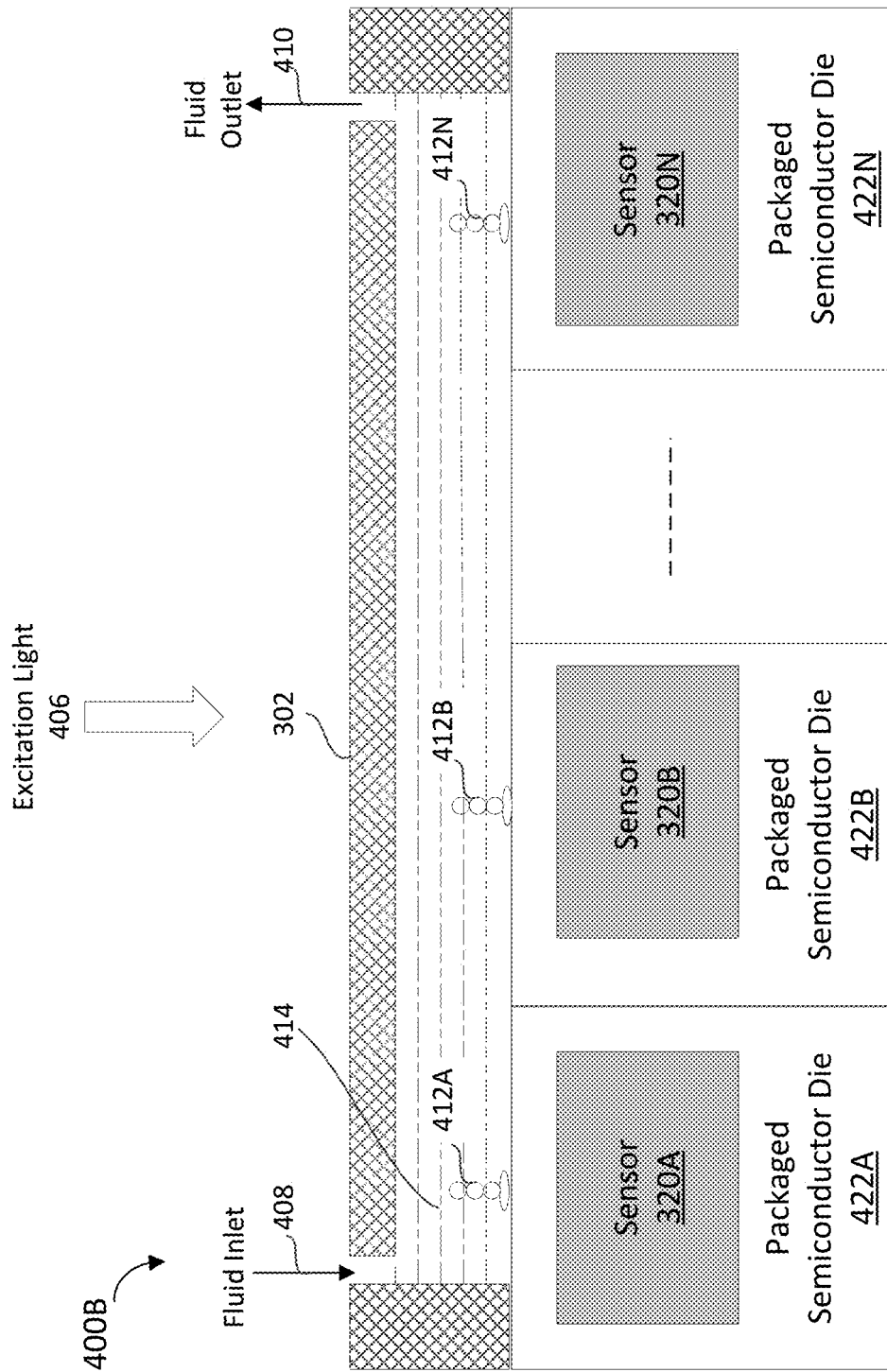
FIG. 4B is a cross-sectional view illustrating an exemplary fluidic reaction channel with direct illumination across multiple sensors in a throughput-scalable image sensing system.

In some embodiments, excitation light 406 may not be delivered using optical waveguide 404 as illustrated in FIG. 4A. Instead, excitation light 406 can be guided to directly illuminate samples 412A-N, as illustrated in FIG. 4B. FIG. 4B is a cross-sectional view illustrating an exemplary fluidic reaction channel 302 with direct illumination across a plurality of sensors 320A-N in a throughput-scalable image sensing system 400B. System 400B can be configured to be substantially the same as system 400A except that system 400B does not include an optical waveguide for directing excitation light 406. For example, to illuminate samples 412A-N in system 400B without using an optical waveguide, excitation light 406 can be guided to provide illumination to samples 412A-N from above fluidic reaction channel 302, as shown in FIG. 4B. Excitation light 406 can be guided using, for example, focused lens, filters, and/or any other desired optical elements.

With reference back to FIG. 3, based on the detection of light emitted from samples disposed in fluidic reaction channel 302, multiple sensors 320A-N can generate and transmit electrical signals to a signal and data processing system 330 for further signal and data processing. As a result, data generated for samples disposed in the fluidic reaction channel 302 can be processed in parallel in a large scale. Data generated for many samples can be processed concurrently, in substantially the same time, or in a short time period. The capability of concurrent or parallel processing of data improves the testing throughput and speed over conventional analytical systems. Further, as discussed above, the group dicing technology enables the image sensing system to be easily scaled or stacked up to provide parallel signal and data processing in a large-scale image sensing application (e.g., 100 meg-1 giga imaging application). For example, 20 image sensors can provide 20 times more image sensing area due to the increased number of photosensitive elements (e.g., pixels) included in the 20 image sensors. If each image sensor has 100 meg pixel array size, 20 image sensors would have 2000 meg or 2 giga pixels, thereby greatly improving the throughput capacity and analysis speed. Further, such a scaling of the sensing system does not require complex system re-design associated with traditional methods for providing a high-throughput sensing system. For example, in some embodiments, each sensor 320A-N can have its own amplifier, filter, and/or associated shutter and readout circuitry, and can be electrically isolated from other sensors. Thus, the re-design effort for sensors 320A-N and their associated signal processing circuitry can be significantly reduced or minimized.

A throughput-scalable image sensing system obtained based on the group dicing technology described in this disclosure can be particularly useful for many applications involving photon counting. Such applications include, for example, analysis of biological or chemical samples using light emitted from the samples. For example, based on the photons collected and detected by multiple image sensors in a high-throughput image sensing system, multiple nucleotide acid sequencing processes can be concurrently performed. Further, for sample analysis applications such as nucleotide acid sequencing applications, an image sensing system (e.g., system 300) is required to perform photon counting and generate an image based on the results of photon counting. The image thus generated may represent certain information (e.g., photon intensity) associated with the sample analysis. But such an image may not be required to be a continuous image or may be allowed to have gaps between different portions of the image. A sensing system obtained based on group dicing of multiple dies may generate image with gaps.

With reference to back to FIG. 2C, multiple image sensors are disposed on packaged semiconductor dies 222A-F. As illustrated in FIG. 2C, photosensitive elements of the multiple image sensors are not physically continuous or connected with one another. For example, photosensitive elements 224 of the image sensor disposed on die 222A are physically separated from photosensitive elements 234 of the image sensor disposed on die 222B. Between the photosensitive elements of different image sensors, other device structures or components (e.g., pads 226) and dicing streets (e.g., dicing street 235 between dies 222A and 222B) may exist. As a result, an image generated by multiple image sensors disposed on separate packaged semiconductor dies 222A-F may not be continues or may have one or more image gaps between different portions of the image. Image gaps can be blank or dark areas between different portions of an image due to the lack of photon sensing between the photosensitive elements. Such image gaps may not be acceptable for certain imaging applications that require a continuous image to be provided. Such applications may include, for example, traditional photo-capturing applications (e.g., taking portrait photos, picturing a real-world object, etc.), surveillance camera applications, or security monitoring applications.

Further, for those applications in which image gaps are not acceptable or tolerable, if a raw image generated by multiple image sensors is not continues or has image gaps, significant image processing efforts may be required to remove or mitigate the image gaps. For example, post-capturing image processing may be applied to stitch portions of the images together to provide an acceptable image without image gaps. Thus, an image sensing system with multiple image sensors that have discretely-positioned photosensitive elements (e.g., elements that are not physically continuous or connected with one another) may not be easily designed or implemented for certain imaging applications. In contrast, such an imaging system may not have or may have minimum impact on performance of a biological or chemical sample analysis application such as a nucleotide acid sequencing application. For many biological or chemical sample analysis applications, the image sensors are used to count photons emitted from the samples and generate an image base on the photons. The image can be allowed to have image gaps, because the analysis results can be derived based on the information related to photon detections (e.g., the intensity of photons, position of photons, pattern of photons, etc.). The derivation of the analysis results does not require the image to be continuous or without image gaps. Therefore, a high-throughput image sensing system including multiple image sensors obtained based on group dicing technologies can be readily used for many biological or chemical sample analysis application or any other photon counting based applications, without requiring any mitigation effort to remove the image gaps caused by the discretely-positioned photosensitive elements.

With reference back to FIG. 3, sensors 320A-N can be different types of image sensors, such as back-side illumination based image sensors or front-side illumination based sensors. As described above, because image sensors necessarily detect photons, they are sometimes also referred to as, or used as, photon detection sensors, photon counting sensors, or photoelectron counting sensors. In addition, while the above description with respect to FIG. 3 use image sensors as examples, sensors 320A-N can also be other type of sensors such as chemically sensitive sensors, transmembrane pores based sensors, photon detection sensors, photon counting sensors, and/or quanta CMOS image sensors (QIS). These types of sensors are each described in more detail below. Further, it is appreciated that blocks in FIG. 3 are for illustration purposes and not for defining the boundary of devices. For example, one or more components, devices, or subsystems of signal and data processing system 330 may be integrated or combined with sensors 320A-N, and vice versa.

Figure 5A:
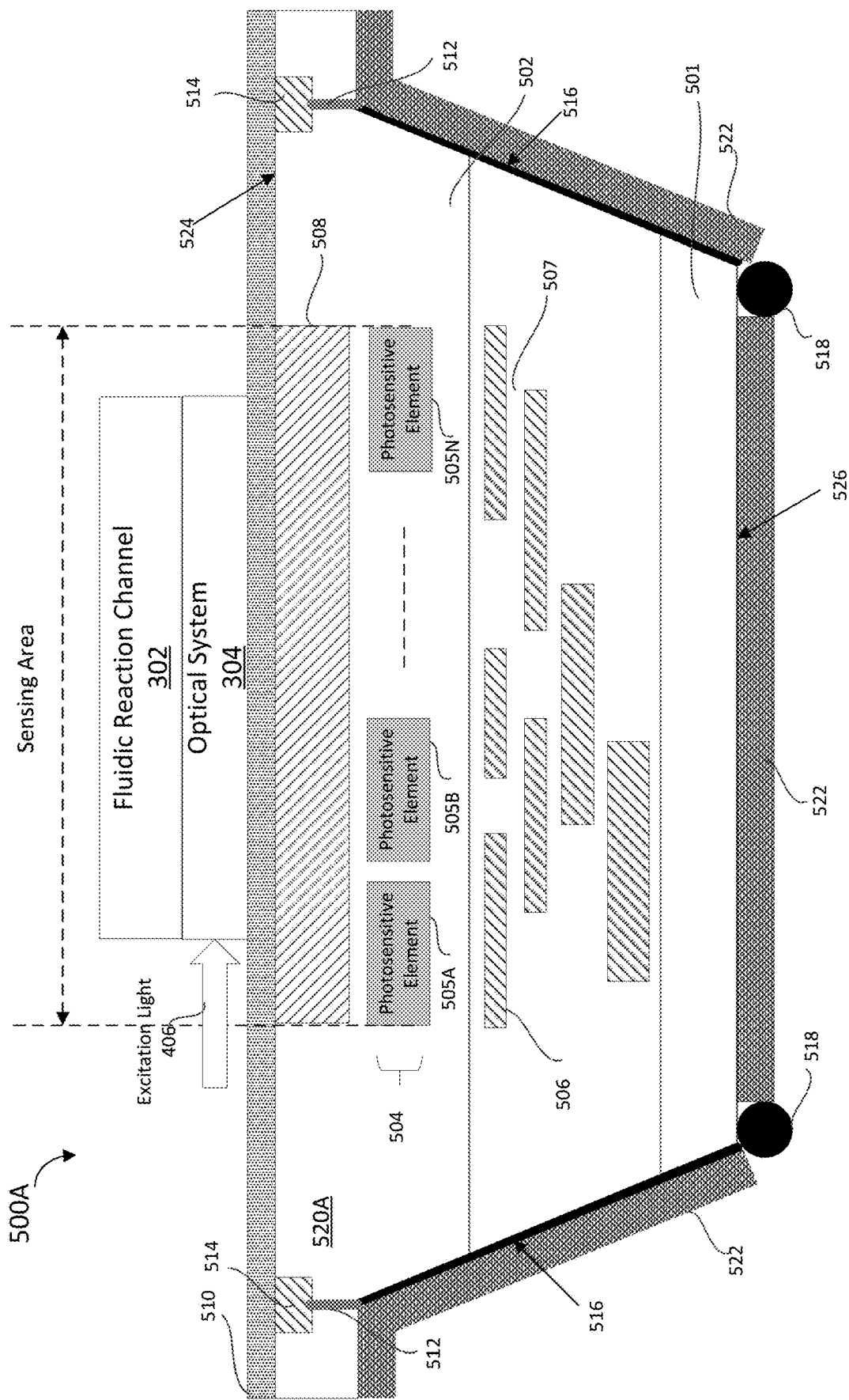
FIG. 5A illustrates an exemplary image sensing system with a cross-sectional view of an embodiment of a TSV packaged back-side illumination (BSI) based image sensor.

FIG. 5A illustrates an embodiment of an image sensing system 500A with a cross-sectional view of an embodiment of a TSV packaged BSI-based image sensor 520A. Image sensor 520A can be one embodiment of one or more of sensors 320A-N as shown in FIG. 3. As shown in FIG. 5A, image sensor 520A includes a semiconductor substrate 502, on which integrated circuits or devices can be fabricated or disposed. Semiconductor substrate 502 can be, for example, a silicon-based substrate for enabling the integrated circuits or devices to be fabricated using complementary metal-oxide semiconductor (CMOS) processes. Image sensor 520A can further include a photon detection layer 504, one or more conductive layers 506, one or more dielectric layers 507, and a filter 508. In some embodiments, photon detection layer 504 includes a plurality of photosensitive elements 505A-N (collectively as photosensitive elements 505). Each photosensitive element 505 may also be referred to as a pixel. And the plurality of photosensitive elements 505 may form a pixel array. In some embodiments, photosensitive elements 505 can include, for example, photodiodes (e.g., silicon-based photodiodes) and amplifiers, for detecting photons and generating electrical signals (e.g., photoelectrons) based on detected photons. Similar to those described above with respect to FIGS. 3 and 4A, a fluidic reaction channel (e.g., channel 302) and an optical system (e.g., system 304) may be disposed above image sensor 520A. To obtain fluorescence light, for example, the optical system can be an optical waveguide that delivers an excitation light to the samples disposed in the fluidic reaction channel. In some embodiments, the optical system does not include an optical waveguide. Instead, the optical system can include focus lens, optical filters, and/or any other desired optical elements for providing illumination from above fluidic reaction channel 302 (similar to that shown in FIG. 4B). The light emitted as a result of analyzing the biological or chemical samples disposed in the fluidic reaction channel may be detected by the photosensitive elements 505 of photon detection layer 504. Based on detected photons, the photosensitive elements 505 of the photon detection layer 504 generate electrical signals (photoelectrons). While FIG. 5A illustrates one image sensor 520A, it is appreciated that multiple image sensors can be included in image sensing system 500A. The multiple image sensors can be configured similar to that shown in FIG. 4A or 4B.

With reference to FIG. 5A, image sensor 520A illustrates an embodiment of a back-side illumination (BSI) based image sensor structure. In a BSI-based image sensor, the photon detection layer 504 are disposed closer to the samples under analysis than to the conductive layers 506. As shown in FIG. 5A, fluidic reaction channel 302, or a portion thereof, can be disposed above photon detection layer 504 (and above the filter 508, optional passivation layer 510, and/or optical system 304). Therefore, the biological or chemical samples disposed inside fluidic reaction channel 302 are positioned further to conductive layers 506 than photon detection layer 504 in the vertical direction. Thus, in a BSI-based image sensor, the light emitted from the samples travels to photon detection layer 504 without having to traveling through multiple conductive layers 506. As a result, the distance of light traveling in an BSI-based image sensor is shorter compared to that of an FSI-based image sensor. BSI-based image sensors can thus greatly reduce the signal loss and cross talk due the shorter distance that the light emitted from the samples has to travel. The shorter distance of light traveling in an BSI-based image sensor also eliminates or reduces the need for additional fluorescence or chemiluminescence light collection optics. Further, by eliminating the multiple conductive layers in the light path, a substantial or entire area of photosensitive elements 505 of photon detection layer 504 can have access or be sensitive to the light emitted from the samples. A BSI-based image sensor can thus reduce light absorption compared to an FSI-based image sensor. In some embodiments, the quantum efficiency of a BSI-based image sensor can be improved (e.g., by 80-90%) comparing to an FSI-based image sensor. Reducing signal loss and having higher quantum efficiency in turn improves image quality and resolution, and reduces the need for a highly-sensitive image sensor.

As illustrated in FIG. 5A, the electrical signals, or photoelectrons, generated by photon detection layer 504 can be collected and conducted by the plurality of conductive layers 506. Conductive layers 506 can include one or more layers of metal layers and vias interconnecting the metal layers. Conductive layers 506 are configured to electrically couple the photosensitive elements 505 to one or more electrically-conductive pads 514. For example, conductive layers 506 can transmit the electrical signals generated by the photosensitive elements 505 of photon detection layer 504 to one or more electrically-conductive pads 514. In some embodiments, the electrical signals generated by the photosensitive elements 505 may be further processed before they are transmitted to electrically-conductive pads 514. For example, conductive layers 506 can be part of a signal amplification, readout, and/or conversion circuitry (not shown). These signal amplification, readout, and/or conversion circuitry are collectively referred to as the signal processing circuitry, which can be part of signal and data processing system 330 shown in FIG. 3. In some embodiments, the signal processing circuitry can include, for example, avalanche amplification circuitry, an in-pixel readout circuit, a correlated double sampling (CDS) circuit, a sense amplifier, and/or an analog-to-digital (ADC) conversion circuit. In some embodiments, one or more of the signal amplification, readout, and/or conversion circuitry are implemented for each photosensitive element 505 (e.g., each pixel) or shared across multiple photosensitive elements 505 (e.g., shared by each readout cluster) of photon detection layer 504. For instance, each image sensor fabricated or disposed on a semiconductor die can have its own signal processing circuitry, which processes the electrical signals generated by the particular image sensor independently from other image sensors. This enables parallel or concurrent processing of electrical signals of multiple image sensors, thereby improving the overall throughput of the image sensing system.

In some embodiments, one or more of the signal amplification, readout, and/or conversion circuitry can be implemented in the same semiconductor die or wafer as the photosensitive elements 505. In some embodiments, one or more of the signal amplification, readout, and/or conversion circuitry can be implemented in a different semiconductor die or wafer than that for the photosensitive elements 505. For example, as described in more detail below, a first semiconductor wafer (also referred to as a detection wafer) can be configured to implemented photosensitive elements 505 (e.g., photodiodes) and a second semiconductor wafer (also referred to as an ASIC wafer) can be configured to implement a signal processing system including the readout circuitry. Electrical coupling between the two semiconductor wafers can use, for example, wafer-level packaging techniques such as wafer bonding and TSV techniques. As a result, the detection wafer can include many more photosensitive elements due to the extra wafer area made available by disposing signal processing circuitry in another wafer, thereby further improving throughput of the image sensing system.

With reference to FIG. 5A, image sensor 520A can further include a filter 508 and an optional passivation layer 510. Filter 508 can be disposed between optical system 304 (e.g., an optical waveguide) and photon detection layer 504. In some embodiments, filter 508 can be configured to remove a substantial portion of light having a first wavelength range. The first wavelength range is different from one or more wavelength ranges associated with the light emitted as a result of analyzing the biological or chemical samples disposed in fluidic reaction channel 302. For example, filter 508 can include a coating deposited on photon detection layer 504 for removing a substantial portion of scattered or leakage light in the wavelength range of the excitation light (e.g., green light), while allowing a substantial portion of the light emitted from the samples to pass (e.g., yellow light and/or red light). Thus, filter 508 can improve the signal-to-noise ratio by allowing desired light signals to reach photon detection layer 504 while blocking undesired light signals (e.g., background noise and/or excitation light leakage). In some embodiments, filter 508 can be a different type of coating deposited on photon detection layer 504 such that a plurality of filter cells of the filter 508 is interleaved (e.g., forming a chessboard pattern separating different types of cells by a grid structure) to reduce crosstalk between adjacent photosensitive elements 505 (e.g., adjacent pixels) of the photon detection layer 504. Crosstalk is often undesired because the light emitted from one sample can be affected by the light emitted from another sample, resulting in signal distortion for some photosensitive elements 505 (e.g., pixels) of an image sensor. Filter 508 can remove, for example, a substantial portion of all lights (e.g., absorb lights in all wavelength ranges or any desired wavelength ranges). Thus, by interleaving filter cells of filter 508, crosstalk can be reduced or eliminated.

In some embodiments, image sensor 520A can include a passivation layer 510. In some embodiments, passivation layer 510 can be a polymer coating with low refractive index or a silicon dioxide layer. Passivation layer 510 can effectively separate fluidic reaction channel 302 from other layers or devices of image sensor 500, such that other layers or devices are protected from liquid and/or mechanical damage. For example, passivation layer 510 can protect the photosensitive elements 505 of photon detection layer 504, conductive layers 506, and/or signal processing circuitry (not shown) from liquid and/or mechanical damage.

As described above, by including multiple image sensors disposed on packaged semiconductor dies that are obtained based on the group dicing technology, a throughput-scalable image sensing system can be provided. Such a system can be scaled to have high throughput (e.g., millions or billions of image pixels). Such a high-throughput system also does not require traditional wire bonding techniques to transmit electrical signals from the image sensors to external circuitry. Wire bonding techniques may be associated with many disadvantages or drawbacks as described above, and in particular, may impose difficulties in a high throughput image sensing system that has large or high-density pixel arrays. In some embodiments, through-silicon vias (TSV) and redistribution layer (RDL) routing technologies can be used in combination with the group dicing technology to obtain a high-throughput image sensing system. In FIG. 5A, the plurality of conductive layers 506 electrically couples the photosensitive elements 505 of photon detection layer 504 to one or more electrically-conductive pads 514. For example, a top metal layer (e.g. metal layer 4) may be physically routed to pads 514. Thus, the electrical signals generated by the photosensitive elements 505 of photon detection layer 504, or processed signals (e.g., amplified, sensed, converted signals), can be transmitted to pads 514.

As shown in FIG. 5A, pads 514 can be disposed at a surface 524 of the semiconductor die on which image sensor 520A is fabricated or disposed. Surface 524 can be a surface of the semiconductor die with or without passivation layer 510. In some embodiments, surface 524 can be a back surface of a die (e.g., the surface at or near which no conductive layers for signal routing is disposed), or a back surface of a die with reduced thickness (e.g., a thinned back surface of a semiconductor die). As illustrated, fluidic reaction channel 302 (or a portion thereof) and optical system 304 (or a portion thereof) may be disposed above image sensor 520A and in particular on surface 524 (or on passivation layer 510). As described above, fluidic reaction channel 302 and optical system 304 can be disposed across multiple semiconductor dies on which image sensors are fabricated or disposed. Therefore, coupling electrically-conductive pads 514 to external circuitry using bonding wires may be difficult or impractical because the bonding wires would interfere with the disposing of fluidic reaction channel 302 and/or optical system 304.

In some embodiments, image sensor 520A can include one or more through-hole vias 512. Through-hole vias 512 may be through-silicon vias formed by anisotropic or directional etching (e.g., dry etching) of semiconductor substrate 502 near the areas of pads 514. Through-hole vias 512 can form a channel or pipe that cuts through the a portion or entire thickness of semiconductor substrate 502 at or near the areas of pads 514. Subsequently, a redistribution layer (RDL) 516 can be deposited for signal re-routing. An RDL is an extra conductive layer (e.g., metal layer) that renders input/output pads (e.g., pads 514) of an integrated circuit or device available in other locations. In some embodiments as shown in FIG. 5A, RDL 516 can include conductors at least partially enclosed by through-hole vias 512. The conductors of RDL 516 further extends from pad 514 to one or more electrically-conductive spheres 518. Spheres 518 can be, for example, solder balls. RDL 516 electrically couples pads 514 to spheres 518, thereby rerouting the electrical signals from pads 514 to spheres 518. Spheres 518 can be disposed at a surface 526. In some embodiments, surface 526 can be a processed substrate surface (e.g., a thinned surface) of another semiconductor die or wafer. For example, as described in more detail below, a carrier wafer can be bonded to the wafer on which the image sensors are disposed or fabricated. The substrate of the carrier wafer can be thinned. Substrate 501 shown in FIG. 5A illustrates such a thinned portion of the carrier wafer. And thus surface 526 is a thinned surface of substrate 501 of the carrier wafer. In some embodiments, no carrier wafer is used and therefore surface 526 can be, for example, a front surface of a semiconductor die (e.g., the surface at or near which conductive layers 506 for routing signals are disposed).

As illustrated in FIG. 5A, using through-hole vias 512 and RDL 516, electrical signals can be re-routed from first surface 524 of the semiconductor die to second surface 526. Further signal routings or coupling can thus be rendered at second surface 526 using electrically-conductive spheres 518. For instance, wafer level packaging or bonding can be performed such that a first wafer (e.g., a detection wafer) comprising multiple image sensors can be electrically coupled to a second wafer (e.g., a signal processing wafer or ASIC wafer) using the electrically-conductive spheres 518. The TSV and RDL technologies thus eliminate the need for traditional wire bonding techniques for routing signals, and can further enable the implementation of a high throughput or throughput-scalable image sensing system.

With reference to FIG. 5A, in some embodiments, a solder mask layer 522 can be disposed between two neighboring spheres 518. Solder mask layer 522 can be disposed in contact with at least a portion of semiconductor substrate 501 and in contact with at least a portion of RDL 516. Solder mask layer 522 can be, for example, a layer of polymer or epoxy that is applied to a surface to protect again oxidation of an underlying conductive layer (e.g., RDL 516) or to prevent solder bridges from forming between closely spaced electrically-conductive spheres (e.g., two neighboring spheres 518).

Figure 5B:
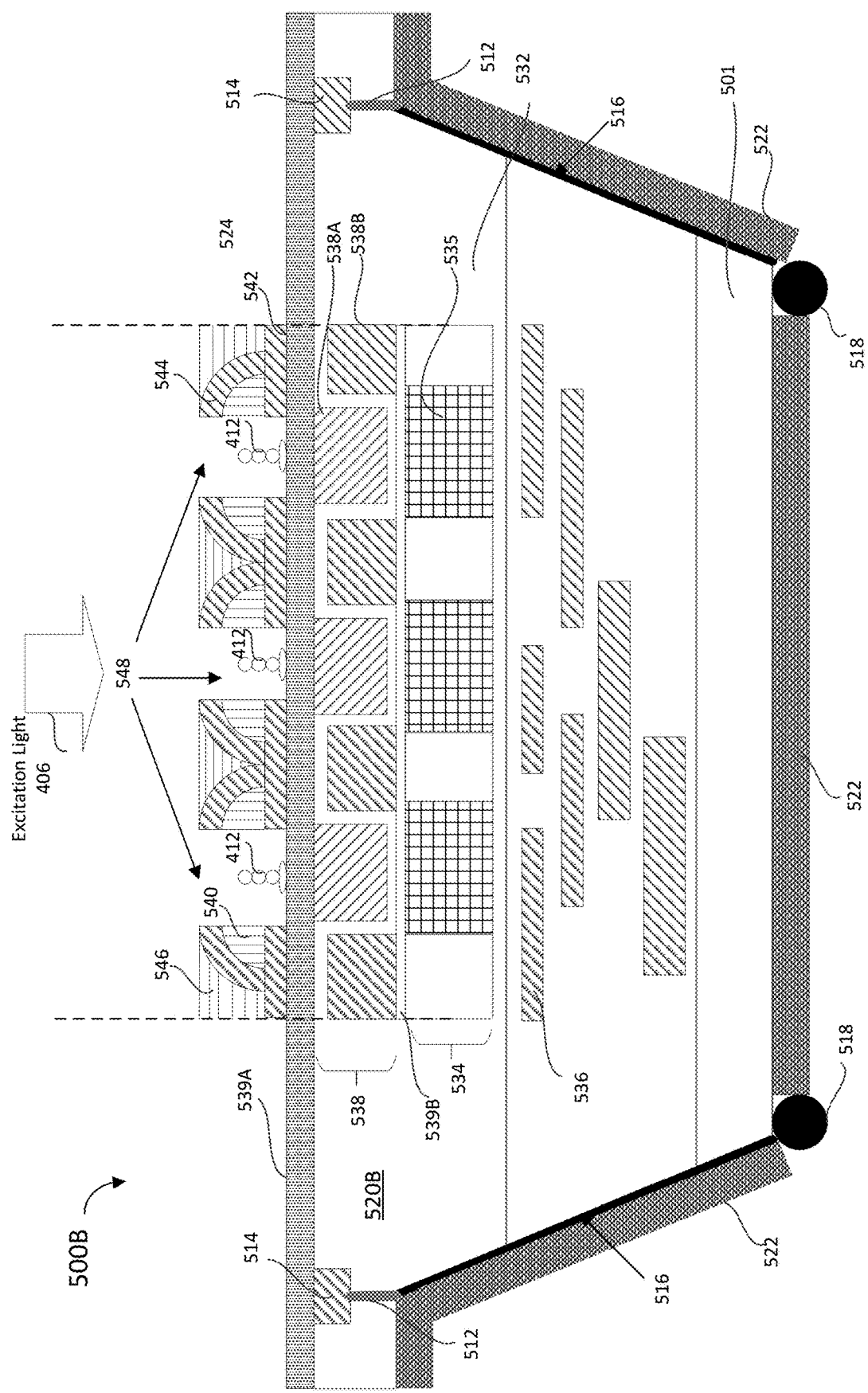
FIG. 5B illustrates an exemplary image sensing system with a cross-sectional view of another embodiment of a TSV packaged BSI-based image sensor.

FIG. 5B illustrates an exemplary image sensing system 500B with a cross-sectional view of another embodiment of a TSV packaged BSI-based image sensor 520B. With reference to FIG. 5B, similar to image sensor 520A shown in FIG. 5A, image sensor 520B is a BSI-based image sensor including a semiconductor substrate 532, a photon detection layer 534 including a plurality of photosensitive elements 535, one or more conductive layers 536, a filter 538, and two passivation layers 539A-B. These components or layers of image sensor 520B can be the same or substantially the same as semiconductor substrate 502, photon detection layer 504, conductive layers 506, filter 508, and passivation layer 510 of image sensor 520A, respectively, and therefore are not repeatedly described.

In some embodiments, in addition to image sensor 520B, image sensing system 500B illustrated in FIG. 5B can further include a first conductive layer 542, a second conductive layer 544, a plurality of microlenses 540, and a planarization layer 546. First conductive layer 542, microlenses 540, and second conductive layer 544 can implement optical system 304 in FIG. 3. First conductive layer 542 and a second conductive layer 544 can include metal layers. Microlenses 540 can include one or more optical elements such as lens, mirrors, lens-like structures, or the like. Microlenses 540 can be made of glass, polymers, plastics, or the like. As illustrated in FIG. 5B, passivation layer 539A is disposed above and in contact with filter 538. First conductive layer 542 is disposed above and in contact with passivation layer 539A. First conductive layer 542 can be substantially flat. Second conductive layer 544 can be disposed above the first conductive layer 544 and the plurality of microlenses 540. In some embodiments, second conductive layer 544 can have a curved shape as illustrated in FIG. 5B. In some embodiments, image sensor 520B can include one or more openings 548 etched through first conductive layer 542, second conductive layer 544, the plurality of microlenses 540, and planarization layer 546. Thus, neighboring microlenses of the plurality of microlenses 540 are separated by one of openings 548. Openings 548 can be configured to receive biological or chemical samples 412 and liquid reagents. Thus, openings 548 can implement, be associated with, at least a portion of fluidic reaction channel 302 of FIG. 3.

In some embodiments, excitation light 406 can be guided or directed to samples disposed in openings 548. As a result, fluorescence light can be generated and emitted from the samples 412. In some embodiments, no excitation light is used. Samples disposed in openings 548 may emit chemiluminescence light without external excitation light. The fluorescence light and chemiluminescence light are collectively referred to as light emitted from samples 412. In some embodiments, first conductive layer 542, microlenses 540, and second conductive layer 544 can focus or direct light emitted from samples 412 to filter 538 and the underneath photosensitive elements 535 in photon detection layer 534. For example, light emitted from the samples 412 can pass through microlenses 540 and focused/collected by microlenses 540. The light that passes through microlenses 540 can be reflected by second conductive layer 544, because layer 544 has a curved shape configured to reflect light. Second conductive layer 544 can also block or partially block excitation light 546, thereby reducing the amount of undesired light traveling to filter 538.

In some embodiments, the light emitted from the samples 412 may also pass through microlenses 540 and be reflected by first conductive layer 542, and subsequently refocused or reflected (e.g., by second conductive layer 544) toward filter 508 and the underneath photosensitive elements 535 of photon detection layer 504. As a result, using first conductive layer 542, microlenses 540, and second conductive layer 544, the collection efficiency of the light emitted from the samples 412 can be improved. The requirements for a high performance filter 538 and high efficiency photon detection layer 534 can therefore be reduced or alleviated. For example, the intensity of chemiluminescence light in some biological or chemical analysis applications can be low, and therefore an improved light collection efficiency may be required to provide a good analysis result. In some embodiments, as illustrated in FIG. 5B, filter 538 can have multiple filter cells 538A disposed at positions corresponding to openings 548; and the underneath photosensitive elements 535 of photon detection layer 534 can be further disposed at areas corresponding to filter cells 538A. Therefore, the respective openings 548, filter cells 538A, and photosensitive elements 535 of photon detection layer 534 can be geometrically aligned to improve or maximize the detection of the emitted light from samples 412. In some embodiments, in filter 538, filter cells 538A are interleaved with metal 538B for further reflection or focus of emitted light toward the underneath photosensitive elements 535 of photon detection layer 534. In some embodiments, one or more optical elements or portions of microlenses 540 may be removed for disposing samples 412 in openings 548. The remaining optical elements of microlenses 540 can collect, refocus, and/or reflect emitted signals to improve collection efficiency. More details of the structure, operation, and fabrication steps of image sensor 520B can be found in International Application No. PCT/US2017/059908, entitled "BIOSENSORS FOR BIOLOGICAL OR CHEMICAL ANALYSIS AND METHODS OF MANUFACTURING THE SAME," filed on Nov. 3, 2017, the content of which is incorporated by reference in its entirety.

Similar to those described in FIG. 5A, TSV packaging and RDL technologies can be applied to image sensor 520B to provide a high-throughput or throughput-scalable image sensing system. For example, as shown in FIG. 5B, RDL 516 can be disposed to electrically couple pads 514 and spheres 518, thereby re-routing signals from pads 514 to spheres 518. Spheres 518 can be further electrically coupled to external signal processing circuitry. Further, group dicing technology can also be applied to obtain a throughput-scalable image sensing system based on image sensor 520B, such that multiple image sensors 520B are disposed on packaged semiconductor dies diced from a wafer as a group. The details of TSV packaging, RDL routing, and group dicing technologies can be applied in a similar manner as described above, and are thus not repeatedly described here. While FIG. 5B illustrates one image sensor 520B, it is appreciated that multiple image sensors can be included in image sensing system 500B. The multiple image sensors can be configured similar to that shown in FIG. 4A or 4B.

Figure 5C:
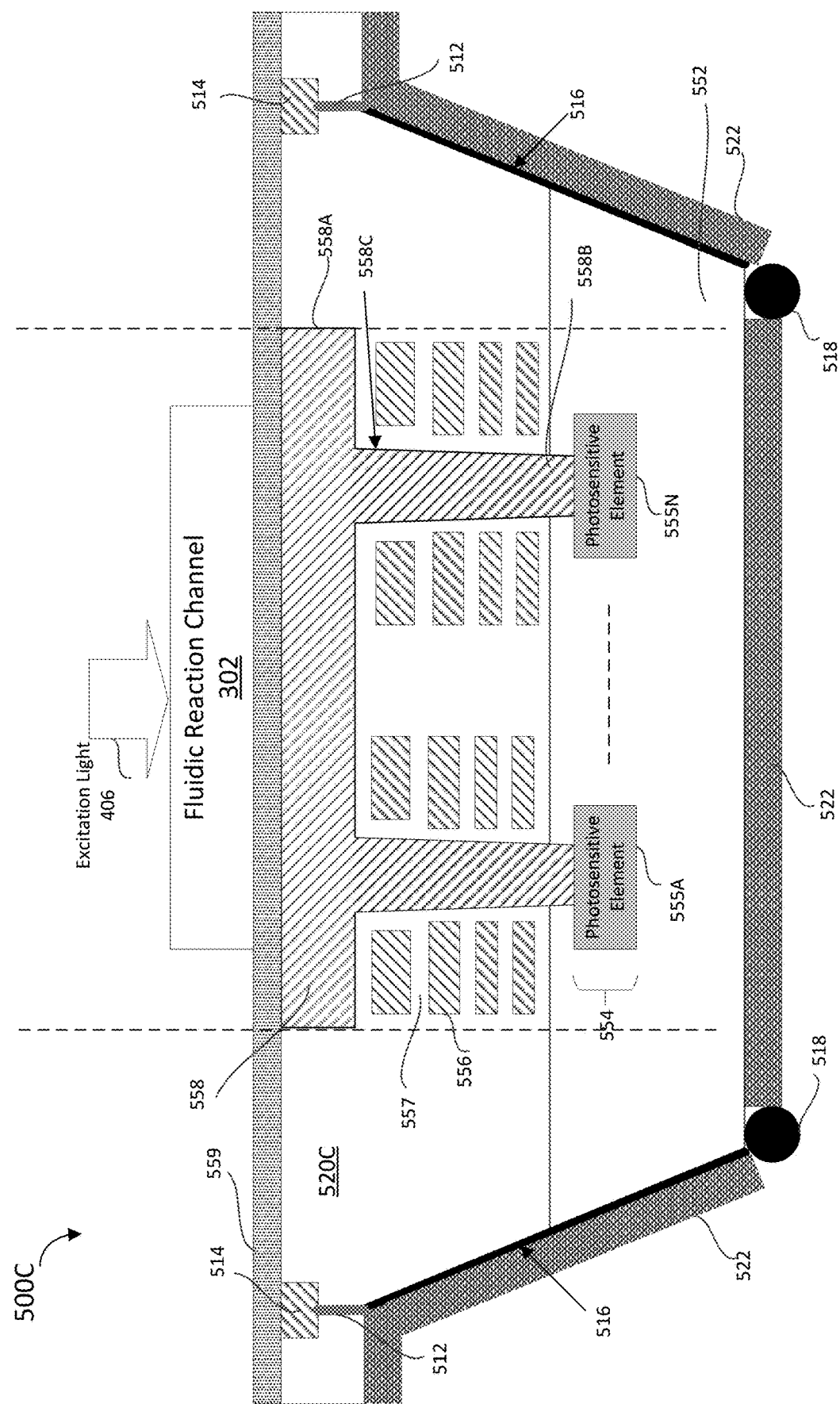
FIG. 5C illustrates an exemplary image sensing system with a cross-sectional view of an embodiment of a TSV packaged front-side illumination (FSI) based image sensor.

FIG. 5C illustrates an exemplary image sensing system 500C with a cross-sectional view of an embodiment of a front-side illumination (FSI) based image sensor 520C with TSV packaging. As described above, in a BSI-based image sensor, the light emitted from the samples travels to the photon detection layer without having to traveling through the distance of multiple conductive layers. In contrast, in an FSI-based image sensor, light emitted from samples disposed in a fluidic reaction channel typically travels through the distance of multiple conductive layers before it can reach the photon detection layer. Therefore, certain structural configurations may be required to reduce the loss of emitted light before it reaches the photon detection layer. As illustrated in FIG. 5C, similar to image sensor 520A shown in FIG. 5A, image sensor 520C includes a semiconductor substrate 552, a photon detection layer 554, one or more conductive layers 556, and a passivation layer 559. These components or layers of image sensor 520C can be the same or substantially the same as semiconductor substrate 502, photon detection layer 504, the plurality of conductive layers 506, and passivation layer 510 of image sensor 520A, respectively, and therefore are not repeatedly described.

With reference to FIG. 5C, in some embodiments, excitation light 406 can be directed or guided to samples disposed in fluidic reaction channel 302 from the top (e.g., perpendicular to the longitudinal direction of fluidic reaction channel 302) as shown in FIG. 5C. As a result of the excitation, fluorescence light is emitted from the samples disposed in fluidic reaction channel 302. In some embodiments, image sensor 520C further includes a filter 558 as shown in FIG. 5C. Filter 558 can include materials for removing a substantial portion of light having a first wavelength range. The first wavelength range is different from one or more wavelength ranges associated with the light emitted as a result of analyzing the biological or chemical samples disposed in fluidic reaction channel 302. For example, filter 558 can include light-absorbing material for removing a substantial portion of scattered or leakage light in the wavelength range of excitation light 406 (e.g., green light); while allowing a substantial portion of the light emitted from the samples to pass (e.g., yellow light and/or red light).

In some embodiments, in addition to preventing excitation light 406, or a substantial portion thereof, from reaching photosensitive elements 555A-N (collectively as photosensitive elements 555) of photon detection layer 554, filter 558 can be configured to direct or guide light emitted from samples disposed in fluidic reaction channel 302 to photosensitive elements 555 of photon detection layer 554. As described above, for an FSI-based image sensor, the distance that the emitted light travels is typically longer than that in a BSI-based image sensor, due to the thickness of the conductive layers 556 (and one or more dielectric layers 557 associated with the conductive layers 556). Filter 558 can thus be configured to reduce or minimize the loss of emitted light along the path to the photosensitive elements 555 of photon detection layer 554. As one example, filter 558 can include a flat portion 558A and one or more filter protrusions 558B. Filter protrusions 558B are configured to provide filter channels directing at least a portion of the light emitted as a result of analyzing the biological or chemical samples to the plurality of photosensitive elements 555 of photon detection layer 554. In FIG. 5C, filter protrusions 558B are configured such that their top portions (e.g., the portions that are closer to fluidic reaction channel 302) are wider than the bottom portions (e.g., the portions that are further away from fluidic reaction channel 302). As a result, wider top portions of filter protrusions 558B can improve or maximize the collection efficiency for collecting the light emitted from samples disposed in fluidic reaction channel 302. And narrower bottom portions of filter protrusions 558B can be positioned corresponding to the positions of photosensitive elements 555 of photon detection layer 554, thereby improving or maximizing the detection efficiency of the photosensitive elements 555.

In some embodiments, filter protrusions 558B can include walls 558C in contact with semiconductor substrate 552, conductive layers 556, and/or dielectric layers 557. Walls 558C of filter protrusion 558B can include, for example, reflective coatings for reflecting or directing emitted light toward photosensitive elements 555 of photon detection layer 554. The reflective coatings can include, for example, metal coatings or optical coatings. In some embodiments, one or more conductive layers 556 can be disposed or distributed around filter protrusions 558B to reduce or minimize crosstalk due to the distance that the emitted light has to travel in FSI-based image sensor 520C. Crosstalk may occur between adjacent photosensitive elements 555 (e.g., adjacent pixels) of the photon detection layer 554. Crosstalk is often undesired because the light emitted from one sample can be affected by the light emitted from another sample, resulting in signal distortion for some photosensitive elements 555 (e.g., pixels) of an image sensor. In some embodiments, the portions of conductive layers 556 distributed near or around filter protrusion 558B can remove, for example, a substantial portion of all lights (e.g., absorb lights in all wavelength ranges or any desired wavelength ranges). Thus, crosstalk can be reduced or eliminated. More details of the structure, operation, and fabrication steps of an FSI-based image sensor can be found in U.S. Patent Application Publication No. US2016/0356715, entitled "BIOSENSORS FOR BIOLOGICAL OR CHEMICAL ANALYSIS AND METHODS OF MANUFACTURING THE SAME," filed on Jun. 7, 2016, the content of which is incorporated by reference in its entirety for all purposes.

Similar to those described in FIG. 5A, TSV packaging and RDL technologies can be applied to image sensor 520C to provide a high-throughput or throughput-scalable image sensing system. For example, as shown in FIG. 5C, RDL 516 can be disposed to electrically couple pads 514 and spheres 518, thereby re-routing signals from pads 514 to spheres 518. Spheres 518 can be further electrically coupled to external signal processing circuitry. Because FIG. 5C illustrates an FSI-based image sensor 520C, pads 514 are disposed at or near a front surface of a packaged semiconductor die (e.g., the surface at or near which conductive metal layers for routing signals are disposed). And spheres 518 are disposed at or near a back surface of a packaged semiconductor die (e.g., the surface at or near which no conductive layers for routing signals is disposed or a surface). Thus, the surfaces for disposing pads 516 and spheres 518 in an FSI-based image sensor are the opposite to those in an BSI-based image sensor. Further, group dicing technology can also be applied to obtain a throughput-scalable image sensing system based on image sensor 520C, such that multiple image sensors 520C are disposed on packaged semiconductor dies diced from a wafer as a group. The details of TSV packaging, RDL routing, and group dicing technologies can be applied in a similar manner as described above, and are thus not repeatedly described here. While FIG. 5C illustrates one image sensor 520C, it is appreciated that multiple image sensors can be included in image sensing system 500C. The multiple image sensors can be configured similar to that shown in FIG. 4A or 4B.

Figure 5D:
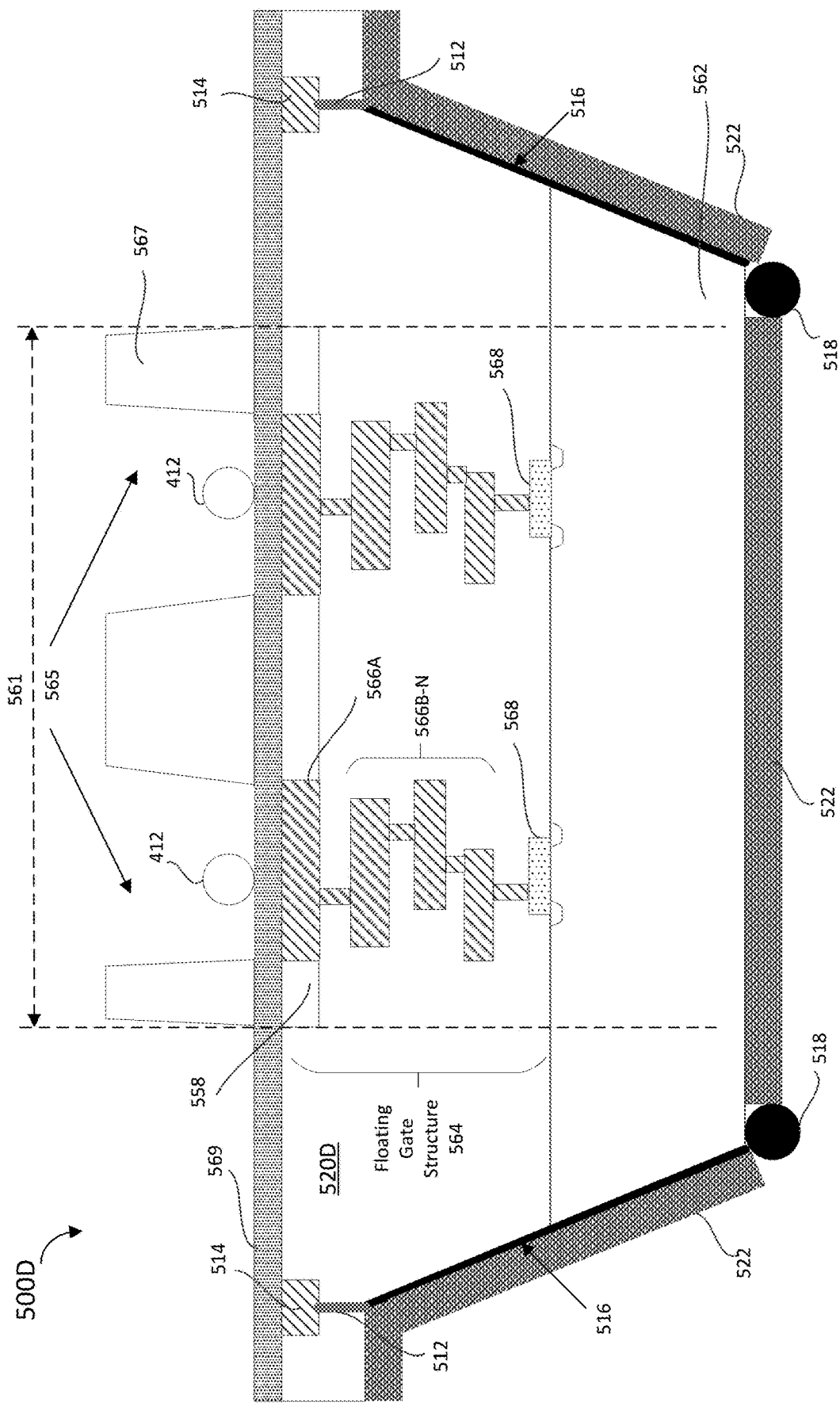
FIG. 5D illustrates an exemplary chemical sensing system with a cross-sectional view of an embodiment of a TSV packaged ion-sensitive field effect transistor (ISFET) based sensor.

With reference back to FIG. 3, in the above description, while sensors 320A-N can be implemented as image sensors (e.g., image sensors 520A-C), they can also be implemented as other types of sensors such as a chemically sensitive sensor. Thus, system 300 can be adapted to a chemical sensing system rather than an image sensing system. It is appreciated one or more blocks/components shown in FIG. 3 may not be included in a chemical sensing system; and additional blocks/components may be added to a chemical sensing system. FIG. 5D illustrates an exemplary chemical sensing system 500D with a cross-sectional view of an embodiment of a TSV packaged chemically sensitive sensor 520D.

A chemically sensitive sensor can measure certain concentrations or other chemical properties of chemical ingredients of biological or chemical samples. A chemically sensitive sensor 520D can include, for example, an ion-sensitive field effect transistor (ISFET) based sensor. An ISFET-based sensor can measure ion concertation for samples (e.g., samples 412 such as beads) disposed in liquid reagents. When the ion concentration (e.g., hydrogen ion concentration) changes, the current flowing through the ISFET changes accordingly. Thus, based on the measurement of the change of the current flow, the ion concentration of a biological or chemical sample can be determined. For instance, a chemical sensing system using ISFET-based chemical sensors can be used in nucleic acid sequencing applications such as RNA/DNA sequencing applications.

As shown in FIG. 5D, similar to image sensor 520A, chemically sensitive sensor 520D includes a semiconductor substrate 562, which is the same or substantially the same as semiconductor substrate 502 of image sensor 520A, respectively, and therefore is not repeatedly described. Chemically sensitive sensor 520D can further include a plurality of ISFETs disposed within an ISFET sensitive area 561. An ISFET includes a floating gate structure 564 disposed above semiconductor substrate 562 (e.g., a Silicon substrate). In some embodiments, floating gate structure 564 is not electrically coupled to an electrode and thus electrically "floating." In contrast, a source region and a drain region of an ISFET are electrically coupled to respective source electrode and drain electrode (not shown), respectively, and are therefore not electrically "floating." In some embodiments, floating gate structure 564 includes a first conductive layer 566A, one or more intervening conductive layers 566B-N, and a polysilicon gate 568. The first conductive layer 566A may be the topmost metal layer and the one or more intervening conductive layers 566B-N are disposed between first conductive layer 566A and polysilicon gate 568 as illustrated in FIG. 5D.

In some embodiments, chemically sensitive sensor 500D further includes a dielectric layer 569 disposed above the floating gate structure 564. Dielectric layer 569 can include at least one of silicon nitride ($Si_3N_4$), silicon oxynitride ($Si_2N_2O$), silicon oxide ($SiO_2$), aluminum oxide ($Al_2O_3$), tantalum pentoxide ($Ta_2O_5$), tin oxide or stannic oxide ($SnO_2$). In some embodiments, dielectric layer 569 can include a charge sensitive layer and an adhesion layer. Tantalum pentoxide ($Ta_2O_5$) is an example of a charge sensitive layer, and aluminum is an example of adhesion layer. In some embodiments, dielectric layer 569 can also serve as a passivation layer, as described above, for protecting chemically sensitive sensor 520D from liquid or mechanical damage. Dielectric layer 569 can be fabricated or disposed by CVD, PVD, atomic layer deposition, or the like.

In some embodiments, one or more openings or wells 565 can be fabricated or disposed above dielectric layer 569. As illustrated in FIG. 5D, wells 565 can be formed by etching an insulation layer 567 (e.g., another dielectric layer, polymer layer, or the like). In some embodiments, wells 565 can be formed at least partially inside dielectric layer 569. Wells 565 can be microwells, which has a width in the order of micrometers. In some embodiments, first conductive layer 566A includes portions that have dimensions that are substantially the same as dimensions of one or more wells 565. For instance, as shown in FIG. 5D, the width of wells 565 can be substantially the same (or slightly smaller/larger) than first conductive layer 566A, portions of which are positioned beneath wells 565 and aligned with corresponding wells 565.

In some embodiments, at least a portion of the biological or chemical samples is disposed inside the one or more wells 565. The ion concentration of biological or chemical samples 565 can be measured based on floating gate structure 564 and dielectric layer 569. In the chemical sensing system 500D, no excitation light is required because the measurement is with respect to ion concentration. Therefore, an optical system (e.g., system 304 in FIG. 3) may not be required and is not shown in FIG. 5D. In chemically sensitive sensor 520D, one of wells 565 corresponds to one of floating gate structures 564. The combination of one well and one floating structure 564 may form a single pixel of sensor 520D. Similar to those described with respect to image sensors, the more pixels in a chemically sensitive sensor, the higher the throughput capacity of the sensor.

As described above, the floating gate structure 563 is not electrically coupled to an electrode. Thus, because the samples are disposed inside wells 565 positioned above floating gate structure 564, the ion concentration in the samples disposed inside wells 565 causes a charge accumulation above the dielectric layer 569. The charge accumulation in turn changes the transistor current flowing through the source and drain areas of the ISFET. Thus, based on the transistor current change, the ion concentration can be measured. More details of the structure, operation, and fabrication steps of a chemically sensitive sensor can be found in U.S. Pat. No. 8,936,763, entitled "INTEGRATED SENSOR ARRAYS FOR BIOLOGICAL AND CHEMICAL ANALYSIS," filed on Jun. 1, 2011, the content of which is incorporated by reference in its entirety for all purposes.

Similar to those described in FIG. 5A, TSV packaging and RDL technologies can be applied to chemically sensitive sensor 520D to provide a high throughput or throughput scalable chemical sensing system. For example, as shown in FIG. 5D, RDL 516 can be disposed to electrically couple pads 514 and spheres 518, thereby re-routing signals from pads 514 to spheres 518. Spheres 518 can be further electrically coupled to an external signal processing circuitry.

Similar to the FSI-based image sensor 520C in FIG. 5C, FIG. 5D illustrates that for chemically sensitive sensor 520D, pads 514 are disposed at or near a front surface of a packaged semiconductor die (e.g., the surface at or near which conductive metal layers for routing signals are disposed). And spheres 518 are disposed at or near a back surface of a semiconductor die (e.g., the surface at or near which no conductive layers for routing signals is disposed or a surface). Further, group dicing technology can also be applied to obtain a throughput-scalable chemical sensing system based on chemically sensitive sensor 520D, such that multiple chemically sensitive sensors 520D are disposed on packaged semiconductor dies diced from a wafer as a group. The details of TSV packaging, RDL routing, and group dicing technologies can be applied in a similar manner as described above, and are thus not repeatedly described here. While FIG. 5D illustrates one chemically sensitive sensor 520D, it is appreciated that multiple chemically sensitive sensors can be included in chemical sensing system 500D. The multiple chemically sensitive sensors can be configured similar to that shown in FIG. 4A or 4B.

Figure 5E:
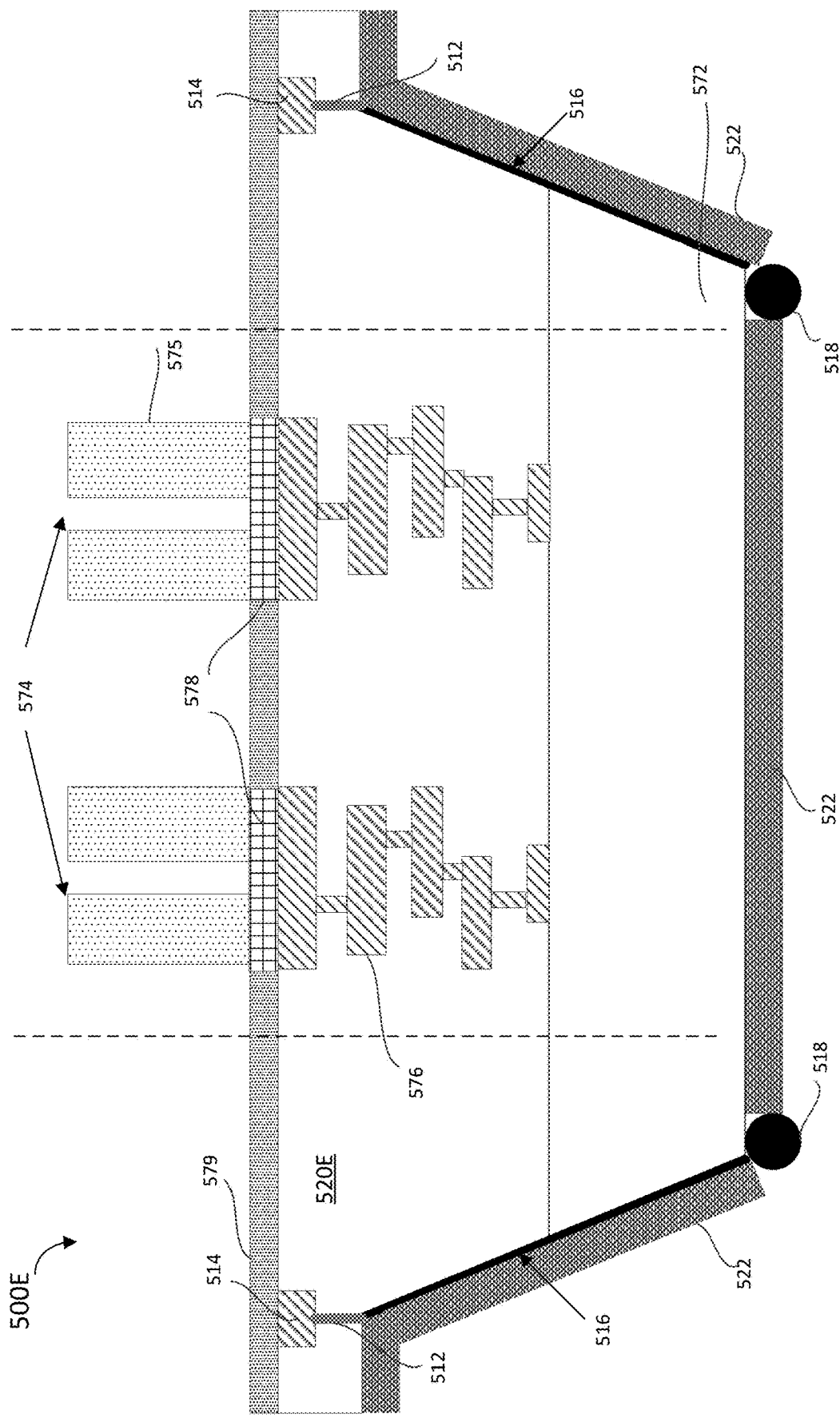
FIG. 5E illustrates an exemplary sensing system with a cross-sectional view of an embodiment of a TSV packaged transmembrane pore based sensor.

With reference back to FIG. 3, in the above description, while sensors 320A-N can be implemented as image sensors (e.g., image sensors 520A-C) or chemically sensitive sensors (e.g., chemically sensitive sensor 520D), they can also be implemented as other types of sensors such as a transmembrane pore based sensors (sometimes also referred to as nanopore based sensors). Thus, system 300 can be adapted to a sensing system using transmembrane pore based sensors. It is appreciated that one or more blocks/components shown in FIG. 3 may not be included in a transmembrane pore based sensing system; and additional blocks/components may be added to such a sensing system. FIG. 5E illustrates an exemplary transmembrane pore based sensing system 500E with a cross-sectional view of an embodiment of a TSV packaged transmembrane pore based sensor 520E.

A transmembrane pore based sensor is a type of biosensors that can detect a variety of small molecules or ions passing through the transmembrane pore. A transmembrane pore based sensor can be used in, for example, nucleic acid sequencing applications such as RNA/DNA sequencing applications. For example, in a DNA sequencing application, individual nucleotide incorporation events may be detected. Such events may include incorporation of a nucleotide into a growing strand that is complementary to a template. An enzyme (e.g., DNA polymerase) may incorporate nucleotides to a growing polynucleotide chain. The incorporated nucleotide is complimentary to the corresponding template nucleic acid strand, which is hybridized to the growing strand (e.g., polymerase chain reaction or PCR). The nucleotide incorporation events release tags from the nucleotides, which pass through a transmembrane pore and can be detected.

As illustrated in FIG. 5E, in some embodiments, transmembrane pore based sensor 520E includes a semiconductor substrate 572, one or more conductive layers 576 disposed above the semiconductor substrate 572, one or more detection electrodes 578 disposed above the semiconductor substrate 572 and conductive layers 576, and a lipid bilayer 575 disposed above detection electrodes 578. The semiconductor substrate 572 and one or more conductive layers 576 can implement integrated circuits for operation of the transmembrane pore based sensor 520E. Such integrated circuits may include, for example, amplifiers, integrators, filters, control logic, and/or other circuitry.

In some embodiments, lipid bilayer 575 can be a thin polar membrane made of two layers of lipid molecules. For example, lipid bilayer 575 can include at least one of a planar lipid bilayer, a supported bilayer, or a liposome. Lipid bilayer 575 can be a barrier that keeps ions, proteins, and other molecules where they should be and prevent them from diffusing into areas where they should not be. Lipid bilayer 575 may include, or be provided with, one or more transmembrane pores 574. Transmembrane pores 574 can include at least one of protein pores, polynucleotide pores, and solid state pores. Transmembrane pores 574 can have a dimension that is large enough for passing of molecules (e.g., tag molecules) and/or small ions (e.g., $Na^+$, $K^+$, $Ca^{2+}$, $Cl^-$) between the two sides of lipid bilayers 575. In some embodiments, a fluidic reaction channel 302 (not shown in FIG. 5E) can be disposed near or above lipid bilayer 575 to provide samples (e.g., nucleic acid molecule and tagged nucleotides in liquid reagents) to transmembrane pores 574.

In some embodiments, transmembrane pores 574 can be positioned corresponding to the positions of the one or more detection electrodes 578. Detection electrodes 578 can be coupled to an electrical source and provide electrical bias or voltage across the two sides of lipid bilayer 575, such that molecules or ions can pass through transmembrane pores 574. In some embodiments, detection electrodes 578 can further detect electrical characteristics, such as the change of ion current flow, resistance, capacitance, etc.) of lipid bilayer 575. Based on the detection of the electrical characteristics, the DNA sequence information can be derived. While FIG. 5E illustrates that detection electrodes 578 are used for both applying electrical bias or voltage across two sides of the lipid bilayers 575 and detecting the electrical characteristics of lipid bilayers 575, it is appreciated that, in some embodiments, another pair of electrodes (not shown) can be used to apply the electrical bias or voltage with detection electrodes 578 only being used for detection of the electrical characteristics. In some embodiments, as illustrated in FIG. 5E, the transmembrane pores based sensor 520E further includes a passivation layer 579. Passivation layer 579 can include one or more openings, and the detection electrodes 578 can be disposed within the one or more openings of the passivation layer 579. Similar to described above, passivation layer 579 can protect transmembrane pore based sensor 520E from liquid damage and/or mechanical damage.

In transmembrane pore based sensor 520E, one of transmembrane pores 574, its surrounding portions of lipid bilayer 575, the corresponding detection electrodes 578 disposed beneath the particular transmembrane pore 574, and the corresponding one or more conductive layers 576 may form a single pixel or sensing unit of sensor 520E. Similar to those described with respect to image sensors, the more pixels or sensing units included in a transmembrane pore based sensor, the higher the throughput capacity of the sensor. More details of the structure, operation, and fabrication steps of a transmembrane pore based sensor can be found in U.S. Patent Application Publication No. US 2015/0119259, entitled "NUCLEIC ACID SEQUENCING BY NANOPRE DETECTION OF TAG MOLECULES," filed on Oct. 8, 2014, the content of which is incorporated by reference in its entirety.

Similar to those described in FIG. 5A, TSV packaging and RDL technologies can be applied to transmembrane pore based sensor 520E to provide a high throughput or throughput scalable transmembrane pore based sensing system. For example, as shown in FIG. 5E, RDL 516 can be disposed to electrically couple pads 514 and spheres 518, thereby re-routing signals from pads 514 to spheres 518. Spheres 518 can be further electrically coupled to external signal processing circuitry. Similar to the FSI-based image sensor 520C in FIG. 5C, FIG. 5E illustrates that for transmembrane pore based sensor 520E, pads 514 are disposed at or near a front surface of a packaged semiconductor die (e.g., the surface at or near which conductive metal layers for routing signals are disposed). And spheres 518 are disposed at or near a back surface of a packaged semiconductor die (e.g., the surface at or near which no conductive layers for routing signals is disposed or a surface). Further, group dicing technology can also be applied to obtain a throughput-scalable sensing system based on transmembrane pore based sensor 520E, such that multiple transmembrane pore based sensors 520E are disposed on semiconductor dies diced from a wafer as a group. The details of TSV packaging, RDL routing, and group dicing technologies can be applied in a similar manner as described above, and are thus not repeatedly described here. While FIG. 5E illustrates one transmembrane pore based sensor 520E, it is appreciated that multiple transmembrane pore based sensors can be included in transmembrane pore based sensing system 500E. The multiple transmembrane pore based sensors can be configured similar to that shown in FIG. 4A or 4B.

Figure 5F:
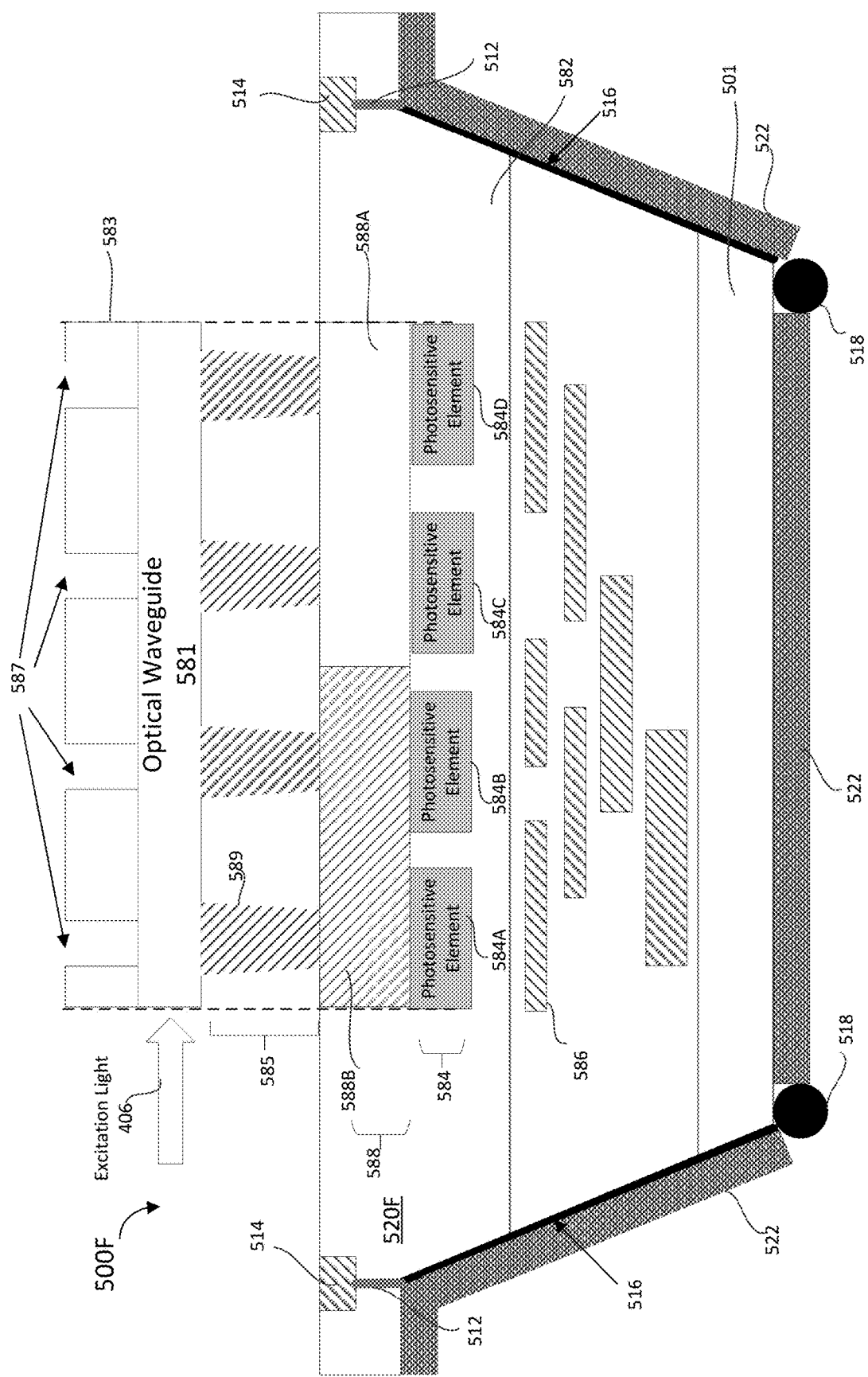
FIG. 5F illustrates an exemplary photon sensing system with a cross-sectional view of an embodiment of TSV packaged photon detection sensor capable of performing a single molecule analysis.

With reference back to FIG. 3, sensors 320A-N can be image sensors. As described above, because image sensors necessarily detect photons, they are sometimes also referred to as, or used as, photon detection sensors, photon counting sensors, or photoelectron counting sensors in this disclosure. Some photon detection sensors can be configured to be more sensitive to, or efficient in collecting, photons. For example, FIG. 5F illustrates an exemplary photon sensing system 500F with a cross-sectional view of an embodiment of TSV packaged photon detection sensor 520F capable of performing a single molecule analysis of a biological or chemical sample. One example of the single molecule analysis is a single molecule nucleic acid sequencing analysis. In such an analysis, a single immobilized nucleic acid synthesis complex is used. The synchesis complex can include a polymerase enzyme, a template nucleic acid, and a primer sequence that is complementary to a portion of the template nucleic acid. The synthesis complex is disposed as a sample and analyzed to identify individual nucleotides as they are incorporated into the extended primer sequence. The incorporation of the individual nucleotides can be monitored by detecting an optically detectable label on the nucleotide associated with an incorporation event. Unincorporated nucleotides can be removed from the synthesis complex, and the labeled incorporated nucleotides (e.g., fluorescently labeled) are detected as a part of the immobilized complex. In some embodiments, single molecule primer extension reactions can be monitored in real-time to identify the continued incorporation of nucleotides in the extended primer sequence. In such a real-time sequencing (SMRT) analysis, the reaction process of incorporation of nucleotides in the extended primer sequence is monitored as it occurs.

A single molecule analysis of a biological or chemical sample requires detecting and/or collecting photons emitted where the intensity or volume of the photon emissions (e.g., fluorescence emission) can be very low. Therefore, the photon detection and/or collection efficiency requirements can be of great importance in such single molecule analysis. Photon sensing system 500F illustrates a system having the capability of satisfying the photon detection and/or collection efficiency requirements for such single-molecule analysis. As shown in FIG. 5F, photon detection sensor 520F includes a semiconductor substrate 582, a photon detection layer 584 disposed in semiconductor substrate 582, and a filter 588. Photon sensing system 500F further includes one or more optical elements 589 disposed in a light guiding channel 585, a first optical waveguide 581, a second optical waveguide 583 disposed above the first optical waveguide 581, and one or more openings or wells 587 disposed in second optical waveguide 583.

In some embodiments, one of more wells 587 is configured to receive the biological or chemical samples, for example, the single immobilized nucleic acid synthesis complex. Wells 587 can be formed as nanoscale wells disposed in second optical waveguide 583. Second optical waveguide 583 can be, for example, a zero-mode waveguide. A zero-mode waveguide is an optical waveguide that guides light energy into a sample volume that is small in all dimensions compared to the wavelength of the light. Thus, second optical waveguide 583 can optically confine or substantially confine light being directed to the biological or chemical sample disposed in wells 587. Second optical waveguide 583 can therefore form an optical confined area for more efficient illumination of the sample. For example, a small volume of a single immobilized nucleic acid synthesis complex may be disposed inside a well 587. Because the synthesis complex is within an optically confined area provided by second optical waveguide 583 (e.g., a zero-mode waveguide), the excitation light 406 can be confined to the synthesis complex. As a result, the efficiency of illumination can be improved and the single molecule analysis can be performed on a small sample volume. In some embodiments, samples disposed at wells 587 can be received from a fluidic reaction channel, such as channel 302 shown in FIG. 3. And as described above, a single fluidic reaction channel 302 can be disposed across, or shared by, multiple sensors such as photon detection sensor 520F shown in FIG. 5F.

As shown in FIG. 5F, excitation light 406 for illuminating the samples disposed in wells 587 can be directed or guided by first optical waveguide 581 to illuminate the sample disposed in one or more wells 587. First optical waveguide 581 is similar to optical waveguide 404 shown in FIG. 4 and thus not repeatedly described. Similar to those described above, based on the TSV and group dicing technologies, first optical waveguide 581 can be a single optical waveguide disposed across a plurality of photon detection sensors similar to photon detection sensor 520F, such that multiple sensors can share a single optical waveguide 581.

With reference to FIG. 5F, in some embodiments, to minimize or reduce loss of emitted light from samples disposed in wells 587, photon sensing system 500F includes a light guiding channel 585 configured to direct photons emitted as a result of the single molecule analysis to photon detection sensor 520F. In some embodiments, light guiding channel 585 is disposed between first optical waveguide 581 and filter 588 of sensor 520F. Light guiding channel 585 can include optical elements 589 such as reflective cones, reflective optical lenses, and/or diffractive optical lenses. In some embodiments, optical elements 589 can provide a light path for directing photons (e.g., photons of fluorescence light) emitted from the samples to filter 588 and underneath photon detection layer 584 of photon detection sensor 520F by performing, for example, light reflection, diffraction, or channeling. In some embodiments, each biological or chemical sample is disposed in a well 587, which can be aligned with a corresponding optical element 589 in light guiding channel 585. The corresponding optical element 589 can further be optically aligned with a corresponding photosensitive element 584. The alignment of a well 587, an optical element 589, and a photosensitive element 584 can improve the emitted light collection efficiency.

In some embodiments, one or more optical elements 589 can further provide light beam splitting. Optical elements 589 reflective and/or diffractive lenses that can split the emitted light into multiple beams (e.g., 2, 3, 4 beams). The number of beams provided by optical elements 589 can be configured to correspond to the number of photosensitive elements in photon detection layer 520F. For example, the split beams may be configured in a linear manner, or in an array, (e.g., a 2×2 or 3×3 array) based on the configuration of the photosensitive elements of the photon detection sensor 520F. By splitting the emitted light into multiple beams, less number of optical elements 589 may be required (e.g., one instead of four).

With reference to FIG. 5F, in some embodiments, photon detection sensor 520F includes a filter 588 disposed between the light guiding channel 585 and a plurality of photosensitive elements of the photon detection layer 584. Filter 588 can include one or more portions, for example, portions 588A and 588B, configured to allow lights having different wavelength ranges to reach different photosensitive elements of photon detection layer 584. For example, filter portion 588A can be configured to allow emitted light having a first wavelength range to travel to photosensitive elements 584A and 584B of photon detection layer 584. Filter portion 588B can be configured to allow emitted light having a second wavelength range to travel to photosensitive elements 584C and 584D of photon detection layer 584. The first wavelength range may be different from the second wavelength range.

The different portions of filter 588 enables detection of different labeled incorporated nucleotides (e.g., fluorescently labeled nucleotides). For example, emitted fluorescence light based on incorporation of two of the four nucleotides can pass through filter portion 588A to photosensitive elements 584A and 584B (e.g., pixels 584A and 584B); and emitted fluorescence light based on incorporation of the other two of the four nucleotides can pass through filter portion 588B to photosensitive elements 584C and 584D (e.g., pixels 584C and 584D). Further, for the emitted fluorescence light that passes through the same filter portion, the intensity or amplitude of the light may be different for different nucleotides. Therefore, based on the different intensity or amplitude, one out of four labeled incorporated nucleotides (e.g., fluorescently labeled nucleotides) can be determined. The photosensitive elements 584A-D of photon detection layer 584 can be the same or substantially the same as those described above, and are thus not repeatedly described.

As illustrated in FIG. 5F, optical waveguides 581 and 583, light guiding channel 585, the filter 588, and photon detection layer 584 of photon sensing system 500F can enable a single molecule analysis using a small volume of sample. More details of the structure, operation, and fabrication steps of such a photon sensing system for single molecule analysis can be found in U.S. Pat. No. 9,658,161, entitled "ARRAYS OF INTEGRATED ANALYTICAL DEVICES AND METHODS FOR PRODUCTION," filed on May 19, 2016, the content of which is incorporated by reference in its entirety for all purposes.

Similar to those described in FIG. 5A, TSV packaging and RDL technologies can be applied to photon sensing system 500F or photon detection sensor 520F to provide a high throughput or throughput scalable image sensing system. For example, as shown in FIG. 5F, RDL 516 can be disposed to electrically couple pads 514 and spheres 518, thereby re-routing signals from pads 514 to spheres 518. Spheres 518 can be further electrically coupled to external signal processing circuitry. In some embodiments, photon detection sensor 520F is a BSI-based sensor (e.g., the photosensitive elements 584A-D are disposed closer to sample disposed in wells 587 than one or more conductive layers 586 for transmitting electrical signals and implementing signal processing circuits). Thus, similar to those shown in FIG. 5A, pads 514 can be disposed at or near a back surface of a packaged semiconductor die (e.g., the surface at or near which no conductive layers for routing signals is disposed or a surface) or a processing back surface (e.g., back surface of a thinned die). And spheres 518 are disposed at or near a front surface of a packaged semiconductor die (e.g., the surface at or near which conductive layers for routing signals are disposed). Further, group dicing technology can also be applied to obtain a throughput-scalable image sensing system based on photon detection sensor 520F, such that multiple photon detection sensor 520F are disposed on packaged semiconductor dies diced from a single wafer as a group. The details of TSV packaging, RDL routing, and group dicing technologies can be applied in a similar manner as described above, and are thus not repeatedly described here. While FIG. 5E illustrates one photon detection sensor 520F, it is appreciated that multiple photon detection sensors can be included in photon sensing system 500F. The multiple photon detection sensors can be configured similar to that shown in FIG. 4A or 4B.

With reference back to FIG. 3, throughput-scalable sensing system 300 includes a signal and data processing system 330. In some embodiments, a signal processing circuitry of signal and data processing system 330 can be electrically coupled to one or more sensors 320A-N to receive electrical signals (e.g., photoelectrons) generated by sensors 320A-N. In some embodiments, the signal processing circuitry of signal and data processing system 330 can include one or more charge storage/transfer elements, an analog signal readout circuitry, and a digital control circuitry. In some embodiments, the charge storage/transfer elements (e.g., a charge transfer amplifier) can receive, amplifier, store, and/ or read out electrical signals generated in sequence or in parallel by the photosensitive elements of a sensor 320 (e.g., using a rolling shutter or a global shutter); and transmit the received electrical signals to the analog signal read-out circuitry. The analog signal read-out circuitry may include, for example, an analog-to-digital converter (ADC), which converts analog electrical signals to digital signals.

In some embodiments, the signal processing circuitry of signal and data processing system 330 can include a rolling shutter, which enables sequential readout of electrical signals generated by the photosensitive elements of a sensor 320. A rolling shutter exposes different rows of a photosensitive elements array (e.g., a pixel array) of a sensor at different times and reads out in a chosen sequence. In a rolling shutter, although each row of the photosensitive elements array of the sensor may be subject to the same exposure time, the rows at the top of the photosensitive elements array of the sensor may end the exposure before the rows at the bottom of the photosensitive elements array of the sensor. This may lead to spatial distortion, especially for large scale image sensing systems. However, because each sensor 320A-N in sensing system 300 is disposed on a separate semiconductor die using the group dicing technology, these sensors 320 shown in FIG. 3 can be small-to-medium scale sensors independent from other sensors. As described above, the group dicing technology reduces or avoids the requirements for large scale image sensing system using a large single pixel array for a sensor. Instead, sensing system 300 can include multiple small-medium size pixel arrays. As a result, a rolling shutter can be used in a throughput-scalable sensing system described (e.g., system 300) in this disclosure without spatial distortion or with reduced spatial distortions.

In some embodiments, the signal processing circuitry of signal and data processing system 330 can include a global shutter, which enables a substantial concurrent readout of electrical signals generated by the photosensitive elements of the sensors 320. Using a global shutter can improve the signal readout speed over a rolling shutter. A global shutter can expose all photosensitive elements (e.g., pixels) simultaneously or concurrently. At the end of the exposure, the collected charge or electrical signal can be transferred to the readout nodes of the analog signal readout circuitry simultaneously or at substantially the same time. As a result, a global shutter eliminates or reduces spatial distortion, especially for large scale sensing systems. In some embodiments, eliminating or reducing spatial distortion can have significantly positive impact on high-throughput nucleotide sequencing, which frequently relies on high-resolution detection of large amounts of fine targets at high density. Global shutter techniques can improve the accuracy of co-registration of a large quantity (e.g., millions) of DNA image spots on many (e.g., thousands) sequencing images repeatedly recorded at different testing times.

Figure 6:
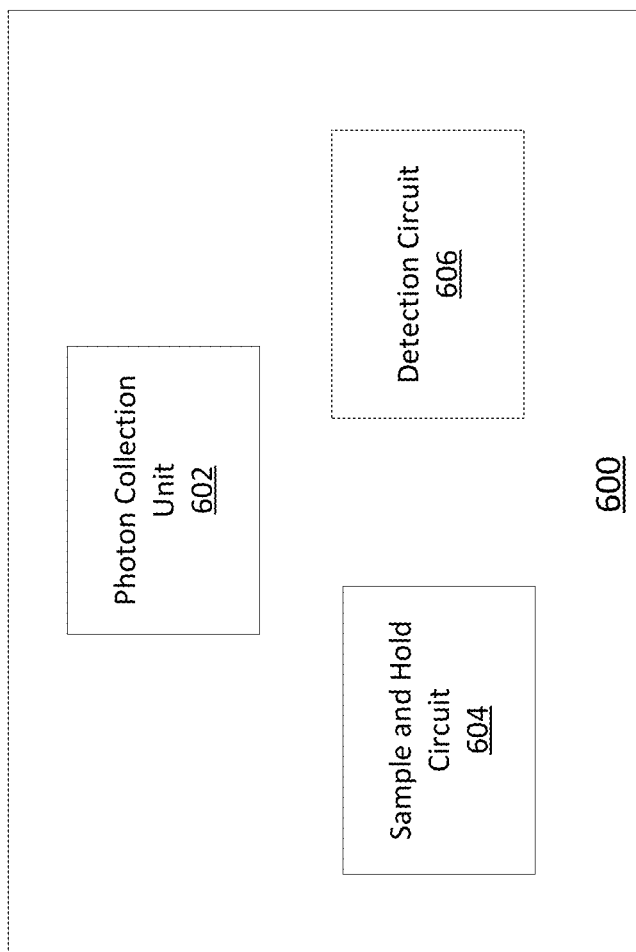
FIG. 6 is block diagram illustrating the operation of an exemplary event-triggered shutter.

The above described rolling shutter or global shutter typically operates at a fixed rate in exposing photosensitive elements and transferred the collected charge or electrical signals to readout nodes. In some embodiments, the signal processing circuitry of signal and data processing system 330 can include an event triggered shutter. An event triggered shutter does not operate in a fixed rate. Instead, it is capable of selectively reading out of electrical signals generated by photosensitive elements of sensors 320. FIG. 6 is a block diagram 600 illustrating an exemplary event-triggered shutter. As shown in FIG. 6, a photon collection unit 602 can be controlled to collect photons of the light from the samples being analyzed at certain integration time. The collection of photons is sometimes also referred to as photosensitive element exposure. The photons collected over a predetermined integration time can be converted, by the photosensitive elements, to photoelectrons or electrical signals. An event-triggered shutter can include a sample and hole circuit 604 and a detection circuit 606. Sample and hold circuit 604 can provide the electrical signals in the form of an output voltage. This output voltage can be provided to detection circuit 606 of the event-triggered shutter. In some embodiments, detection circuit 606 can include a voltage comparator that compares the output voltage to a threshold voltage. If the output voltage is greater than the threshold voltage, the collected charge or electrical signal (e.g., the output voltage) can be transferred to the readout nodes of the analog signal readout circuitry. Thus, detection circuit 606 of the event-triggered shutter can selectively read out electrical signals generated by the photosensitive elements based on a result of the comparison of an output voltage with a threshold voltage.

An event-triggered shutter provides several advantages. For example, instead of blindly reading out all the electrical signals generated by the photosensitive elements, signals can be selectively read out for only effective events. This is particularly beneficial for chemiluminescence light detection, because electrical signals generated based on chemiluminescence light detection may not be produced at a fixed rate. Therefore, reading out such electrical signals at a fixed rate would unnecessarily increase data flow and impose extra processing burden on the signal and data processing circuitry. Further, event-triggered shutter can enable flexible signal readout by adjusting integration time and/or threshold voltages. For instance, by increasing integration time and/or reducing threshold voltage, low intensity light emissions can be detected (e.g., for analysis of samples having small volumes such as single molecule analysis, or single photon detection as described more in detail below). Therefore, an event-triggered shutter can enable reading out of both strong and weak electrical signals (corresponding to high and low light intensity light emissions). Further, in some embodiments, each photosensitive element (e.g., each pixel) can be configured to have one integration time using the event-triggered shutter. Thus, each photosensitive element can have exposure independent of other photosensitive elements, thereby improving the flexibility of reading out electrical signals for different pixels in a pixel array of a sensor.

In addition to a signal processing circuitry, signal and data processing system 330 shown in FIG. 3 can include a data processing system. After the signal processing circuitry converts analog electrical signals to digital signals (e.g., using an ADC), it can transmit the digital signals to the data processing system for further processing. For example, the data processing system can perform various digital signal processing (DSP) algorithms (e.g., compression) for high-speed data processing. In some embodiments, at least part of the data processing system can be integrated with the signal processing circuitry on a same semiconductor die or chip. In some embodiments, at least part of the data processing system can be implemented separately from the signal processing circuitry of system 330 (e.g., using a separate DSP chip or cloud computing resources). Thus, data can be processed and shared efficiently to improve the performance of the sample analytical system. It is appreciated that at least a portion of the signal processing circuitry and the data processing system of signal and data processing system 330 can be implemented using, for example, CMOS-based application specific integrated circuits (ASIC), field programmable gate array (FPGA), discrete IC technologies, and/or any other desired circuit techniques.

With reference to FIG. 3, in some embodiments, one or more sensors 320 can be photon counting image sensors such as quanta CMOS image sensors (QISs). A QIS has very small photosensitive elements (e.g., 100-1000 nm pitch) with small full well capacity (e.g., 1-200 carriers). A QIS photosensitive element is also referred to as sub-diffraction limit (SDL) photosensitive element. An SDL photosensitive element can be sensitive to single photoelectrons, such that the presence or absence of one photoelectron results in a logical binary output of 0 or 1 at readout. An SDL photosensitive element is also frequently referred to as a "jot" device (Greek for "smallest thing"). And a QIS may include many photosensitive elements to generate hundreds, thousands, or millions of outputs (e.g., binary bits of 0s and 1s). The outputs from the photosensitive elements can form two dimension or three-dimensional arrays. For example, at any given time, a plurality of QIS photosensitive elements can provide 16×16 array of outputs (or any size array depending on the two spatial dimensions of the QIS photosensitive elements). Such an array of outputs can form a bit plane, each corresponding to a field. Multiple bit planes generated by the plurality of QIS photosensitive elements at different time can form a data cube having a three-dimensional array (e.g., a 16×16×16) with the third dimension being the temporal dimension.

In some embodiments, a single image pixel can be generated based on one or more such two-dimensional or three-dimensional arrays generated by the plurality of QIS photosensitive elements. For example, signal and data processing system 300 can process the 16×16×16 data cube and generate a single image pixel, which represents a local light intensity received by the QIS photosensitive elements. Accordingly, by adjusting or configuring the size of the two-dimensional arrays or three-dimensional arrays, the output image pixel size of a QIS is programmable for trading resolution with sensitivity. For example, if more QIS photosensitive element outputs (e.g., a large data cube) are included for generating a single image pixel, the light intensity is increased and the sensitivity of the QIS can be enhanced. And if less QIS photosensitive element outputs (e.g., a large data cube) are included for generating a single image pixel, the resolution of the output image may be increased with a reduced sensitivity. It is also appreciated that different image pixels may be generated based on data cubes of different sizes and the multiple data cubes may overlap.

A QIS is one type of photon counting sensors or photoelectron-counting sensors that are capable of detecting a single photon. Other types of photon-counting sensors (e.g., sCMOS, EMCCD, or SPAD) often require avalanche multiplication to achieve high conversion gain. Thus, fabrication of these types of photon-counting sensors can require special processes that are complex and costly. A QIS is compatible with standard CMOS image sensor fabrication process. Further, as described above, a QIS has very small photosensitive elements (e.g., 100-1000 nm pitch) with small full well capacity (FWC). Thus, a QIS photosensitive element can have high conversion gain, low readout noise, and low dark current. As a result, a QIS does not require those complex, special, and costly processes used in other types of photon-counting sensors.

Figure 7A:
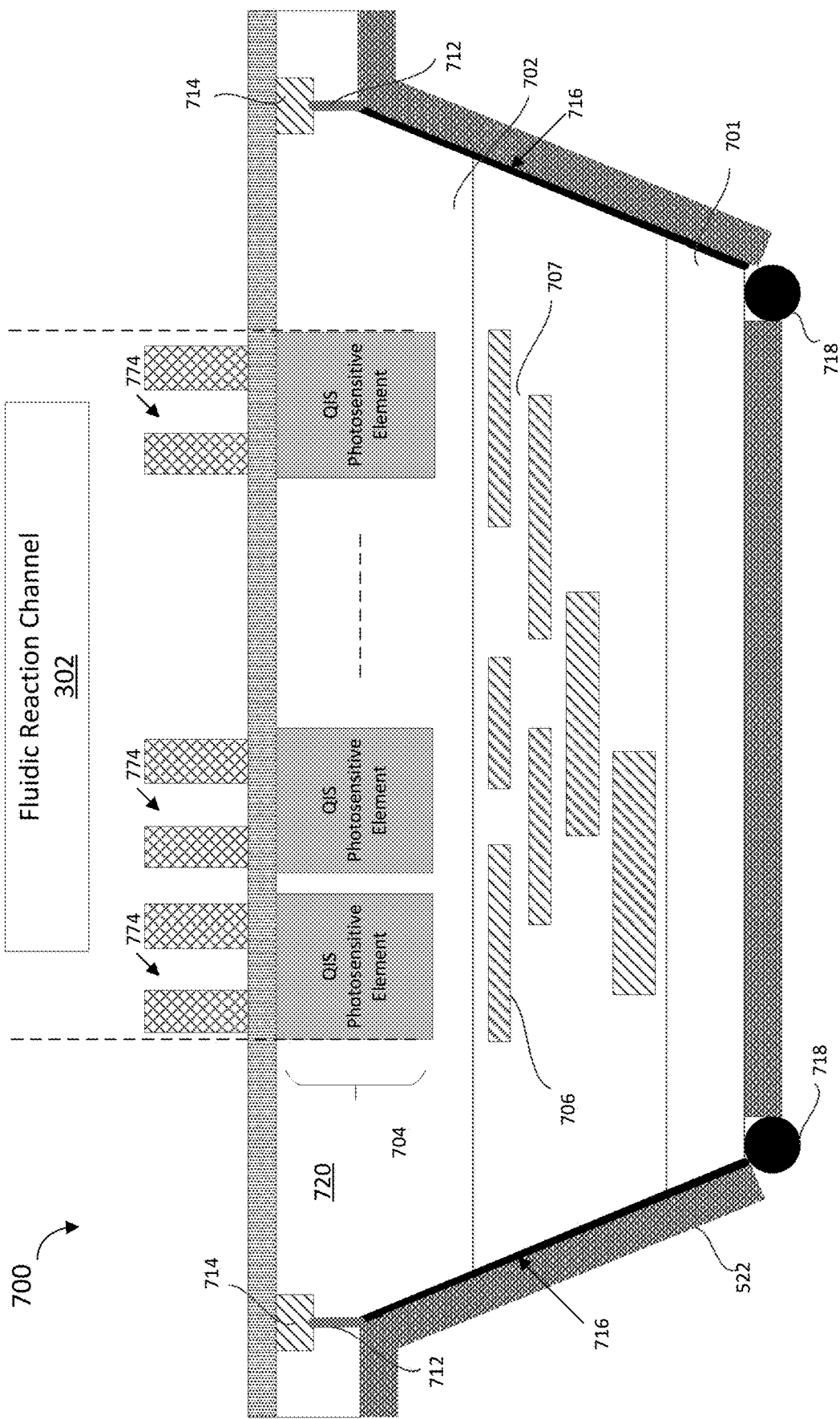
FIG. 7A illustrates an exemplary quanta CMOS image sensor (QIS) based sensing system with a cross-sectional view of an embodiment of a TSV packaged QIS sensor.

FIG. 7A illustrates an exemplary QIS-based sensing system 700 with a cross-sectional view of an embodiment of a TSV packaged QIS 720. Similar to FIG. 5A, QIS-based sensing system 700 can be a BSI-based sensing system including a QIS 720, a fluidic reaction channel 302 and optical system 304 (not shown in FIG. 7A). Fluidic reaction channel 302 and optical system 304 can be substantially the same as those described above and are thus not repeatedly described. Similar to a BSI-based image sensor described above, QIS 720 can include a plurality of QIS photosensitive elements 704 (e.g., SDL photosensitive elements). In some embodiments, as shown in FIG. 7A, a fluidic reaction channel 302 can provide samples that are disposed in openings or wells 774. Wells 774 can be positioned above corresponding QIS photosensitive elements 704 for performing a nucleotide acid sequencing analysis. For example, the sample can be a single immobilized nucleic acid synthesis complex used for a single molecule sequencing analysis. It is appreciated that fluidic reaction channel 302 can also provide samples for other types of sequencing analysis such as cluster sequencing analysis. In some embodiments, similar to those described above, fluidic reaction channel 302 can be disposed across multiple QISs, with each disposed on a semiconductor die of a single semiconductor wafer. In some embodiments, fluidic reaction channel 302 can be disposed separately to provide samples (e.g., synthesis complex) to wells 774 positioned above multiple QISs.

Figure 7B:
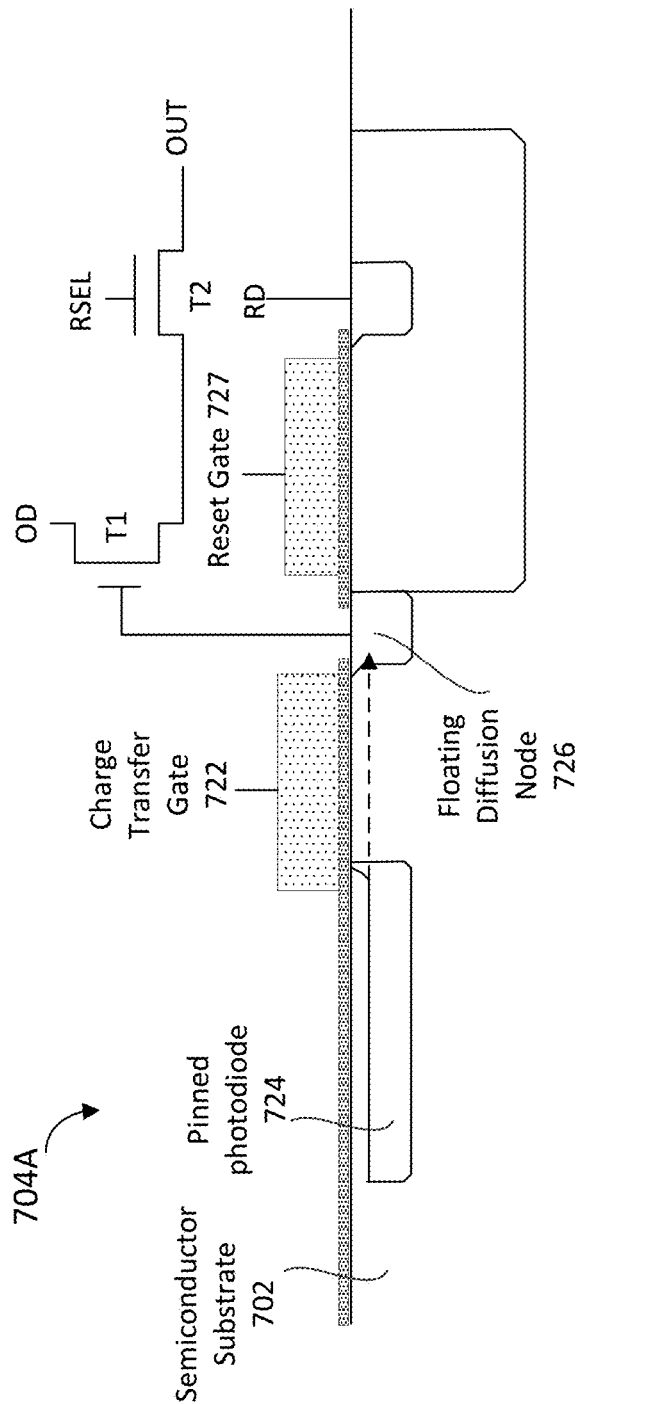
FIG. 7B illustrates an exemplary QIS photosensitive element.

As described above, QIS-based sensing system 700 includes a plurality of QISs, such as QIS 720. QIS 720 can include many (e.g., thousands or millions) QIS photosensitive elements 704 (e.g., SDL photosensitive elements). An exemplary QIS photosensitive element 704A is illustrated in FIG. 7B. In some embodiments, QIS photosensitive element 704A can be a pinned photodiode based photosensitive element. As illustrated in FIG. 7D, QIS photosensitive element 704A can include a charge transfer gate 722 disposed above a semiconductor substrate 702 of a semiconductor die. QIS photosensitive element 704A can further include a pinned photodiode 724 disposed in semiconductor substrate 702 at a first side (e.g., left side as shown in FIG. 7B) of charge transfer gate 722. QIS photosensitive element 704A can further include a floating diffusion node 726 disposed in semiconductor substrate 702 at a second side (e.g., right side as shown in FIG. 7B) of the charge transfer gate 704. Pinned photodiode 724 can detect photons and generate photoelectrons based on the detected photons. Upon applying a proper potential on charge transfer gate 704, the charges of the photoelectrons can be transferred to floating diffusion node 726. Thus, the combination of charge transfer gate 722, pinned photodiode 724, and floating diffusion nodes 726 can detect photons and transfer the photoelectron charges to be subsequently read out. In some embodiments, QIS photosensitive element 704A can further include a readout circuitry (e.g., a source follower) and other logics (e.g., reset logic), some of which are shown in FIG. 7B.

In FIG. 7B, charge transfer gate 722 and floating diffusion node 726 may be overlapped spatially. The capacitance of floating diffusion node 726 can include depletion capacitance between floating diffusion node 726 and semiconductor substrate 702, overlap capacitance between floating diffusion node 726 and charge transfer gate 722, overlap capacitance between floating diffusion node 726 and a reset gate 727, and other capacitances (e.g., source-follower gate capacitance, inter-metal capacitance, etc.). To improve the conversion gain of the QIS photosensitive element, overlap capacitance between floating diffusion node 726 and charge transfer gate 722 needs to be reduced, because the conversion gain is reversely proportional to the capacitance of floating diffusion node 726.

Figure 7C:
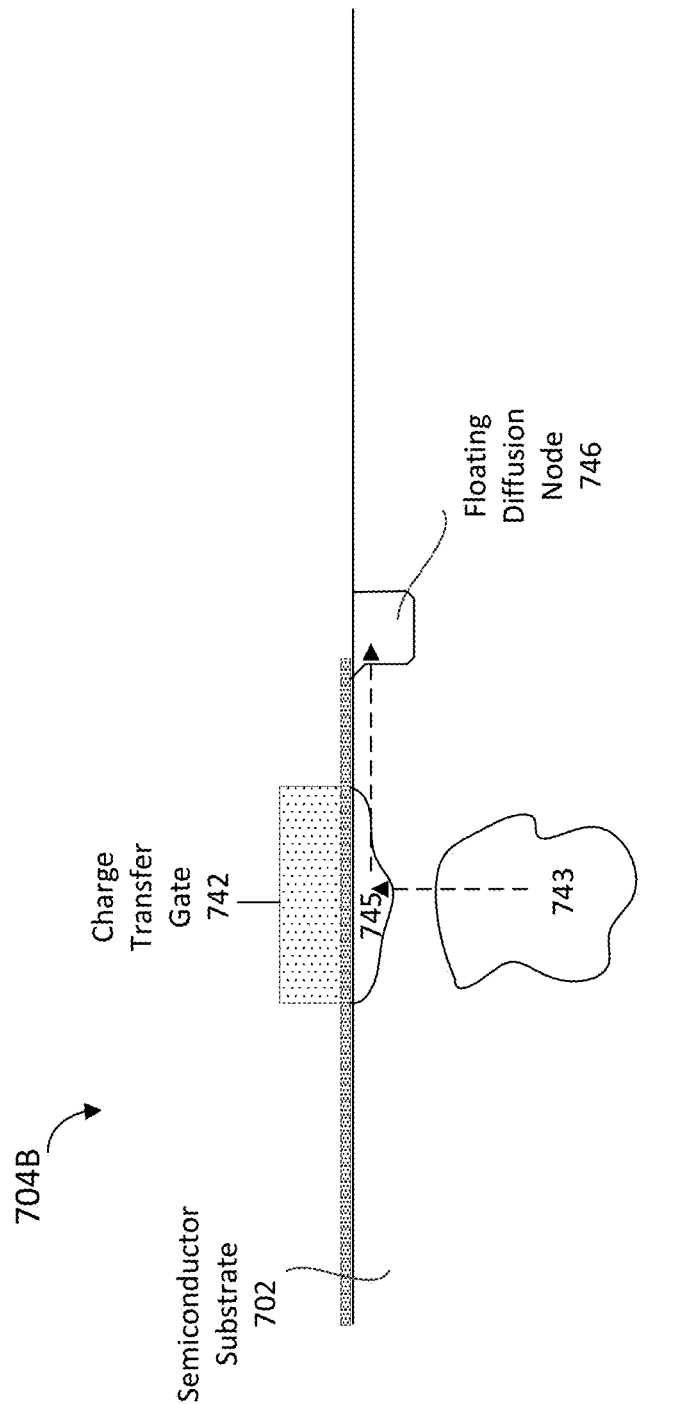
FIG. 7C illustrates another exemplary QIS photosensitive element.
Figure 7D:
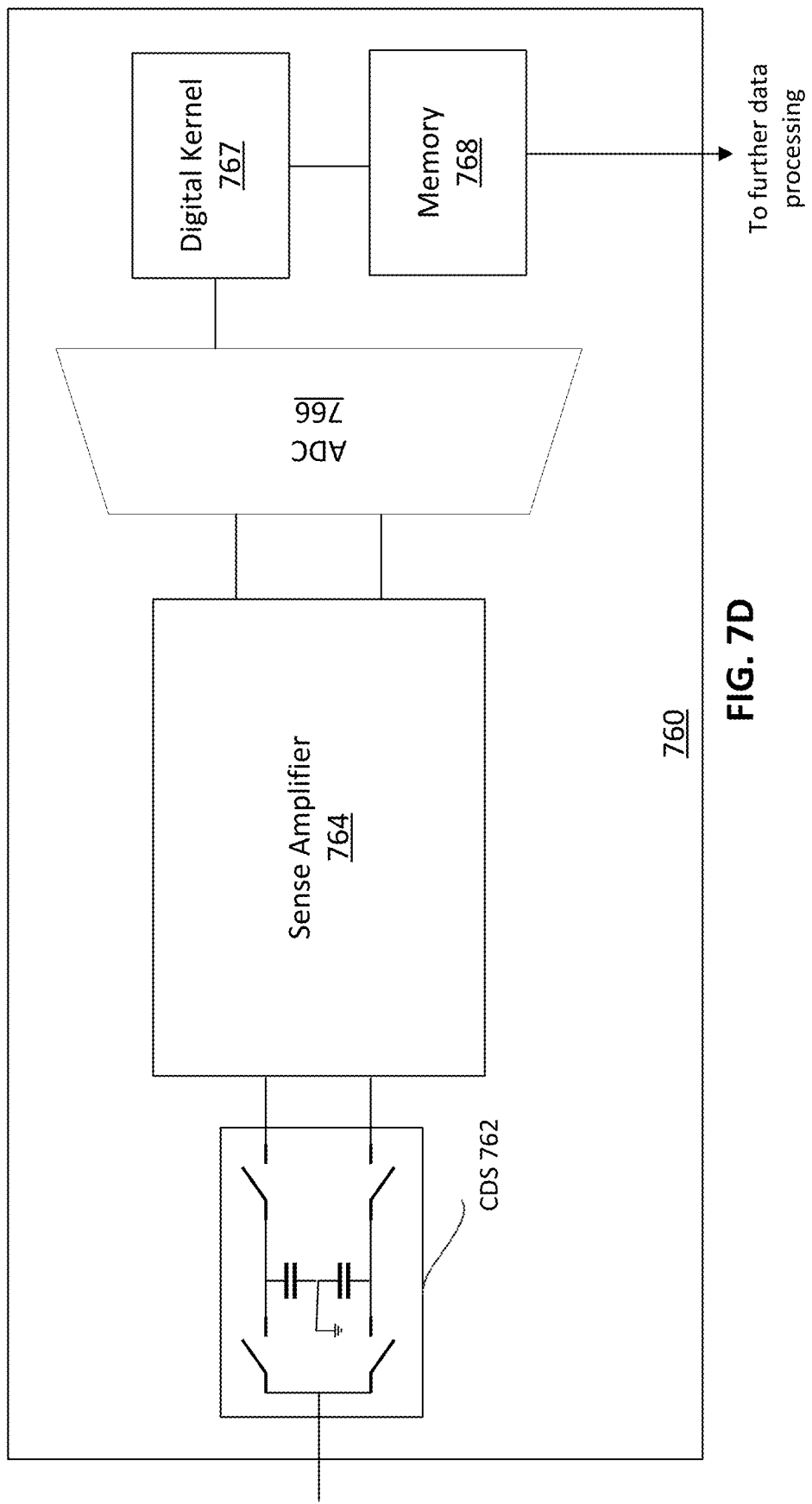
FIG. 7D illustrates an exemplary signal processing circuitry for processing outputs of a QIS.

FIG. 7C illustrates another QIS photosensitive element 704B with reduced overlap capacitance. As shown in FIG. 7C, QIS photosensitive element 704B includes a charge transfer gate 742 and a floating diffusion node 746. Charge transfer gate 742 and floating diffusion node 746 are not spatially overlapped so that the overlap capacitance is reduced. In QIS photosensitive element 704B, different diffusion areas (e.g., areas 743 and 745) with proper implantation or carrier concentration in semiconductor substrate 702 are configured to have different doping concentrations. Photoelectrons can be detected and accumulated in one area (e.g., area 743 that is associated with a photodiode) of the semiconductor substrate 702. When a proper potential is applied on charge transfer gate 742 and therefore the charge transfer gate 742 is turned on, the charges of the accumulated photoelectrons can be transferred from area 743 to another area 745 of semiconductor substrate 702. Area 745 can be directly under the charge transfer gate 742. The charges can then be transferred to floating diffusion node 746 in a pump action when the charge transfer gate 742 is turned off. It is appreciated that a QIS photosensitive element is not limited to the above described elements 704A and 704B. Other types of QIS photosensitive elements (e.g., a junction FET based on element) can also be used in a QIS.

With reference back to FIG. 7A, similar to those described in FIG. 5A, TSV packaging and RDL technologies can be applied to QIS-based sensing system 700 or QIS 720 to provide a high throughput or throughput scalable image sensing system. For example, as shown in FIG. 7A, RDL 716 can be disposed to electrically couple pads 714 and spheres 718, thereby re-routing signals from pads 714 to spheres 718. RDL 716 is partially enclosed by through-hole vias 712. Spheres 718 can be further electrically coupled to external signal processing circuitry such as readout circuitry as described in more detail below. In some embodiments, as described above, QIS 720 is a BSI-based sensor (e.g., the QIS-based photosensitive elements 704 are disposed closer to sample disposed in wells 774 than conductive layers 706 for transmitting electrical signals and implementing signal processing circuits). Thus, similar to those shown in FIG. 5A, pads 714 can be disposed at or near a back surface of a semiconductor die (e.g., the surface at or near which no conductive layers for routing signals is disposed or a surface) or a surface of a thinned die. And spheres 718 are disposed at or near a front surface of a semiconductor die (e.g., the surface at or near which conductive metal layers for routing signals are disposed) or a surface of a carrier wafer 701. Further, group dicing technology can also be applied to obtain a throughput-scalable QIS-based photon sensing system based on QIS 720, such that multiple QISs 720 are disposed on semiconductor dies diced from a single wafer as a group. The details of TSV packaging, RDL routing, and group dicing technologies can be applied in a similar manner as described above, and are thus not repeatedly described here.

As described above, a QIS-based photosensitive element 704 can include a readout circuitry (e.g., a source follower) for reading out the charge transferred to a floating diffusion node. In some embodiments, the output from a QIS-based photosensitive element can be transmitted to external signal processing circuitry for further processing. FIG. 7D illustrates such a signal processing circuitry 760. In some embodiments, signal processing circuitry 760 can include a correlated double sampling (CDS) circuit 762 configured to sample an output voltage signal of one of more QIS-based photosensitive elements. The sampled output voltage signal can be transmitted to a sense amplifier 764 electrically coupled to the correlated double sampling circuit 762. Sense amplifier 764 can amplify small signals (e.g., signals having small amplitude) to logically distinguishable signals. The output signals from sense amplifier 764 can be transmitted to an analog to digital converter 766 for converting analog signals to digital signals. Signal processing circuitry 760 may include other circuitry such as digital kernel 767 and memory 768, for further digital signal processing, buffering, and storing of the data.

Figure 7E:
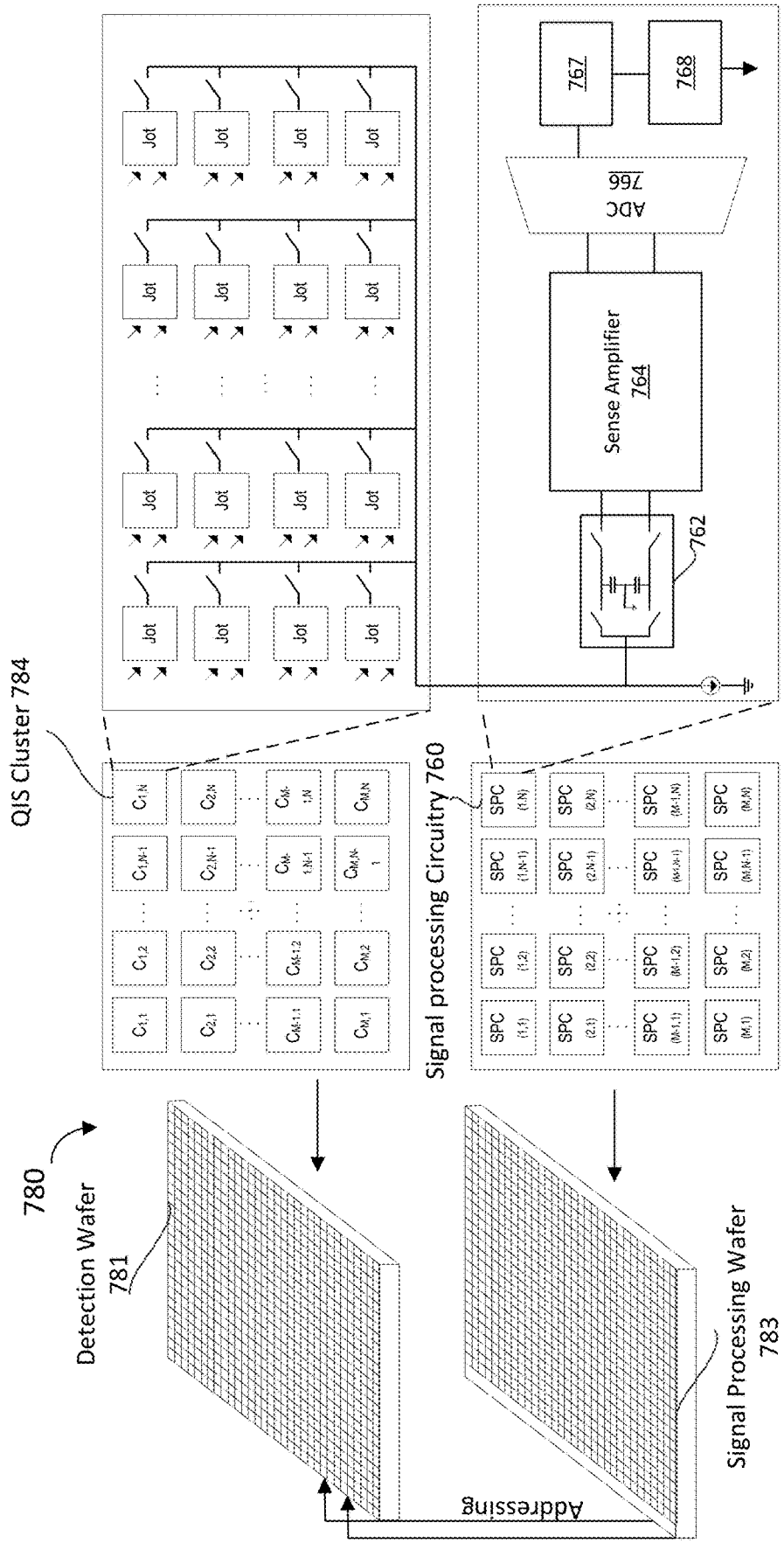
FIG. 7E illustrates wafer-level prospective diagrams and corresponding block diagrams of an embodiment of an exemplary QIS-based sensing system.

In some embodiments, group dicing and wafer level bonding technologies can be used with a QIS-based sensing system. FIG. 7E illustrates wafer-level prospective diagrams and corresponding block diagrams of an embodiment of an exemplary QIS-based sensing system 780. As shown in FIG. 7E, using the group dicing technology described above, system 780 can include a plurality of semiconductor dies separated from a first semiconductor wafer 781 and a plurality of semiconductor dies separated from a second semiconductor wafer 783. The dies can be separated as groups as described above using group dicing technology. In some embodiments, QIS photosensitive elements (e.g., SDL photosensitive elements or "jots") can be fabricated or disposed on the dies of first semiconductor wafer 781 and therefore wafer 781 may also be referred to as the detection wafer. In some embodiments, signal processing circuitry such as readout circuits can be fabricated or disposed on the dies of second semiconductor wafer 783, and therefore wafer 783 may also be referred to as the signal processing wafer or ASIC wafer. In some embodiments, QIS photosensitive elements of wafer 781 can be electrically coupled to the signal processing circuitry of wafer 783 using wafer level packaging technologies, such as the TSV and RDL technologies as described above. For example, the TSV and RDL technologies can be applied to detection wafer 781 such that spheres (e.g., solder balls), instead of wire bonding, are used to electrically couple devices on wafer 781 to devices on wafer 783. Wafer level packaging technologies can thus enable a high density and large scale QIS-based sensing system.

As illustrated in FIG. 7E, in some embodiments, each semiconductor die of wafer 781 can include a QIS having many QIS-based photosensitive elements. A group or array of QIS can form a QIS cluster 784 and detection wafer 781 can include many QIS clusters. Similarly, each semiconductor die of wafer 783 can include a signal processing circuitry 760 for one or more corresponding QIS, such as readout circuits. As described above, signal processing circuitry 760 can include, for example, a CDS 762, a sense amplifier 764, an ADC 766, and other circuits 767 and 768. More details of the structure, operation, and fabrication steps of a QIS can be found in "The Quanta Image Sensor: Every Photon Counts" by Eric R. Fossum et al. Published by Sensors, MDPI journal on Aug. 10, 2016, the content of which is incorporated by reference in its entirety for all purposes.

As described above, a sensing system obtained based on group dicing may result in an image having image gaps due to the physical separations of sensors by the dicing streets (and other structures). Thus, an image generated by QIS-based photo sensing system 700 shown in FIG. 7A may have image gaps because group dicing is used for fabricating such a system. While image gaps may be unacceptable in some applications, they have no or minimum impact on the performance on a sensing system that is used for a biological or chemical sample analysis applications (e.g., a nucleotide acid sequencing application). For many biological or chemical sample analysis application, QIS-based sensing system 780 can be used to count photons emitted from the samples. And the analysis results are often based on the information related to photon counting (e.g., the intensity of photons, position of photons, pattern of photons, etc.). Therefore, a high-throughput scalable sensing system including multiple group-diced QISs can be readily used for many biological or chemical sample analysis applications or any other photon counting based applications, without having to make mitigation effort to remove the gaps or stitch portions of the images together.

FIGS. 8A-8G illustrate cross-sectional views associated with processing steps for fabricating a throughput-scalable sensing system such as systems 300, 500A-F, and 700. It is appreciated that the processing steps shown in FIGS. 8A-8G may not include all steps and may have variations. The cross-sectional views may not illustrate all elements of the throughput-scalable sensing system and may not be drawn to scale. For illustration purposes, the fabrication process shown in FIGS. 8A-8G uses BSI-based image sensing system as an example. It is appreciated that the fabrication process shown in FIGS. 8A-8G, or a variation thereof, can be applied to any sensing system described above, such as an FSI-based image sensing system, a chemically sensitive sensor based sensing system, a transmembrane pore sensor based sensing system, a photon detection sensor based sensing system, and a QIS based sensing system.

Figure 8A:
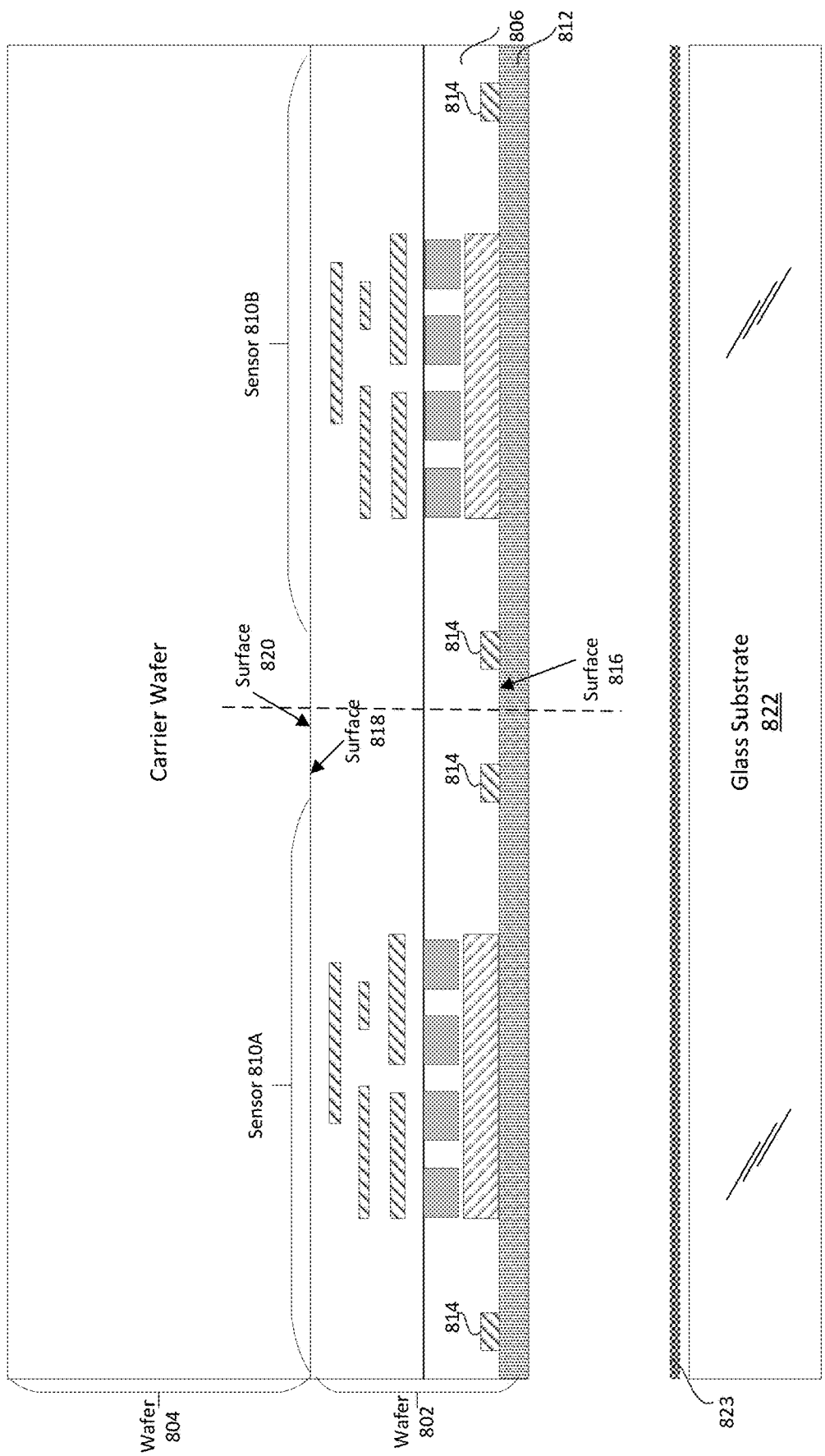
FIGS. 8A-8G illustrate cross-sectional views associated with processing steps for fabricating a throughput-scalable sensing system.

With reference to FIG. 8A, in some embodiments, two wafers 802 and 804 are received for fabricating a throughput-scalable sensing system. Wafer 802 can include a semiconductor substrate 806 (e.g., a Silicon substrate) and a plurality of sensors. FIG. 8A illustrates two such sensors 810A and 810B. For illustration purposes, sensors 810A and 810B are illustrated as BSI-based image sensor in FIGS. 8A-8G. It is appreciated that sensors 810A and 810B can be any of the sensors described above. As shown in FIG. 8A, sensors 810A and 810B can include a photon detection layer that includes a plurality of photosensitive elements, filter, conductive layers for implementing readout circuits and other circuits as described above, dielectric layers (e.g., SiO2 for isolating the conductive layers from one another), and/or a passivation layer. In some embodiments, sensors 810A and 810B are fabricated or disposed in two separate semiconductor dies of wafer 802, and are electrically isolated from each other (e.g., by field oxide). The fabrication of these sensors can use, for example, standard CMOS image sensor (CIS) process or any suitable processes for the different types of sensors as described above.

As illustrated in FIG. 8A, in some embodiments, prior to receiving wafer 802, semiconductor substrate 806 of wafer 802 can be thinned from a back surface of wafer 802. Thinning of back surface can be required for a BSI-based image sensor, but may not be required for an FSI-based image sensor or other type of sensors. As described above and shown in FIGS. 3, 4, and 5A, an optical system (e.g., a waveguide) may be disposed on the back surface to direct the excitation light to the samples; and the samples may be disposed on the optical system. The light emitted from the samples travels to the photosensitive elements in the semiconductor substrate. Thus, thinning of the semiconductor substrate 806 from the back surface of wafer 802 can reduce the distance the light emitted from the samples has to travel. As a result, the light collection and detection efficiency of the sensors 810A-B can be improved. As used in this disclosure, the front surface of a wafer is a surface at or near which one or more conductive layers and one or more dielectric layers are disposed; and the back surface of a wafer is a surface opposite to the front surface. The back surface is usually a semiconductor substrate surface. In some embodiments, a passivation layer 812 can be deposited on the thinned back surface 816 of wafer 802. Thinning of wafer 802 can be performed using, for example, chemical-mechanical polishing or planarization (CMP), mechanical thinning, and/or wet or dry etching (isotropic etching or anisotropic etching). Similar to those described above, passivation layer 812 can provide protection of wafer 802 from liquid damage and/or mechanical damage. Passivation layer 812 can be deposited using CVD, PVD, or any other depositing process.

In some embodiments, as shown in FIG. 8A, wafer 802 can be bonded with wafer 804. As described above, in some embodiments, wafer 802 is thinned (e.g., for fabricating BSI-based image sensing system) and therefore may be fractured or damaged during the subsequent processing steps. Wafer 804 can be a carrier wafer to provide support for wafer 802 to reduce or eliminate the likelihood that the wafer 802 is damaged during the subsequence processing steps. As shown in FIG. 8A, bonding of wafer 802 and wafer 804 can be performed at the front surface 818 (e.g., the surface that is disposed with conductive layers and dielectric layers) of wafer 802 and at surface 820 of carrier wafer 804. It is appreciated that wafer 804 may be optional for certain type of sensors that do not require thinning of wafer 802 (e.g., FSI-based image sensors). If wafer 802 is not thinned, it may not require extra support and thus a carrier wafer may not be required. Wafers 802 and 804 can be bonded using any suitable wafer bonding technologies including direct bonding, surface activated bonding, adhesive bonding, thermocompression bonding, etc.

In some embodiments, wafer 802 may be stacked with a third wafer (not shown). As described above, the group dicing technology described in this disclosure enables a sensing system to be easily scaled or stacked up to provide parallel signal and data processing in a large-scale sensing application (e.g., 100 meg-1 giga image sensing application). Thus, two or more wafers can be stacked such that the sensing system is more compact. One example of stacking wafers is illustrated in FIG. 7E and described above. For instance, wafer 781 (e.g., a detection wafer) and wafer 783 (a signal processing wafer) can be stacked with each other for providing a large scale QIS-based sensing system.

Figure 8B:
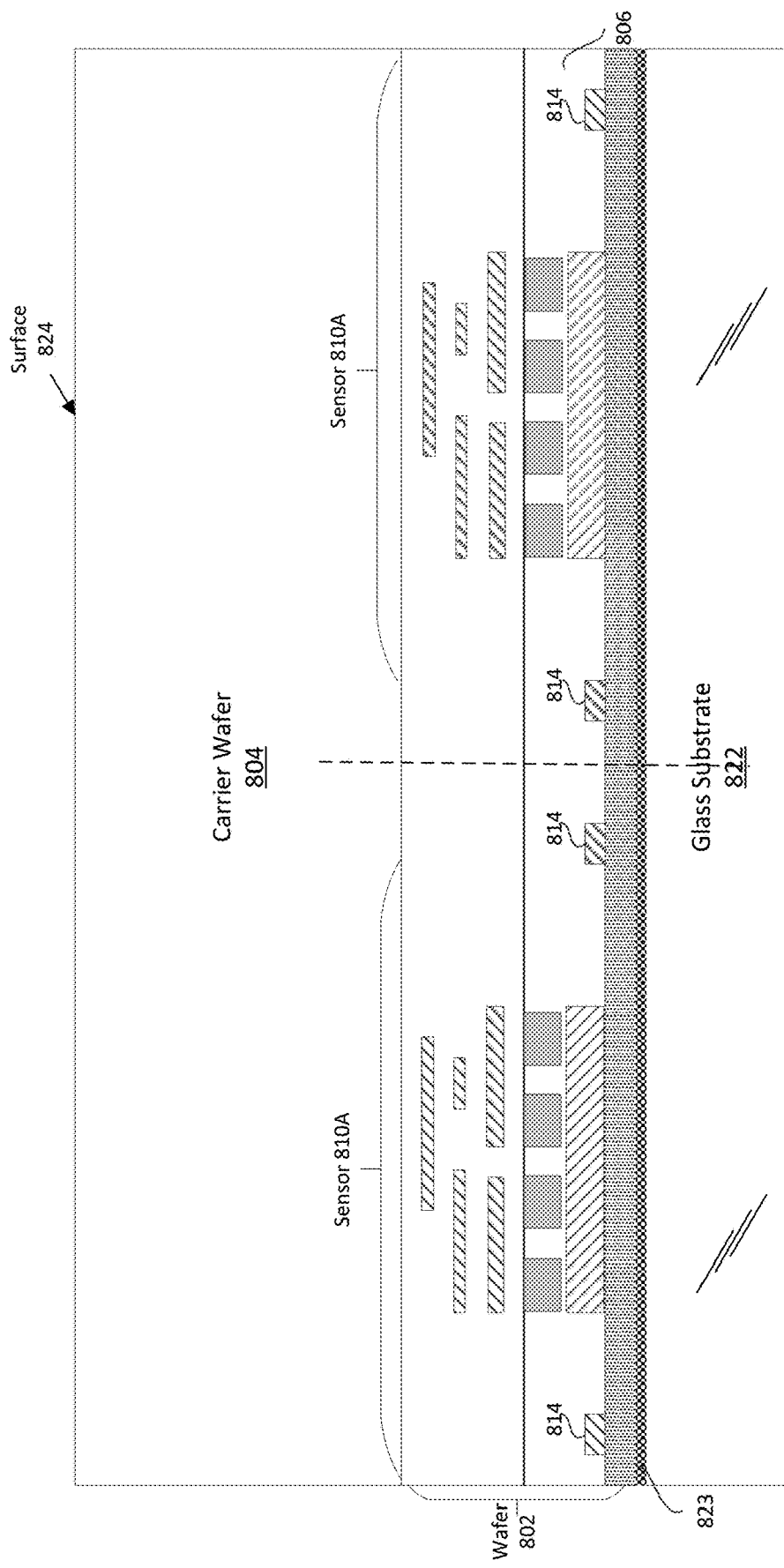
Figure 8C:
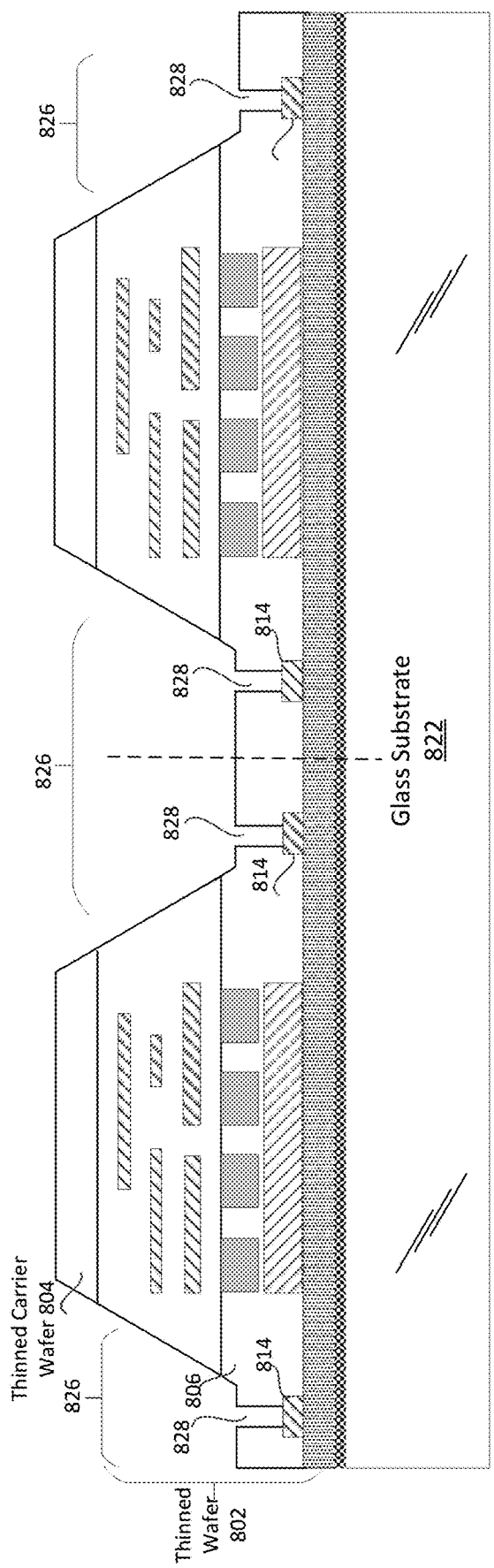

After bonding wafers 802 and 804, they are prepared for conductive path redistribution. FIGS. 8A-8C illustrate the processes for preparing bonded wafers 802 and 804 for conductive path redistribution. As described above, conductive path redistribution renders input/output pads (e.g., pads 814) of an integrated circuit or device (e.g., sensors 810A-B) available in other locations. As shown in FIGS. 8A and 8B, a detachable glass substrate 822 can be adhesively bonded to wafer 802. The bonding of glass substrate 822 can use bonding adhesives 823 to mechanically attach glass substrate 822 to wafer 802. In some embodiments, the bonding adhesives can be soluble so that glass substrate 822 can be detached from wafer 802 after the conductive redistribution paths are formed.

In addition to bonding glass substrate 822, preparing wafers 802 and 804 for conductive path redistribution can also include thinning a portion of wafer 802 and a portion of wafer 804. FIGS. 8B-8C illustrate cross-section views of the wafers before and after the thinning process. In some embodiments, as shown in FIG. 8B, wafer 804 can be thinned from surface 824. Surface 824 is opposite to the bonded interface between wafer 802 and wafer 804. Thinning can be performed using chemical-mechanical polishing or planarization (CMP), mechanical thinning, and/or wet or dry etching (isotropic etching or anisotropic etching). In some embodiments, thinning of wafer 802 can be performed to remove semiconductor substrate of a certain thickness or thickness range. The thinning can be isotropic or substantially the same across wafer 802.

In some embodiments, following an isotropic thinning of wafer 802, a directional or anisotropic etching can be performed. For example, a first mask layer (not shown) can be deposited to define areas 826 for anisotropic etching. Anisotropic etching can then be performed to remove materials in the defined areas 826. For example, as shown in FIG. 8C, anisotropic etching can further remove a portion of the semiconductor substrate of wafer 804, dielectric layers of wafer 802, and a portion of semiconductor substrate of wafer 802. Anisotropic etching can be performed by wet etch or dry etch processes. After the anisotropic etching process, the first mask layer (e.g., a photoresist layer) can be removed.

After preparing the wafer 802 and wafer 804 for conductive path redistribution, one or more redistribution paths can be formed. In FIG. 8C, through-hole vias 828 are formed in the semiconductor substrate 806 of thinned wafer 802. Forming through-hole vias 828 can be performed by, for example, anisotropic etching (e.g., dry etching) of semiconductor substrate 806. For example, a second mask layer can be deposited to define areas to be etched from the semiconductor substrate 806 of wafer. The defined areas can correspond to areas above the electrically-conductive pads 814. Based on the defined areas, a portion of the semiconductor substrate 806 of wafer 802 can be etched to form through-hole vias (e.g., through-silicon vias). The through-hole vias expose at least a portion of the electrically-conductive pads 814 such that pads 814 can be electrically coupled to a redistribution layer. After forming the through-hole vias, the second mask layer (e.g., a photoresist layer) can be removed.

Figure 8D:
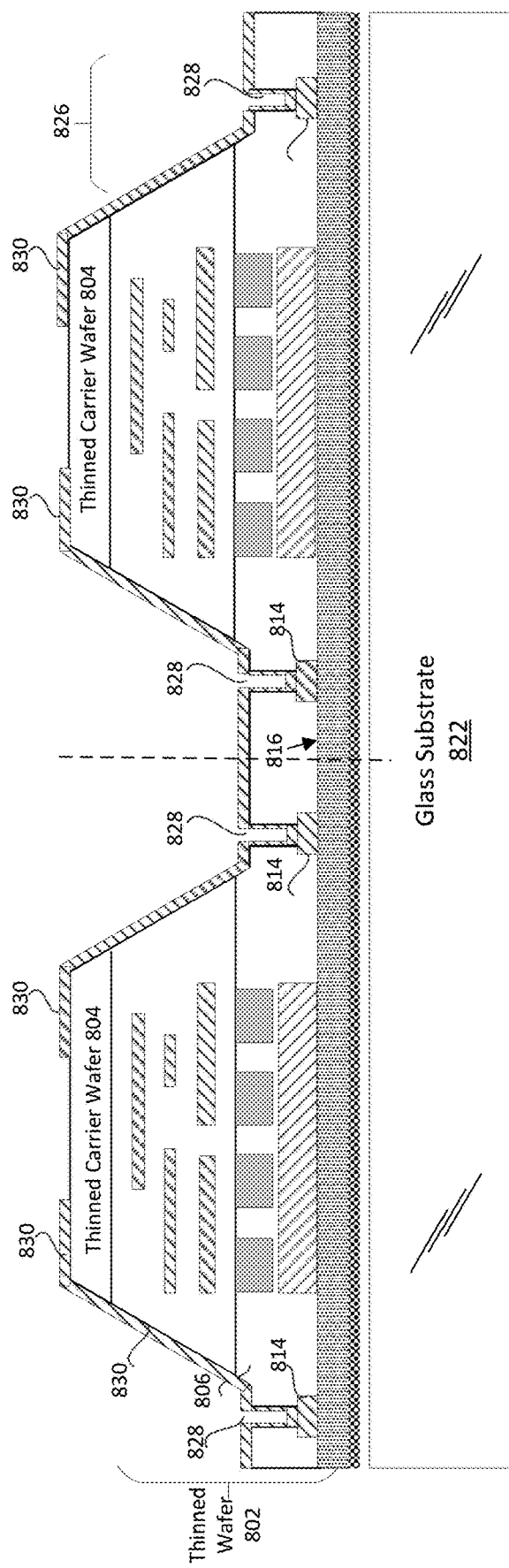

FIG. 8D illustrates depositing a redistribution layer 830. Redistribution layer 830 includes conductors (e.g., metals) at least partially enclosed by through-hole vias 828. In some embodiments, before depositing the conductors, a third mask layer (not shown) can be deposited to define pre-determined areas corresponding to one or more redistribution paths. Based on the defined pre-determined areas, one or more conductors can be deposited. The conductors can be metal-based conductors deposited using PVD (e.g., sputtering), CVD, PECVD, etc. Portions of the conductors of redistribution layer 830 can be deposited inside through-hole vias 828 and thus are partially enclosed by the corresponding through-hole vias 828. The conductors can be in contact with the corresponding electrically-conductive pads 814 disposed at surface 816 of the wafer 802. The conductors can extend from pads 814 to reroute electrical signals to desired areas. After the redistribution layer 830 has been deposited, the third mask layer can be removed.

Figure 8E:
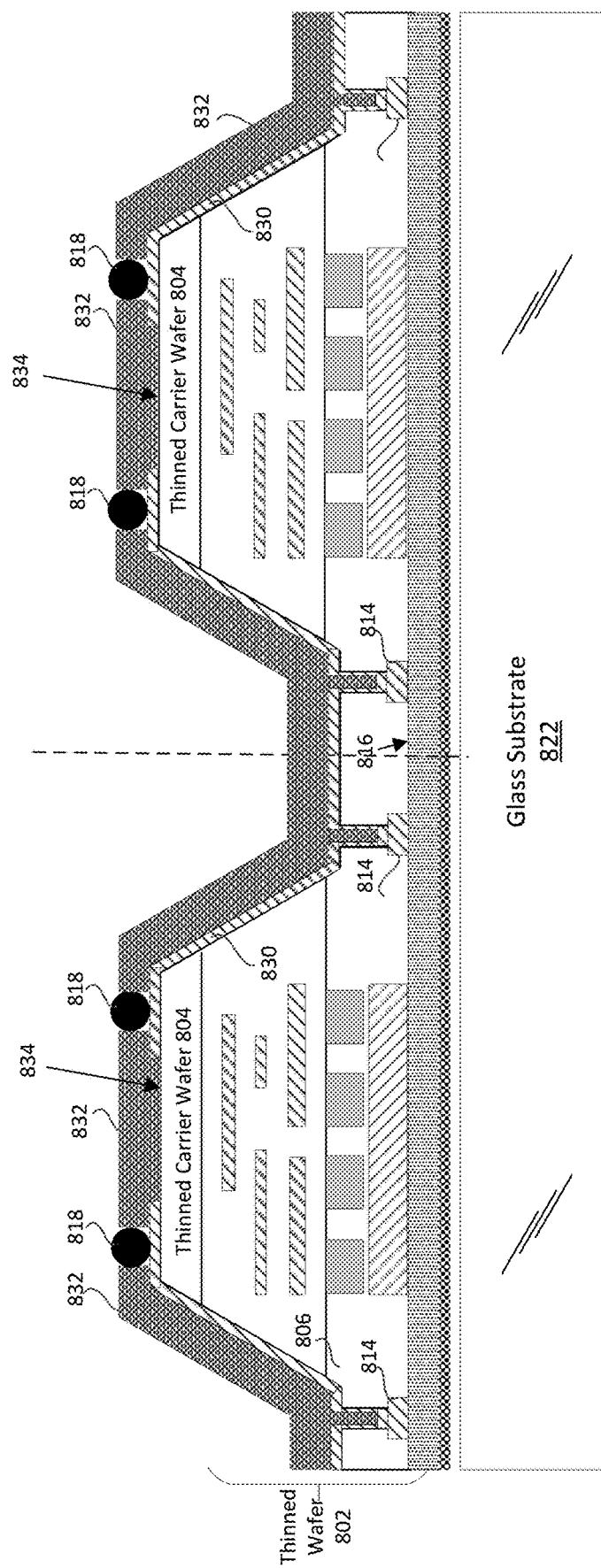

FIG. 8E illustrates forming a plurality of electrically-conductive spheres 818. As shown in FIG. 8E, before disposing spheres 818 (e.g., solder balls), a solder mask layer 832 can be deposited in contact with the redistribution layer 830 and other areas of the wafers 802 and 804 (e.g., back surface 834 where no redistribution layer 830 is deposited). A solder mark layer can be, for example, a thin layer of polymer for protection the redistribution layer 830 against oxidation and for preventing solder bridges from forming between closely spaced conductors or spheres. Next, a fourth mask layer can be deposited to define areas corresponding to areas for attaching the electrically-conductive spheres 818. Based on the defined areas, the solder mask layer can be etched to remove portions of the solder mask layer such that the underneath conductors of the redistribution layer 830 are exposed. The exposed conductors of the redistribution layer 830 can be in contact with spheres 818 for electrical coupling. Subsequent to the etching, the fourth mask layer can be removed. The electrically-conductive spheres 818 can be disposed at the areas defined for attaching the electrically-conductive spheres 818 (e.g., areas above the exposed conductors of the redistribution layer 830). As a result, the redistribution layer 830 electrically couples the plurality of electrically-conductive pads 814 to the plurality of electrically-conductive spheres 818. Thus, electrical signals can be redistributed or re-routed from pads 814 to spheres 818, which can then be electrically coupled to external signal processing circuitry. As described above, the signal redistribution or rerouting enables a more compact, effective, or efficient packaging for large scale sensing system, without the requirement of using wiring bonding.

Figure 8F:
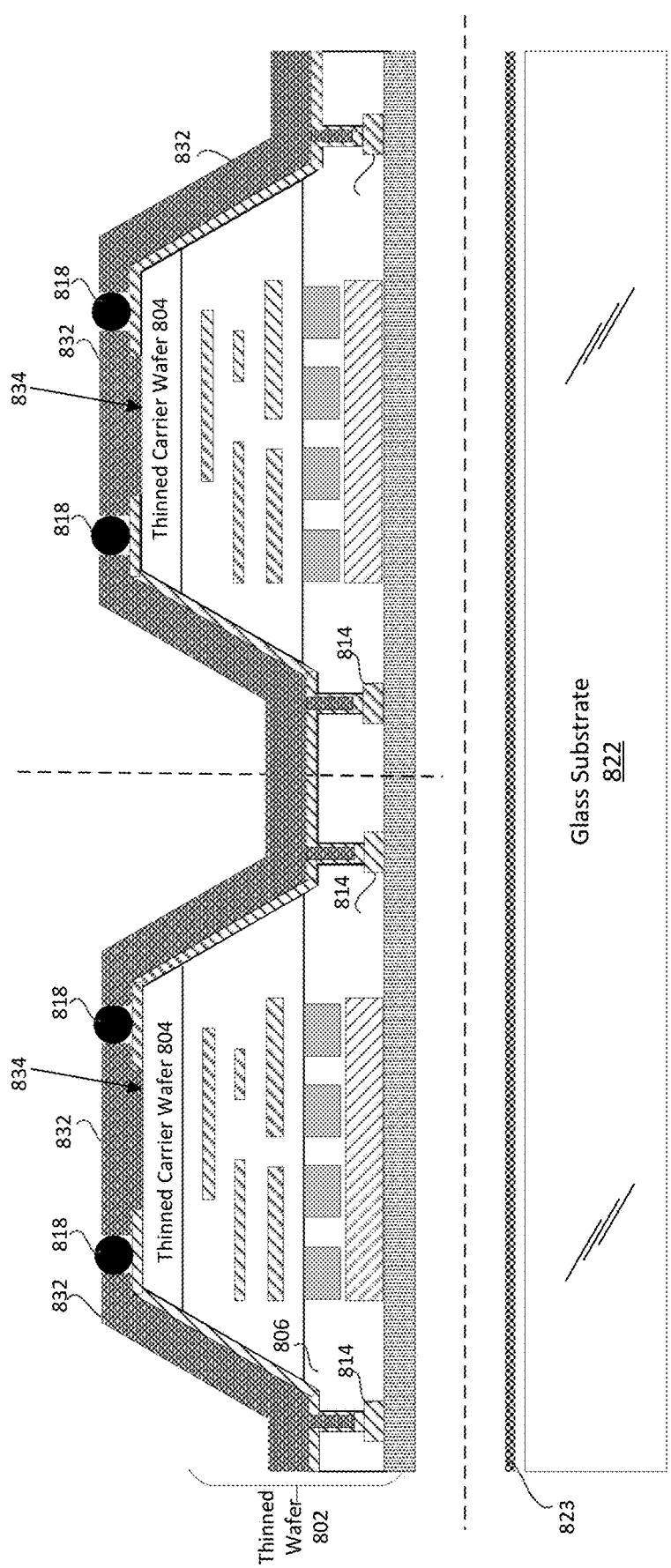

FIG. 8F illustrates a process of removing detachable glass substrate 822, which is adhesively bonded to wafer 802. As described above, glass substrate 822 is used to provide support to bonded wafers 802 and 804 so that the wafers may not be fractured or damaged during the processing steps. After the processes described above are completed, glass substrate 822 can be removed by, for example, dissolving the adhesive for bonding wafer 802 to glass substrate 822.

Figure 8G:
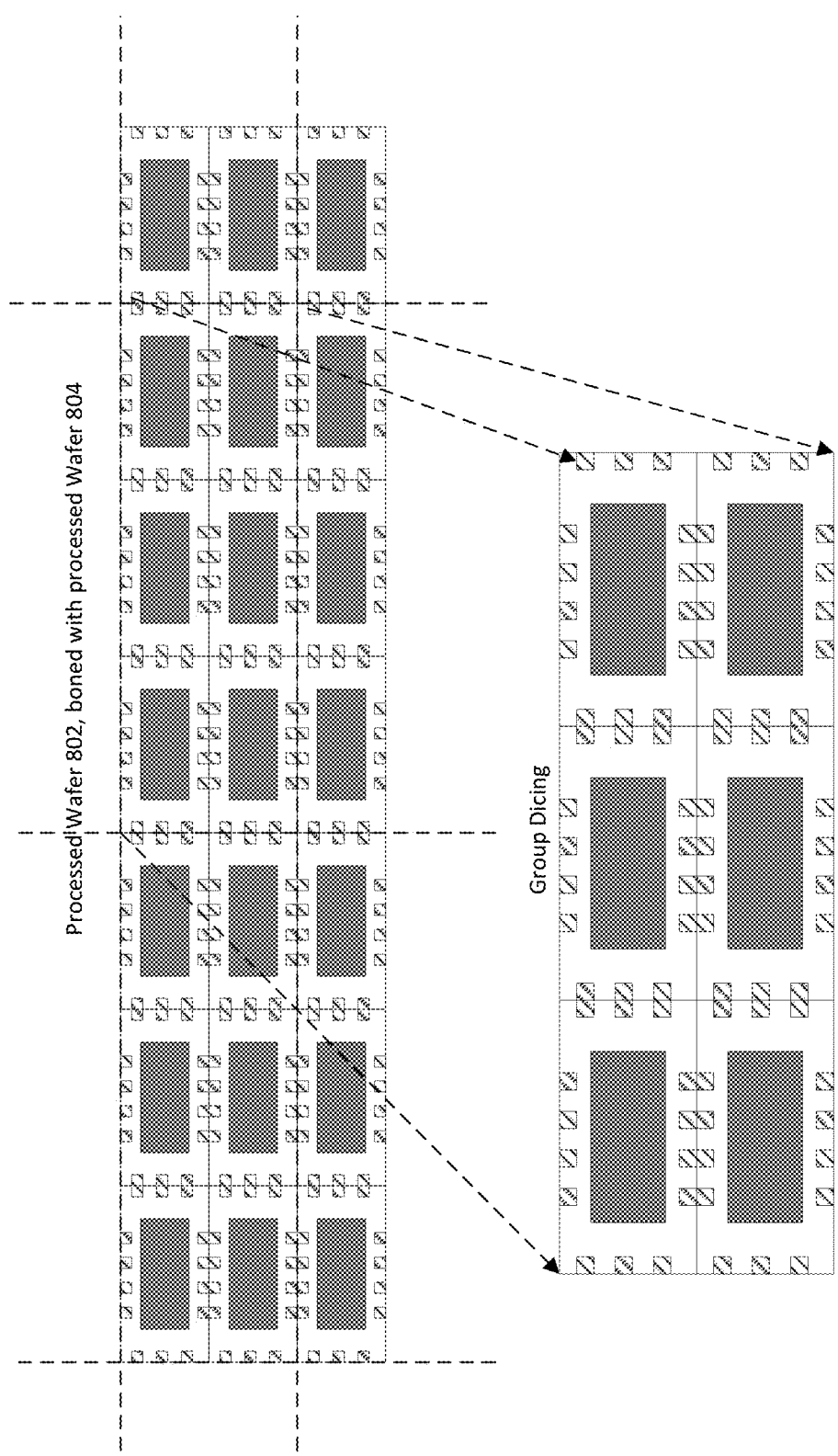

After the glass substrate 822 is removed, an array of semiconductor dies can be diced as a group from the plurality of semiconductor dies of processed wafer 802, which is bonded with processed wafer 804. The array of semiconductor dies includes a group of sensors associated with the throughput-scalable sensing system. FIG. 8G illustrates such a dicing process. FIG. 8G is the same or substantially the same as FIG. 2C, and thus is not repeatedly described.

Figure 9:
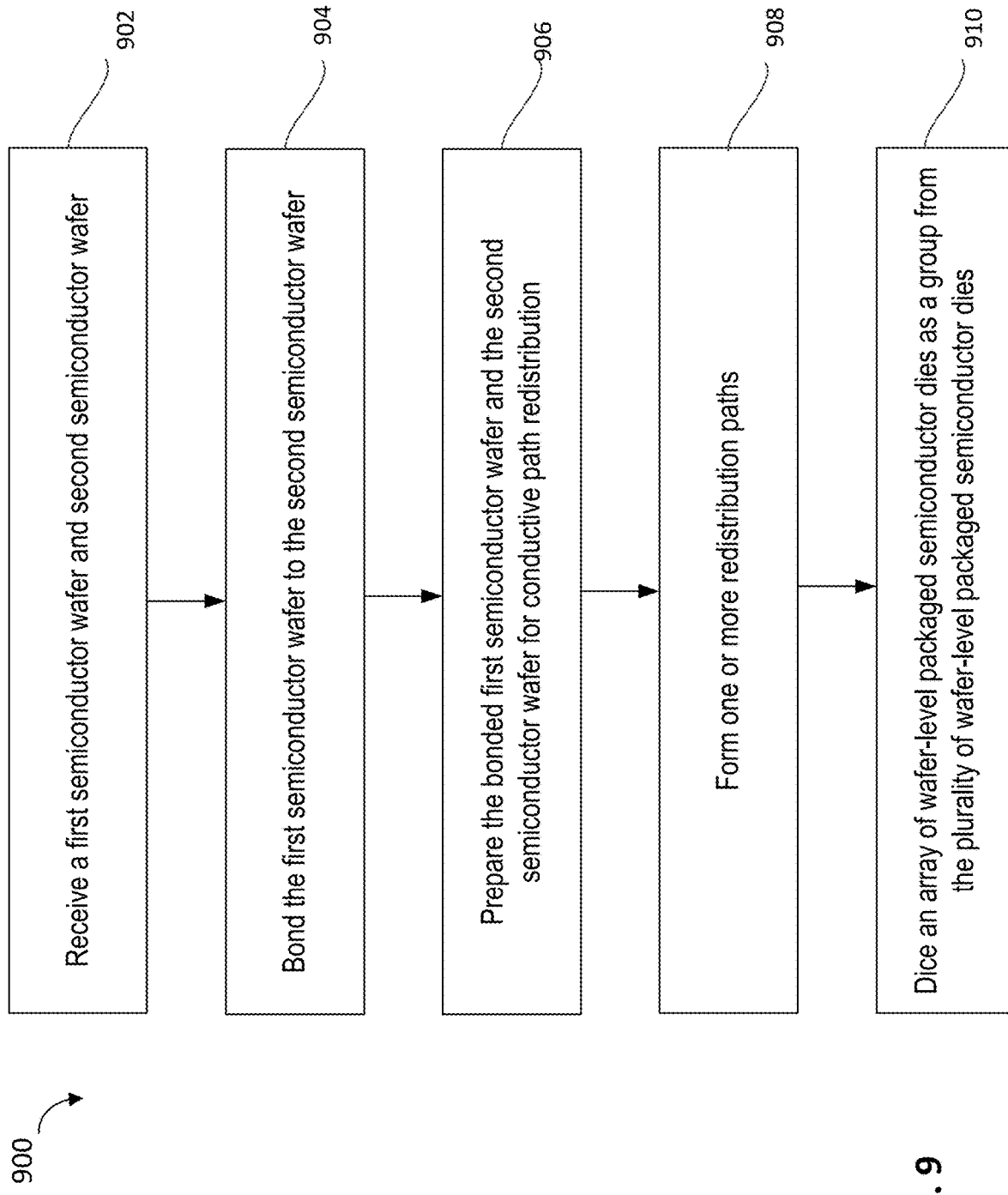
FIG. 9 is a flow chart illustrating a method for fabricating a throughput-scalable sensing system.

FIG. 9 is a flow diagram illustrating an exemplary method 900 for fabricating a throughput-scalable sensing system. In step 902 of method 900, a first semiconductor wafer (e.g., wafer 802 of FIG. 8A) and second semiconductor wafer (e.g., wafer 804 of FIG. 8A) are received. The first semiconductor wafer includes a semiconductor substrate and a plurality of sensors disposed in the semiconductor substrate. Each sensor of the plurality of sensors is disposed in a separate semiconductor die of the first semiconductor wafer.

At step 904, the first semiconductor wafer to the second semiconductor wafer are bonded together. FIG. 8B illustrates such a bonding process.

At step 906, the bonded first semiconductor wafer and the second semiconductor wafer is prepared for conductive path redistribution. FIG. 8C illustrates the processes for preparing the bonded wafers for conductive path redistribution.

At step 908, one or more redistribution paths are formed from a plurality of electrically-conductive pads disposed at a first surface of the prepared first semiconductor wafer to a plurality of electrically-conductive spheres disposed at a first surface of the prepared second semiconductor wafer. The one or more redistribution paths are partially enclosed by one or more through-hole vias. FIGS. 8D-8E illustrates the forming of redistribution paths.

At step 910 an array of semiconductor dies is diced as a group from a plurality of semiconductor dies. The array of semiconductor dies includes a group of sensors associated with the throughput-scalable sensing system. FIGS. 8F and 2C illustrate the group dicing process.

It is understood that the specific order or hierarchy of blocks in the processes and/or flowcharts disclosed is an illustration of exemplary approaches. Based upon design preferences, it is understood that the specific order or hierarchy of blocks in the block diagrams, processes and/or flowcharts may be rearranged. Further, some blocks may be combined or omitted. The accompanying method claims present elements of the various blocks in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more. Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The words "module," "mechanism," "element," "device," and the like may not be a substitute for the word "means." As such, no claim element is to be construed under 35 U.S.C. § 112(f) unless the element is expressly recited using the phrase "means for."

What is claimed is:

1. A method for fabricating a throughput-scalable sensing system, comprising:
    receiving a first semiconductor wafer and a second semiconductor wafer, wherein the first semiconductor wafer includes a semiconductor substrate and a plurality of sensors disposed in the semiconductor substrate, wherein each sensor of the plurality of sensors is disposed in a separate semiconductor die of the first semiconductor wafer;
    bonding the first semiconductor wafer to the second semiconductor wafer;
    preparing the bonded first semiconductor wafer and the second semiconductor wafer for conductive path redistribution, thereby providing a prepared first semiconductor wafer and a prepared second semiconductor wafer;
    forming one or more redistribution paths from a plurality of electrically-conductive pads disposed at a first surface of the prepared first semiconductor wafer to a plurality of electrically-conductive spheres disposed at a first surface of the prepared second semiconductor wafer, the one or more redistribution paths being partially enclosed by one or more through-hole vias;
    removing a detachable glass substrate adhesively bonded to the first semiconductor wafer; and
    dicing, based on a predetermined number of sensors required for the throughput-scalable sensing system, an array of semiconductor dies as a group from the first semiconductor wafer, wherein the array of semiconductor dies includes a group of sensors associated with the throughput-scalable sensing system.

2. The method of claim 1, further comprising, prior to receiving the first semiconductor wafer and the second semiconductor wafer:
    thinning the semiconductor substrate of the first semiconductor wafer from a back surface of the first semiconductor wafer, thereby forming a thinned back surface of the first semiconductor wafer, wherein the back surface of the first semiconductor wafer is a surface opposite to a front surface of the first semiconductor wafer, wherein the front surface of the first semiconductor wafer is disposed with one or more conductive layers and one or more dielectric layers; and
    depositing a passivation layer on the thinned back surface of the first semiconductor wafer.

3. The method of claim 1, further comprising:
    stacking a third semiconductor wafer with the first semiconductor wafer, wherein the third semiconductor wafer includes a signal processing circuitry.

4. The method of claim 1, wherein bonding the first semiconductor wafer to the second semiconductor wafer comprises:
    performing wafer bonding at a second surface of the first semiconductor wafer and a second surface of the second semiconductor wafer, wherein the second surface of the first semiconductor wafer is disposed with one or more conductive layers and one or more dielectric layers.

5. The method of claim 1, wherein preparing the bonded first semiconductor wafer and the second semiconductor wafer for conductive path redistribution comprises:
    adhesively bonding the detachable glass substrate to the first semiconductor wafer; and
    thinning a portion of the first semiconductor wafer and a portion of the second semiconductor wafer.

6. The method of claim 5, wherein thinning a portion of the first semiconductor wafer and a portion of the second semiconductor wafer comprises:
    thinning the second semiconductor wafer from a surface opposite to a bonded interface between the first semiconductor wafer and the second semiconductor wafer;
    depositing a first mask layer defining first pre-determined areas of the first semiconductor wafer;
    etching, based on the defined first pre-determined areas, a portion of the first semiconductor wafer and a portion of the thinned second semiconductor wafer, wherein the portion of the first semiconductor wafer being etched includes areas between neighboring semiconductor dies; and
    removing the first mask layer.

7. The method of claim 1, wherein forming the one or more redistribution paths from the plurality of electrically-conductive pads disposed at the first surface of the prepared first semiconductor wafer to the plurality of electrically-conductive spheres disposed at the first surface of the prepared second semiconductor wafer comprises:
    forming the one or more through-hole vias in the semiconductor substrate of the prepared first semiconductor wafer;
    depositing a redistribution layer, wherein the redistribution layer includes one or more conductors at least partially enclosed by the one or more through-hole vias; and
    forming a plurality of electrically-conductive spheres at the first surface of the prepared second semiconductor wafer, wherein the redistribution layer electrically couples the plurality of electrically-conductive pads to the plurality of electrically-conductive spheres.

8. The method of claim 7, wherein forming the one or more through-hole vias in the semiconductor substrate of the prepared first semiconductor wafer comprises:
    depositing a second mask layer defining second pre-determined areas of the first semiconductor wafer;
    etching, based on the defined second pre-determined areas, a portion of the semiconductor substrate of the first semiconductor wafer, wherein the portion of the semiconductor substrate of the first semiconductor wafer being etched includes areas corresponding to the electrically-conductive pads; and
    removing the second mask layer.

9. The method of claim 7, wherein depositing the redistribution layer comprises:
    depositing a third mask layer defining third pre-determined areas corresponding to the one or more redistribution paths;
    depositing, based on the defined third pre-determined areas, the one or more conductors, and wherein the one or more conductors are in contact with the corresponding electrically-conductive pads disposed at the first surface of the prepared first semiconductor wafer; and
removing the third mask layer.

10. The method of claim 7, wherein forming the plurality of electrically-conductive spheres at the first surface of the prepared second semiconductor wafer comprises:
depositing a solder mask layer in contact with at least a portion of the redistribution layer;
depositing a fourth mask layer defining fourth pre-determined areas corresponding to areas for attaching the plurality of electrically-conductive spheres;
etching, based on the defined fourth pre-determined areas, the solder mask layer;
removing the fourth mask layer; and
disposing the plurality of electrically-conductive spheres at areas defined for attaching the electrically-conductive spheres.

11. The method of claim 1, wherein dicing, based on the predetermined number of sensors required for the throughput-scalable sensing system, the array of semiconductor dies as a group comprises:
determining, based on a total number of semiconductor dies of the first semiconductor wafer and based on the predetermined number of sensors required for the throughput-scalable sensing system, a group dicing plan; and
dicing, based on the group dicing plan, the array of semiconductor dies as a group from the first semiconductor wafters.

12. The method of claim 1, further comprising, prior to dicing the array of semiconductor dies as a group from the first semiconductor wafer:
determining a throughput scaling requirement of the throughput-scalable sensing system;
determining a throughput capacity of each sensor of the plurality of sensors; and
determining, based on the throughput scaling requirement and the throughput capacity, the predetermined number of sensors required for the throughput-scalable sensing system, wherein the predetermined number of sensors required for the throughput-scalable sensing system corresponds to a number of semiconductor dies in the group.

13. A method for fabricating a throughput-scalable sensing system, comprising:
receiving a first semiconductor wafer and a second semiconductor wafer, wherein the first semiconductor wafer includes a semiconductor substrate and a plurality of sensors disposed in the semiconductor substrate, wherein each sensor of the plurality of sensors is disposed in a separate semiconductor die of the first semiconductor wafer;
bonding the first semiconductor wafer to the second semiconductor wafer;
adhesively bonding a detachable glass substrate to the first semiconductor wafer;
thinning a portion of the first semiconductor wafer and a portion of the second semiconductor wafer;
forming one or more redistribution paths from a plurality of electrically-conductive pads disposed at a first surface of the first semiconductor wafer to a plurality of electrically-conductive spheres disposed at a first surface of the second semiconductor wafer, the one or more redistribution paths being partially enclosed by one or more through-hole vias; and
dicing an array of semiconductor dies as a group from a plurality of semiconductor dies of the first semiconductor wafer, wherein the array of semiconductor dies includes a group of sensors associated with the throughput-scalable sensing system.

14. The method of claim 13, further comprising, prior to receiving the first semiconductor wafer and the second semiconductor wafer:
thinning the semiconductor substrate of the first semiconductor wafer from a back surface of the first semiconductor wafer, thereby forming a thinned back surface of the first semiconductor wafer, wherein the back surface of the first semiconductor wafer is a surface opposite to a front surface of the first semiconductor wafer, wherein the front surface of the first semiconductor wafer is disposed with one or more conductive layers and one or more dielectric layers; and
depositing a passivation layer on the thinned back surface of the first semiconductor wafer.

15. The method of claim 13, further comprising:
stacking a third semiconductor wafer with the first semiconductor wafer, wherein the third semiconductor wafer includes a signal processing circuitry.

16. The method of claim 13, wherein bonding the first semiconductor wafer to the second semiconductor wafer comprises:
performing wafer bonding at a second surface of the first semiconductor wafer and a second surface of the second semiconductor wafer, wherein the second surface of the first semiconductor wafer is disposed with one or more conductive layers and one or more dielectric layers.

17. The method of claim 13, wherein thinning a portion of the first semiconductor wafer and a portion of the second semiconductor wafer comprises:
thinning the second semiconductor wafer from a surface opposite to a bonded interface between the first semiconductor wafer and the second semiconductor wafer;
depositing a first mask layer defining first pre-determined areas of the first semiconductor wafer;
etching, based on the defined first pre-determined areas, a portion of the first semiconductor wafer and a portion of the thinned second semiconductor wafer, wherein the portion of the first semiconductor wafer being etched includes areas between neighboring semiconductor dies; and
removing the first mask layer.

18. The method of claim 13, wherein forming the one or more redistribution paths from the plurality of electrically-conductive pads disposed at the first surface of the first semiconductor wafer to the plurality of electrically-conductive spheres disposed at the first surface of the second semiconductor wafer comprises:
forming the one or more through-hole vias in the semiconductor substrate of the first semiconductor wafer;
depositing a redistribution layer, wherein the redistribution layer includes one or more conductors at least partially enclosed by the one or more through-hole vias; and
forming a plurality of electrically-conductive spheres at the first surface of the second semiconductor wafer, wherein the redistribution layer electrically couples the plurality of electrically-conductive pads to the plurality of electrically-conductive spheres.

19. The method of claim 18, wherein forming the one or more through-hole vias in the semiconductor substrate of the first semiconductor wafer comprises:
depositing a second mask layer defining second pre-determined areas of the first semiconductor wafer;

etching, based on the defined second pre-determined areas, a portion of the semiconductor substrate of the first semiconductor wafer, wherein the portion of the semiconductor substrate of the first semiconductor wafer being etched includes areas corresponding to the electrically-conductive pads; and removing the second mask layer.

20. The method of claim 18, wherein depositing the redistribution layer comprises:
depositing a third mask layer defining third pre-determined areas corresponding to the one or more redistribution paths;
depositing, based on the defined third pre-determined areas, the one or more conductors, and wherein the one or more conductors are in contact with the corresponding electrically-conductive pads disposed at the first surface of the first semiconductor wafer; and
removing the third mask layer.

21. The method of claim 18, wherein forming the plurality of electrically-conductive spheres at the first surface of the second semiconductor wafer comprises:
depositing a solder mask layer in contact with at least a portion of the redistribution layer;
depositing a fourth mask layer defining fourth pre-determined areas corresponding to areas for attaching the plurality of electrically-conductive spheres;
etching, based on the defined fourth pre-determined areas, the solder mask layer;
removing the fourth mask layer; and
disposing the plurality of electrically-conductive spheres at areas defined for attaching the electrically-conductive spheres.

22. The method of claim 13, wherein dicing the array of semiconductor dies as a group from the plurality of semiconductor dies comprises:

removing the detachable glass substrate adhesively bonded to the first semiconductor wafer; and
dicing, based on a predetermined number of sensors required for the throughput-scalable sensing system, the array of semiconductor dies as a group from the plurality of semiconductor dies of the first semiconductor wafer.

23. The method of claim 22, wherein dicing, based on the predetermined number of sensors required for the throughput-scalable sensing system, the array of semiconductor dies as a group comprises:
determining, based on a total number of semiconductor dies of the first semiconductor wafer and based on the predetermined number of sensors required for the throughput-scalable sensing system, a group dicing plan; and
dicing, based on the group dicing plan, the array of semiconductor dies as a group from the plurality of semiconductor dies.

24. The method of claim 13, further comprising, prior to dicing the array of semiconductor dies as a group from the plurality of semiconductor dies:
determining a throughput scaling requirement of the throughput-scalable sensing system;
determining a throughput capacity of each sensor of the plurality of sensors; and
determining, based on the throughput scaling requirement and the throughput capacity, the predetermined number of sensors required for the throughput-scalable sensing system, wherein the predetermined number of sensors required for the throughput-scalable sensing system corresponds to a number of semiconductor dies in the group.

* * * * *